(12) United States Patent
Choi et al.

(10) Patent No.: US 9,799,839 B2
(45) Date of Patent: *Oct. 24, 2017

US009799839B2

(54) ORGANOMETALLIC COMPOUND AND ORGANIC LIGHT-EMITTING DIODE COMPRISING THE SAME

(71) Applicant: SAMSUNG DISPLAY CO., LTD., Yongin, Gyeonggi-do (KR)

(72) Inventors: Jong-Won Choi, Yongin (KR); Yoon-Hyun Kwak, Yongin (KR); Bum-Woo Park, Yongin (KR); Sun-Young Lee, Yongin (KR); Wha-Il Choi, Yongin (KR); So-Yeon Kim, Yongin (KR); Ji-Youn Lee, Yongin (KR)

(73) Assignee: Samsung Diplay Co., Ltd., Yongin-si (KR)

( * ) Notice: Subject to any disclaimer, the term of this patent is extended or adjusted under 35 U.S.C. 154(b) by 871 days.

This patent is subject to a terminal disclaimer.

(21) Appl. No.: 14/080,471

(22) Filed: Nov. 14, 2013

(65) Prior Publication Data

US 2014/0183467 A1 Jul. 3, 2014

(30) Foreign Application Priority Data

Dec. 27, 2012 (KR) .................. 10-2012-0155318

(51) Int. Cl.
| | | |
|---|---|---|
| H01L 51/54 | (2006.01) | |
| C09K 11/06 | (2006.01) | |
| H01L 51/00 | (2006.01) | |
| C07F 15/00 | (2006.01) | |
| H01L 51/50 | (2006.01) | |

(52) U.S. Cl.
CPC ...... *H01L 51/0087* (2013.01); *C07F 15/0093* (2013.01); *C09K 11/06* (2013.01); *C09K 2211/1029* (2013.01); *C09K 2211/1044* (2013.01); *C09K 2211/1059* (2013.01); *C09K 2211/185* (2013.01); *H01L 51/5016* (2013.01)

(58) Field of Classification Search
None
See application file for complete search history.

(56) References Cited

U.S. PATENT DOCUMENTS

| 6,465,115 | B2 | 10/2002 | Shi et al. | |
|---|---|---|---|---|
| 6,596,415 | B2 | 7/2003 | Shi et al. | |
| 7,002,013 | B1 | 2/2006 | Chi et al. | |
| 7,759,490 | B2 | 7/2010 | Tao et al. | |
| 7,868,170 | B2 | 1/2011 | Chi et al. | |
| 7,915,414 | B2 | 3/2011 | Chi et al. | |
| 9,373,798 | B2 * | 6/2016 | Choi et al. | C07F 15/0026 |
| 2001/0019782 | A1 | 9/2001 | Igarashi et al. | |
| 2002/0134984 | A1 * | 9/2002 | Igarashi | C09K 11/06 257/79 |
| 2008/0001530 | A1 * | 1/2008 | Ise et al. | C09K 11/06 313/504 |
| 2009/0171087 | A1 | 7/2009 | Chi et al. | |

FOREIGN PATENT DOCUMENTS

| JP | 2000-003782 A | 1/2000 |
|---|---|---|
| JP | 2011119576 A | 6/2011 |

OTHER PUBLICATIONS

Huang et al., "Mechanoluminescent and efficient white OLEDs for Pt(II) phosphors bearing spatially encumbered pyridinyl pyrazolate chelates", Journal of Materials Chemistry C, vol. 1, pp. 7582-7592 (Sep. 16, 2013).*
Baldo et al., "Highly efficient phosphorescent emission from organic electroluminescent devices", Nature, vol. 395, (Sep. 10, 1998), pp. 151-154.
Baldo et al., "Very high-efficiency green organic light-emitting devices based on electrophosphorescence", Applied Physics Letters, vol. 75, No. 1, ( Jul. 5, 1999), pp. 4-6.
Lamansky et al., "Synthesis and Characterization of Phosphorescent Cyclometalated Iridium Complexes", Inorganic Chemistry, vol. 40, No. 7, 2001, pp. 1704-1711.
Lamansky et al., "Highly Phosphorescent Bis-Cyclometalated Iridium Complexes: Synthesis, Photophysical Characterization, and Use in Organic Light Emitting Diodes", Journal of the American Chemical Society, vol. 123, No. 18, 2001, pp. 4304-4312.
Hsieh et al., "Platinum (II) complexes with spatially encumbered chelates; syntheses, structure and photophysics", Inorganica Chimica Acta, vol. 362, 2009, pp. 4734-4739.
Chi et al., "Light Emitting Materials for Organic Electronics", Journal of Photopolymer Science and Technology, vol. 21, No. 3, 2008, pp. 357-362.
Korean Office Action issued by Korean Intellectual Property Office on Oct. 19, 2015 in connection with Korean Patent Application No. 10-2012-0155318 and Request for Entry attached herewith.

\* cited by examiner

*Primary Examiner* — Marie R. Yamnitzky
(74) *Attorney, Agent, or Firm* — H.C. Park & Associates, PLC

(57) ABSTRACT

An organometallic compound and an organic light-emitting diode (OLED) including the organometallic compound are provided. In exemplary embodiments, the organometallic compound is a platinum complex comprising one or two heterocyclic ligands, the heterocyclic ligands being the same or different if they are two in number, each heterocyclic ligand comprising two nitrogen heterocyclic rings connected by a single bond, one of the rings being six membered and comprising at least one nitrogen and the other ring being a 1,2-diazole or a 1,2,4-triazole ring. One or two other organic ligands may be attached to the central platinum atom in the complex. OLEDs including one of the subject platinum compounds in a light emission layer exhibit lower driving voltages, higher luminances, higher efficiencies and longer lifetimes than do comparative OLEDs built with established dopants incorporated into the light emitting layers.

14 Claims, 1 Drawing Sheet

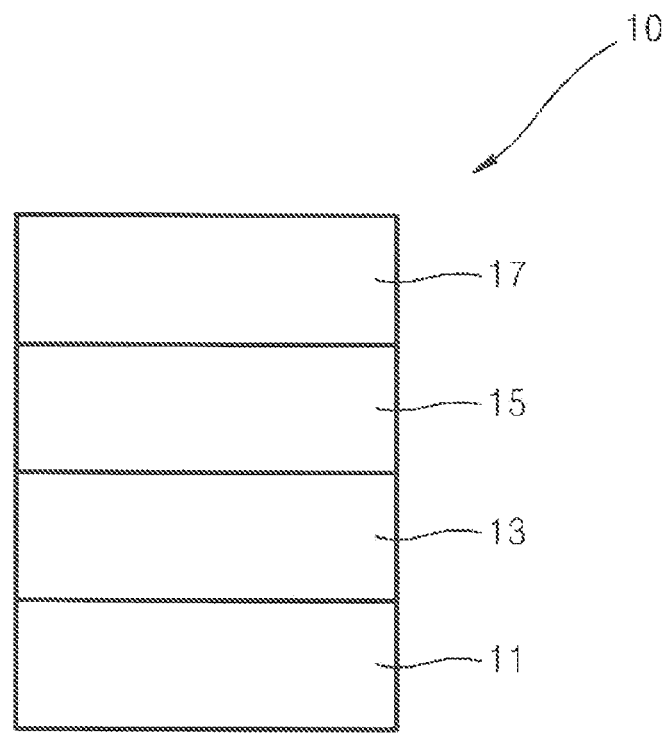

ORGANOMETALLIC COMPOUND AND ORGANIC LIGHT-EMITTING DIODE COMPRISING THE SAME

CLAIM OF PRIORITY

This application makes reference to, incorporates the same herein, and claims all benefits accruing under 35 U.S.C. §119 from an application for ORGANOMETALLIC COMPOUND AND ORGANIC LIGHT-EMITTING DIODE COMPRISING THE SAME, earlier filed in the Korean Intellectual Property Office on Dec. 27, 2012 and there duly assigned Serial No. 10-2012-0155318.

BACKGROUND OF THE INVENTION

Field of the Invention

One or more embodiments of the present invention relate to a compound useful in the construction of organic light-emitting diodes and an organic light-emitting diode including the compound.

Description of the Related Art

Organic light-emitting diodes (OLEDs), which are self-emitting diodes, have advantages such as wide viewing angles, excellent contrast, quick response, high brightness and excellent driving voltage characteristics, and they can provide multicolored images.

A typical OLED has a structure including a substrate, and an anode, a hole transport layer (HTL), an emission layer (EML), an electron transport layer (ETL) and a cathode, which are sequentially stacked on the substrate. In this regard, the HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY OF THE INVENTION

One or more embodiments of the present invention include an organometallic compound having a novel structure and an organic light-emitting diode including the same.

Additional aspects will be set forth in part in the description which follows and, in part, will be apparent from the description, or may be learned by practice of the presented embodiments.

According to one or more embodiments of the present invention, there is provided an organometallic compound represented by Formula 1 below:

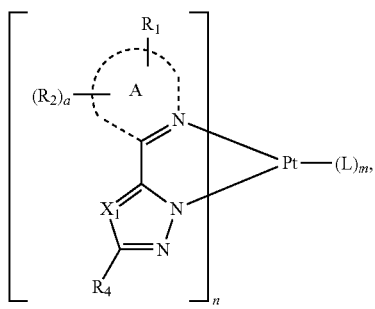

<Formula 1> the A ring in Formula 1 being one of a 6-membered ring including at least one nitrogen atom (N), a 6-membered ring condensed with at least one 5-membered ring and including at least one N, and a 6-membered ring condensed with at least one 6-membered ring and including at least one N;

$R_1$ in Formula 1 being a substituted or unsubstituted linear or branched $C_2$-$C_{60}$ alkyl group;

$X_1$ in Formula 1 being one of N and $C(R_3)$;

$R_2$ to $R_4$ in Formula 1 being each independently selected from among a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted a $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, $-N(Q_1)(Q_2)$, $-Si(Q_3)(Q_4)(Q_5)$, $-C(=O)(Q_6)$ (where $Q_1$ to $Q_6$ are each independently one of a hydrogen atom, a substituted or unsubstituted $C_1$-$C_{60}$ alkyl group, a substituted or unsubstituted $C_6$-$C_{60}$ aryl group, and a substituted or unsubstituted $C_2$-$C_{60}$ heteroaryl group), and a binding site of an adjacent ligand via a single bond or a divalent linking group, $R_3$ and $R_4$ being optionally linked to each other to form one of a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, and a substituted or unsubstituted $C_2$-$C_{20}$ heteroaromatic group;

a in Formula 1 being an integer from 1 to 10, the at least two of $R_{2s}$ being identical to or different from each other when a is 2 or greater;

n in Formula 1 being 1 or 2, the two groups represented by

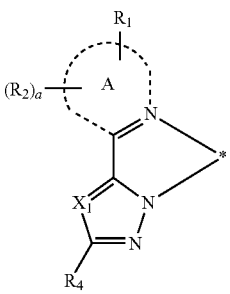

being identical to or different from each other when n is 2;

L in Formula 1 being an organic ligand; and m in Formula 1 being an integer from 0 to 2.

According to one or more embodiments of the present invention, an organic light-emitting diode includes: a substrate; a first electrode; a second electrode disposed opposite to the first electrode; and an emission layer disposed between the first electrode and the second electrode, the emission layer comprising at least one of the organometallic compounds of Formula 1 above.

BRIEF DESCRIPTION OF THE DRAWING

A more complete appreciation of the invention and many of the attendant advantages thereof will be readily apparent as the same becomes better understood by reference to the following detailed description when considered in conjunction with the accompanying drawing in which like reference symbols indicate the same or similar components, wherein:

The FIGURE is a schematic view of a structure of an organic light-emitting diode according to an embodiment of the present invention.

DETAILED DESCRIPTION OF THE INVENTION

Reference will now be made in detail to embodiments, examples of which are illustrated in the accompanying drawings, like reference numerals referring to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an embodiment of the present invention, there is provided an organometallic compound represented by Formula 1 below:

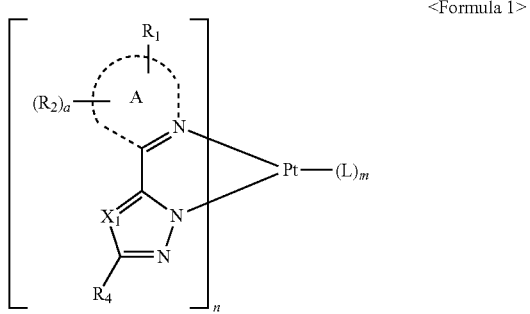

<Formula 1>

In Formula 1, an A ring may be one of a 6-membered ring including at least one nitrogen atom (N), a 6-membered ring condensed with at least one 5-membered ring and including at least one N, and a 6-membered ring condensed with at least one 6-membered ring and including at least one N. The A ring may include substituents $R_1$ and $R_2$, as identified in Formula 1, and detailed descriptions of the substituents will be provided later.

In Formula 1, the A ring may be one of pyridine, pyrazine, pyrimidine, pyridazine, purine, isoquinoline, quinoline, phthalazine, 1,8-naphthyridin, quinoxaline, quinazoline, cinnoline, phenanthridine, 1,7-phenanthroline, and pyrrolopyrimidine, but it is not limited thereto.

For example, the A ring may be one of pyridine, pyrimidine, isoquinoline and quinazoline, but it is not limited thereto.

$R_1$ as an "essential" substituent of the A ring may be a substituted or unsubstituted linear or branched $C_2$-$C_{60}$ alkyl group. For example, $R_1$ may be a substituted or unsubstituted linear or branched $C_2$-$C_{10}$ alkyl group.

In some embodiments, $R_1$ may be one selected from among, but not limited to:

an ethyl group, a n-propyl group, an i-propyl group, a n-butyl group, an i-butyl group, a t-butyl group, a pentyl group, a hexyl group, a heptyl group, an octyl group, a nonyl group, and a decyl group; and an ethyl group, n-propyl group, i-propyl group, n-butyl group, i-butyl group, t-butyl group, a pentyl group, a hexyl group, a heptyl group, an octyl group, a nonyl group, and a decyl group, each substituted with at least one of a deuterium atom, —F, a hydroxyl group, a cyano group, a nitro group, and an amino group.

In Formula 1, $X_1$ may be one of N and $C(R_3)$.

In Formula 1, $R_2$ to $R_4$ may be each independently selected from among a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —$N(Q_1)(Q_2)$, —$Si(Q_3)(Q_4)(Q_5)$, —$C(=O)(Q_6)$ (where $Q_1$ to $Q_6$ may be each independently one of a hydrogen atom, a substituted or unsubstituted $C_1$-$C_{60}$ alkyl group, a substituted or unsubstituted $C_6$-$C_{60}$ aryl group, and a substituted or unsubstituted $C_2$-$C_{60}$ heteroaryl group), and a binding site of an adjacent ligand via a single bond or a divalent linking group, $R_3$ and $R_4$ being optionally linked to each other to form one of a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, and a substituted or unsubstituted $C_2$-$C_{20}$ heteroaromatic group.

In some embodiments, in Formula 1, $X_1$ may be $C(R_3)$, and $R_2$ to $R_4$ may be each independently one selected from among:

a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phoshoric acid group or a salt thereof;

a methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group; and a methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, each substituted with at least one of a deuterium atom, —F, a hydroxyl group, a cyano group, a nitro group, and an amino group, $R_3$ and $R_4$ being optionally linked to each other to form one of a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, and a substituted or unsubstituted $C_2$-$C_{20}$ heteroaromatic group.

For example, $R_3$ and $R_4$ may be optionally linked to each other to form one selected from among, but not limited to:

cyclopropane, cyclobutane, cyclopentane, cyclohexane, cycloheptane, cyclooctane, cyclopentene, cyclopentadiene, cyclohexadiene, cycloheptadiene, bicyclo-heptane, bicyclo-octane, benzene, pentalene, indene, naphtalene, azulene, heptalene, indacene, acenaphthylene, fluorene, spiro-fluorene, phenalene, phenanthrene, anthracene, fluoranthene, triphenylene, pyrene, and chrysene; and cyclopropane, cyclobutane, cyclopentane, cyclohexane, cycloheptane, cyclooctane, cyclopentene, cyclopentadiene, cyclohexadiene, cycloheptadiene, bicyclo-heptane, bicyclo-octane, benzene, pentalene, indene, naphtalene, azulene, heptalene, indacene, acenaphthylene, fluorene, spiro-fluorene, phenalene, phenanthrene, anthracene, fluoranthene, triphenylene, pyrene, and chrysene, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, —N($Q_{11}$)($Q_{12}$), and —Si($Q_{13}$)($Q_{14}$)($Q_{15}$) (where $Q_{11}$ to $Q_{15}$ are each independently one of a hydrogen atom, a $C_1$-$C_{10}$ alkyl group, a $C_6$-$C_{20}$ aryl group and a $C_2$-$C_{20}$ heteroaryl group).

$R_2$ is a substituent of the A ring in Formula 1. In Formula 1, a, which indicates number of $R_2$s, may be an integer from 1 to 10. When $R_2$ is a hydrogen atom, the A ring of Formula 1 may have only the substituent $R_1$. When a is 2 or greater, the at least two $R_2$s may be identical to or differ from each other.

In Formula 1, n indicates number of ligands represented by

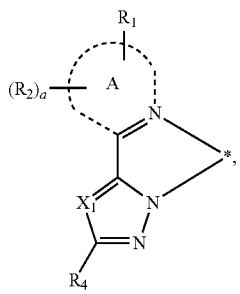

and may be an integer from 1 or 2. When n is 2, the two ligands of

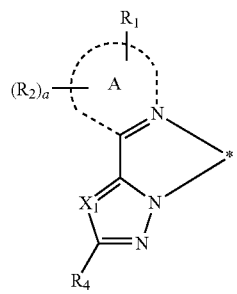

may be identical to or differ from each other.

In Formula 1, L indicates an organic ligand, which may serve as an auxiliary ligand relative to the ligand of

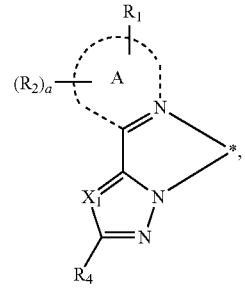

and m, which indicates number of Ls, may be an integer from 0 to 2.

In Formula 1, L may include a ligand represented by one of Formulae 2A to 2F:

$$*-C\equiv C-R_{31}$$ Formula 2A $$R_{32a}-M_1-R_{32c}$$ Formula 2B
(with $R_{32b}$ above $M_1$ and $*$ below)

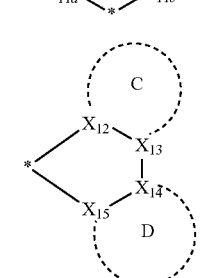 Formula 2C

Formula 2D
(ring C with $X_{12}$, $X_{13}$, $X_{14}$, $X_{15}$ and ring D)

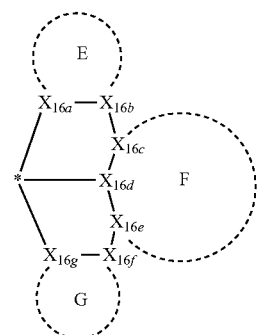 Formula 2E

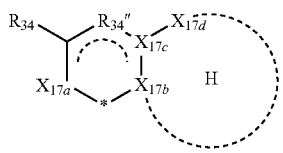 Formula 2F

In Formulae 2A to 2F, $M_1$ may be P or As;

$X_{11a}$, $X_{11b}$, $X_{12}$, $X_{13}$, $X_{14}$, $X_{15}$, $X_{16a}$, $X_{16b}$, $X_{16c}$, $X_{16d}$, $X_{16e}$, $X_{16f}$, $X_{16g}$, $X_{17a}$, $X_{17b}$, $X_{17c}$, and $X_{17d}$ may be each independently C, N, O, N($R_{35}$), P($R_{36}$)($R_{37}$), or As($R_{38}$)($R_{39}$);

$R_{33''}$ and $R_{34''}$ may be each independently one of a single bond, a substituted or unsubstituted $C_1$-$C_5$ alkylene group and a substituted or unsubstituted $C_2$-$C_5$ alkenylene group;

$R_{31}$, $R_{32a}$, $R_{32b}$, $R_{32c}$, $R_{33a}$, $R_{33b}$, $R_{34}$, $R_{35}$, $R_{36}$, $R_{37}$, $R_{38}$, and $R_{39}$ may be each independently selected from among a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, and a substituted or unsubstituted $C_2$-$C_{60}$ heteroaryl group;

a C ring, a D ring, an E ring, a F ring, a G ring, and a H ring may be each independently selected from a 5-membered to 20-membered saturated ring and a 5-membered to 20-membered unsaturated ring; and

* indicates a binding site of M in Formula 1.

In some embodiments, in Formulae 2A to 2F, $R_{31}$, $R_{32a}$, $R_{32b}$, $R_{32c}$, $R_{33a}$, $R_{33b}$, $R_{34}$, $R_{35}$, $R_{36}$, $R_{37}$, $R_{38}$, and $R_{39}$ may be each independently one selected from among:

a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group, and a $C_1$-$C_{20}$ alkoxy group, each substituted with at least one of a deuterium atom, a halogen atom, a hydroxyl group, a cyano group, a nitro group, and an amino group;

a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group, each substituted with at least one of a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group.

In some embodiments, L in Formula 1 may include a ligand represented by Formula 2B above. In this regard, in Formula 2B, $M_1$ may be P, and $R_{32a}$, $R_{32b}$ and $R_{32c}$ may be each independently one selected from among:

a $C_1$-$C_{20}$ alkyl group; a $C_1$-$C_{20}$ alkyl group substituted with at least one of a deuterium atom, a halogen atom, a hydroxyl group, a cyano group, a nitro group, and an amino group;

a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group, each substituted with at least one of a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group.

In some other embodiments, L in Formula 1 may include a ligand represented by Formula 2C above. In this regard, in Formula 2C, $X_{11a}$ and $X_{11b}$ may be $P(R_{36})(R_{37})$, and $R_{33''}$ may be one of a $C_1$-$C_5$ alkylene group and a $C_2$-$C_5$ alkenylene group, and $R_{36}$ and $R_{37}$ may be each independently one selected from among a $C_1$-$C_{20}$ alkyl group; a $C_1$-$C_{20}$ alkyl group substituted with at least one of a deuterium atom, a halogen atom, a hydroxyl group, a cyano group, a nitro group, and an amino group; a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group, each substituted with at least one of a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group.

In still other embodiments, when L in Formula 1 includes a ligand represented by Formula 2C above, $X_{11a}$ and $X_{11b}$ in Formula 2C may be O, and $R_{33''}$ may be one selected from among, a $C_1$-$C_5$ alkylene group and a $C_2$-$C_5$ alkenylene group; a $C_1$-$C_5$ alkylene group substituted with at least one of a deuterium atom, a halogen atom, a hydroxyl group, a cyano group, a nitro group, an amino group, a $C_1$-$C_{10}$ alkyl group, and a $C_1$-$C_{10}$ alkoxy group; and a $C_2$-$C_5$ alkenylene group substituted with at least one of a deuterium atom, a halogen atom, a hydroxyl group, a cyano group, a nitro group, an amino group, a $C_1$-$C_{10}$ alkyl group, and a $C_1$-$C_{10}$ alkoxy group.

In Formula 1, n may be 1 or 2, and m may be 0, 1, or 2, but they are not limited thereto. For example, in Formula 1, n may be 2 and m may be 0. Alternatively, n may be 1 and m may be 1.

The organometallic compound may be a compound represented by Formula 1(1):

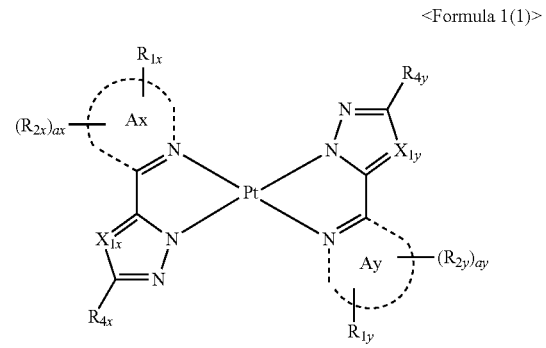

<Formula 1(1)>

In Formula 1(1), an Ax ring and an Ay ring may be each independently one of a 6-membered ring including at least one N, a 6-membered ring condensed with at least one 5-membered ring and including at least one N, and a 6-membered ring condensed with at least one 6-membered ring and including at least one N. The detailed descriptions of the A ring in the specification may be referred to as descriptions of the Ax ring and the Ay ring.

In Formula 1(1), $R_{1x}$ and $R_{1y}$ may be each independently a substituted or unsubstituted linear or branched $C_2$-$C_{60}$ alkyl group. The detailed description of $R_1$ in the specification may be referred to as descriptions of $R_{1x}$ and $R_{1y}$.

In Formula 1(1), $X_{1x}$ may be one of N and C($R_{3x}$), and $X_{1y}$ may be one of N and C($R_{3y}$).

In Formula 1(1), $R_{2x}$ to $R_{4x}$ and $R_{2y}$ to $R_{4y}$ are each independently selected from among a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —N($Q_1$)($Q_2$), —Si($Q_3$)($Q_4$)($Q_5$), —C(=O)($Q_6$) (where $Q_1$ to $Q_6$ are each independently one of a hydrogen atom, a substituted or unsubstituted $C_1$-$C_{60}$ alkyl group, a substituted or unsubstituted $C_6$-$C_{60}$ aryl group, and a substituted or unsubstituted $C_2$-$C_{60}$ heteroaryl group), and a binding site of an adjacent ligand via a single bond or a divalent linking group, $R_3$ and $R_4$ being optionally linked to each other to form one of a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, and a substituted or unsubstituted $C_2$-$C_{20}$ heteroaromatic group. The detailed description of $R_2$ in the specification may be referred to as descriptions of $R_{2x}$ to $R_{4x}$ and $R_{2y}$ to $R_{4y}$.

In Formula 1(1), $a_x$ and $a_y$ may be each independently an integer from 1 to 10. The detailed description of a in the specification may be referred to as descriptions of $a_x$ and $a_y$.

The organometallic compound of Formula 1 above may be a compound represented by one of Formulae 1A to 1R:

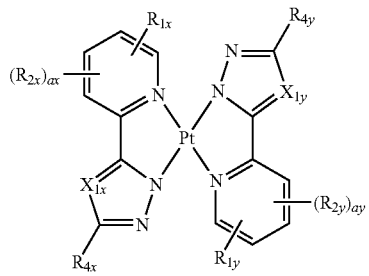

<Formula 1A>

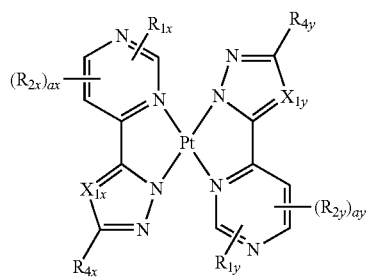

<Formula 1B>

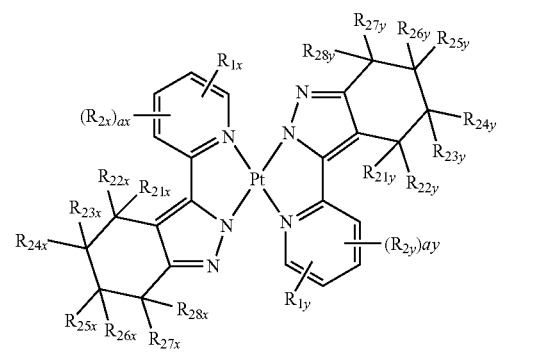

<Formula 1C>

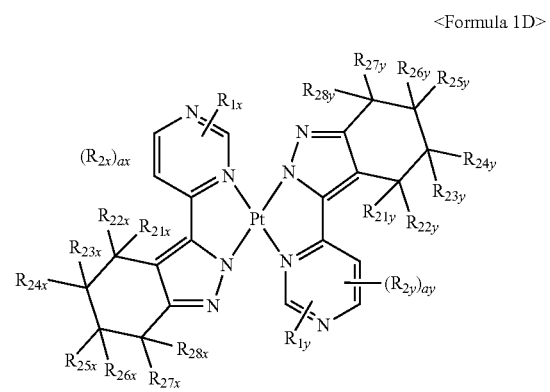

<Formula 1D>

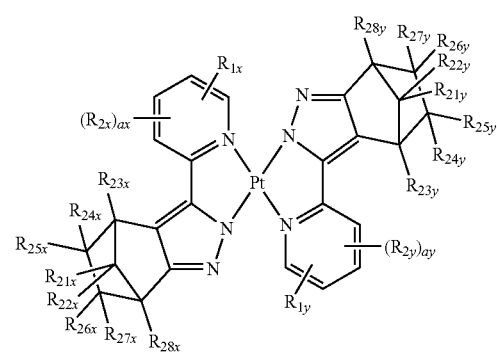

<Formula 1E>

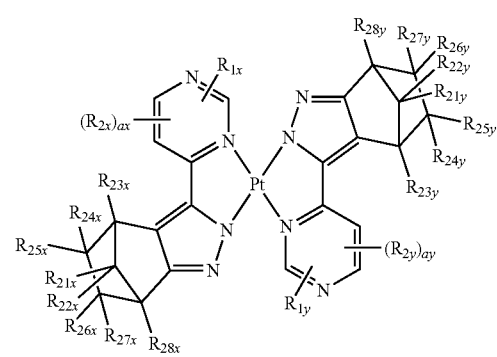

<Formula 1F>

<Formula 1G>
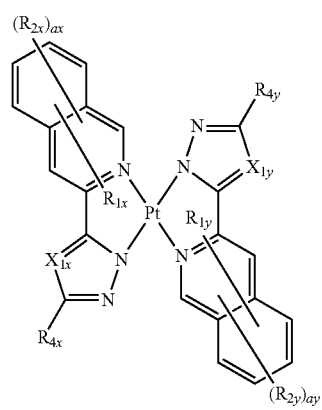
<Formula 1H>
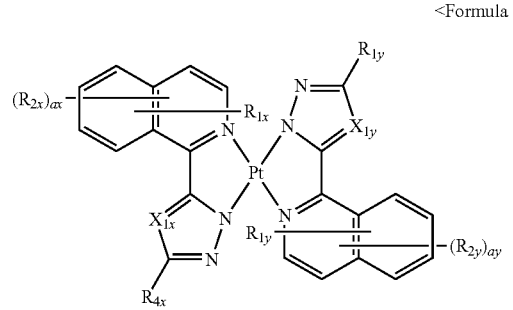
<Formula 1I>
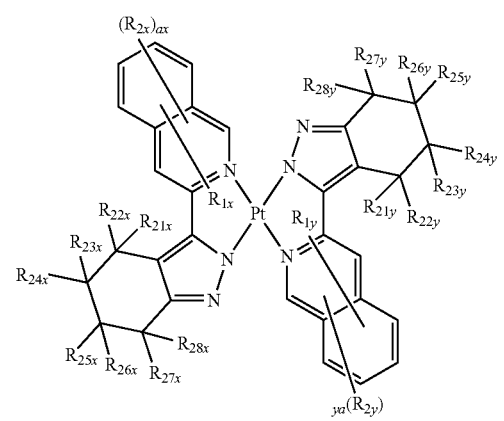
<Formula 1K>
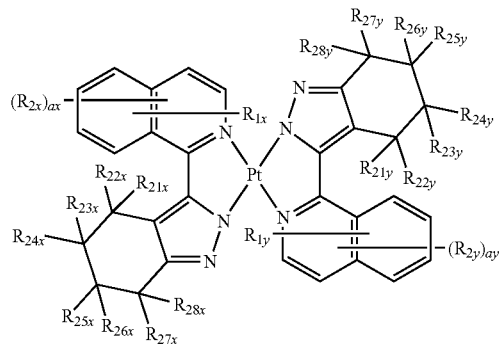
<Formula 1L>
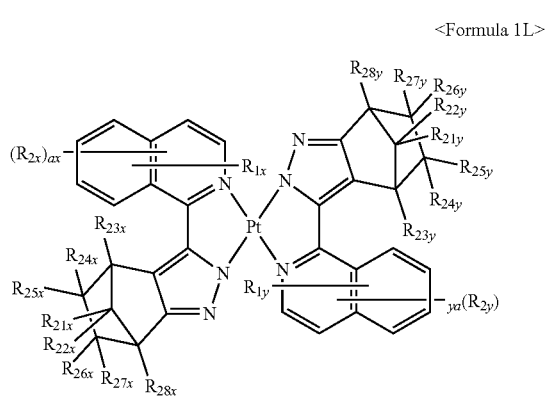
<Formula 1M>
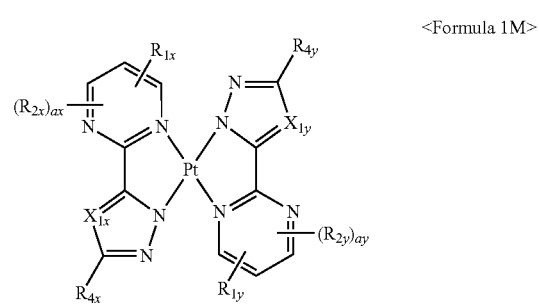
<Formula 1N>
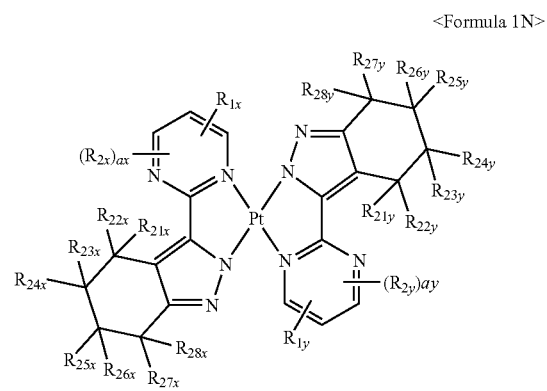

-continued

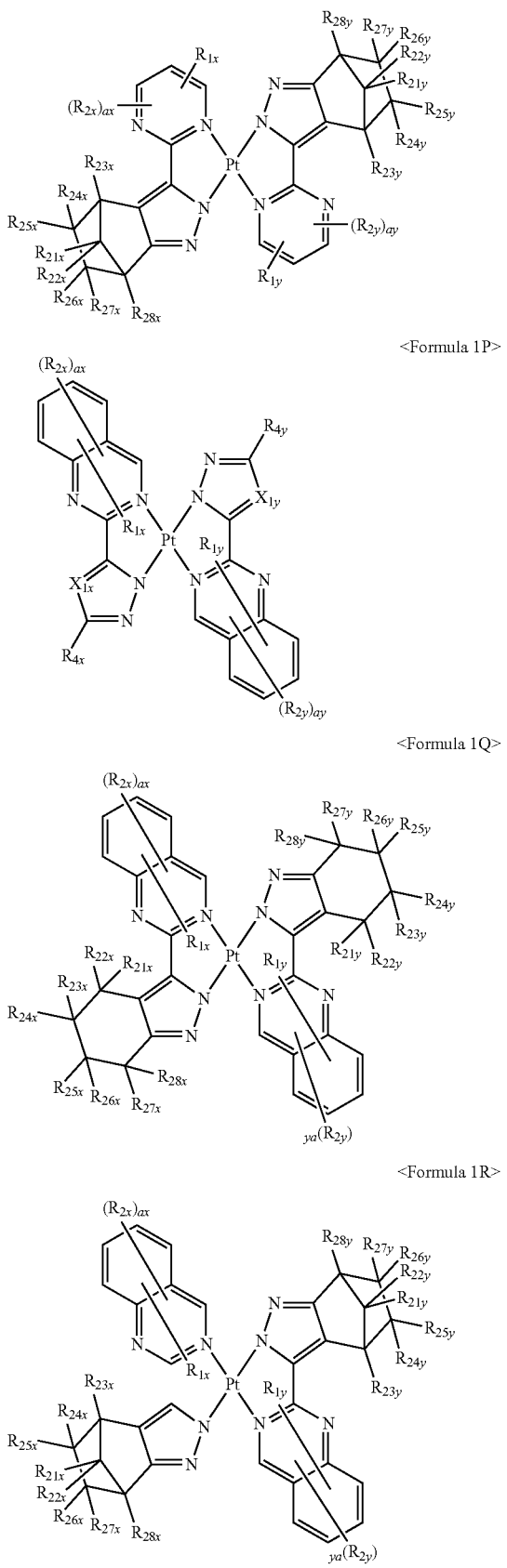

<Formula 1O>

<Formula 1P>

<Formula 1Q>

<Formula 1R>

The detailed descriptions of substituents in the specification may be referred to as descriptions of the substituents in Formulae 1A to 1R.

In some embodiments, in Formulae 1A to 1R, $X_{1x}$ may be one of N and $C(R_{3x})$, $X_{1y}$ may be one of N and $C(R_{3y})$, $R_{1x}$ and $R_{1y}$ may be each independently one selected from among:

an ethyl group, a n-propyl group, an i-propyl group, a n-butyl group, an i-butyl group, a t-butyl group, a pentyl group, a hexyl group, a heptyl group, an octyl group, a nonyl group, and a decyl group; and an ethyl group, a n-propyl group, an i-propyl group, a n-butyl group, an i-butyl group, a t-butyl group, a pentyl group, a hexyl group, a heptyl group, an octyl group, a nonyl group, and a decyl group, each substituted with at least one of a deuterium atom, —F, a hydroxyl group, a cyano group, a nitro group, and an amino group, $R_{2x}$ to $R_{4x}$, $R_{21x}$ to $R_{28x}$, $R_{2y}$ to $R_{4y}$, and $R_{21y}$ to $R_{28y}$ may be each independently one selected from among, a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phoshoric acid group or a salt thereof;

a methyl group, an ethyl group, n-propyl group, i-propyl group, n-butyl group, i-butyl group, t-butyl group, a pentyl group, a hexyl group, a heptyl group, an octyl group, a nonyl group, a decyl group, a methoxy group, an ethoxy group, a propoxy group, a butoxy group, and a pentoxy group; and a methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, each substituted with at least one of a deuterium atom, —F, a hydroxyl group, a cyano group, a nitro group, and an amino group, and $a_x$ and $a_y$ are each independently an integer from 1 to 3.

In Formulae 1A to 1R, n may be 2 and m may be 0. Alternatively, n may be 1 and m may be 1.

For example, in Formula 1, n may be 2, the two ligands represented by

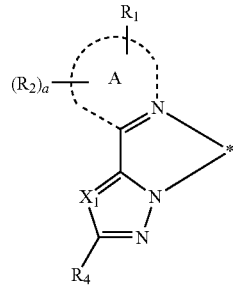

may be identical to or different from each other. The organometallic compound of Formula 1 may be in trans form.

For example, two ligands in Formula 1(1) may be the same.

In some other embodiments, two ligands in each of Formulae 1A to 1R may be the same.

In some embodiments, the organometallic compound of Formula 1 above may be a compound represented by one of Formulae 1A(1), 1A(2), 1A(3), 1B(1), 1C(1), 1D(1), 1D(2), 1E(1), 1F(1), 1G(1), 1H(1), 1J(1), 1M(1), 1M(2), 1N(1), 1N(2), 1O(1), 1P(1), and 1S(1) below, but not limited thereto:
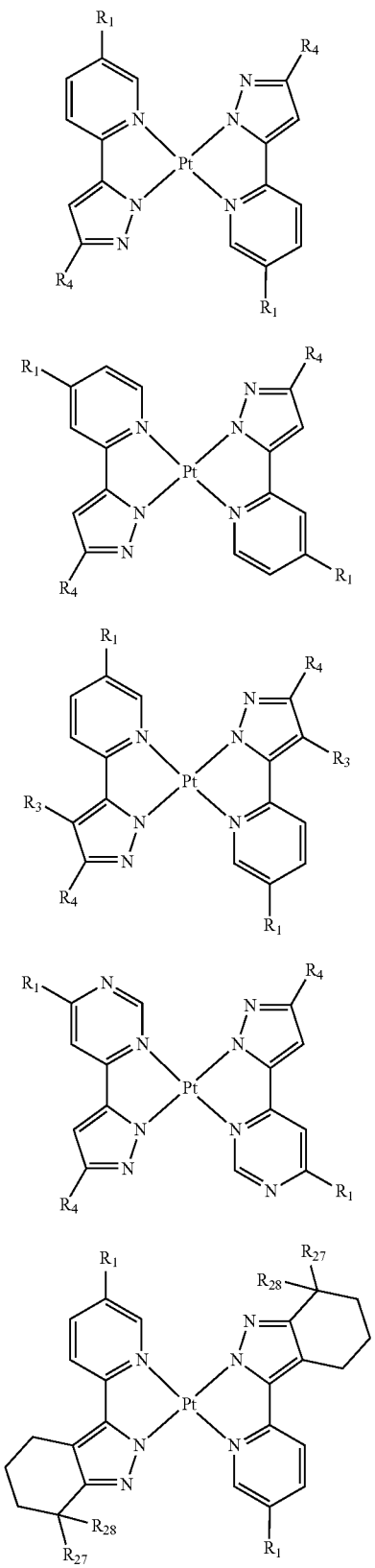
<Formula 1A(1)>
<Formula 1A(2)>
<Formula 1A(3)>
<Formula 1B(1)>
<Formula 1C(1)>
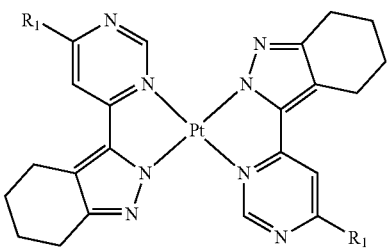
<Formula 1D(1)>
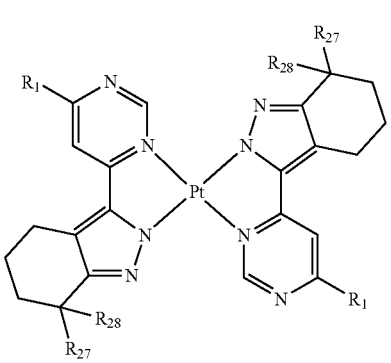
<Formula 1D(2)>
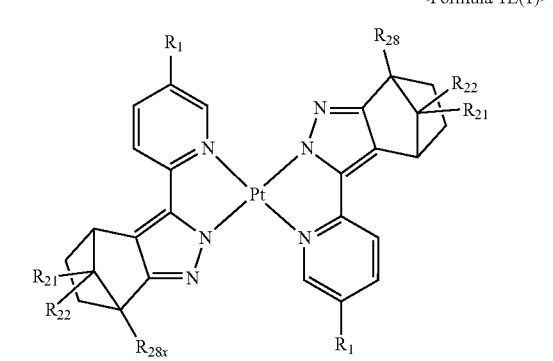
<Formula 1E(1)>
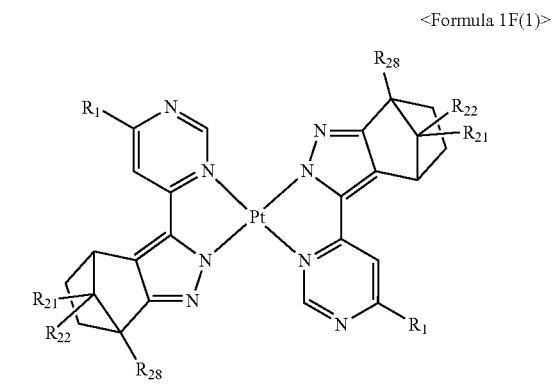
<Formula 1F(1)>

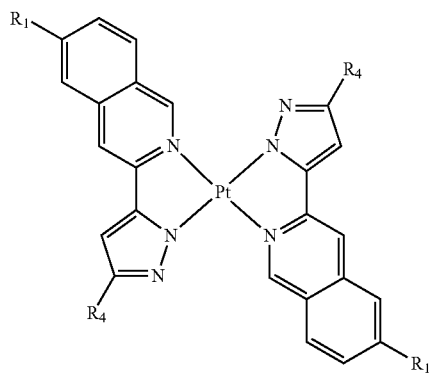
<Formula 1G(1)>
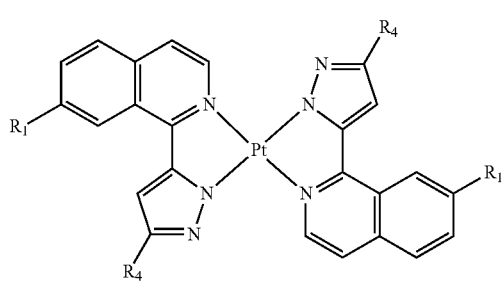
<Formula 1H(1)>
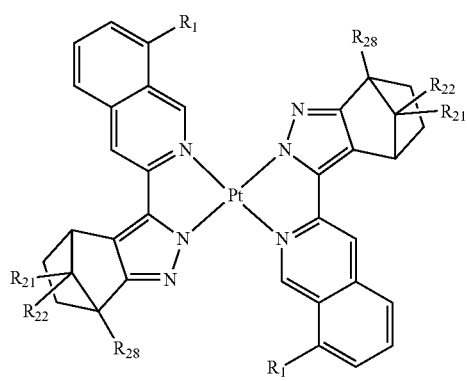
<Formula 1J(1)>
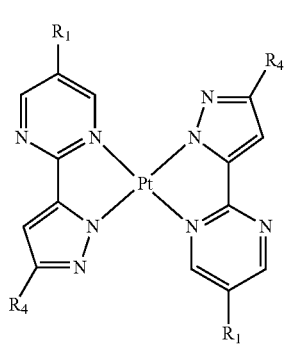
<Formula 1M(1)>
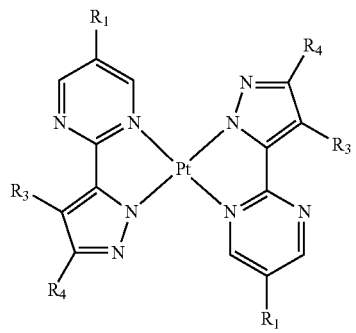
<Formula 1M(2)>
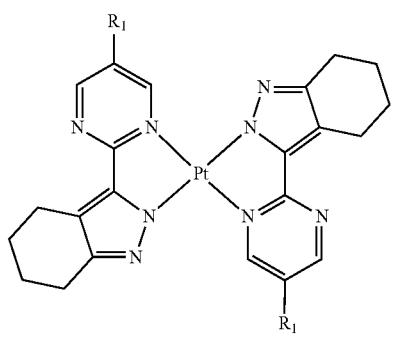
<Formula 1N(1)>
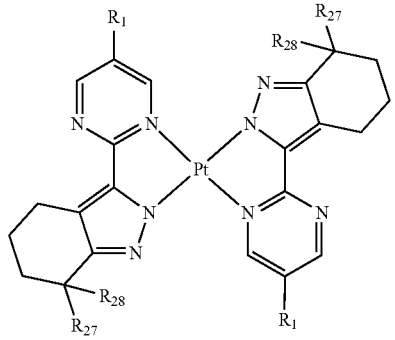
<Formula 1N(2)>
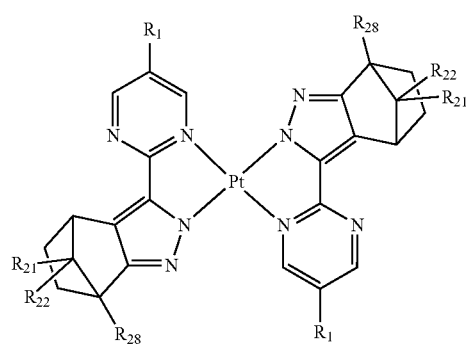
<Formula 1O(1)>

<Formula 1P(1)>

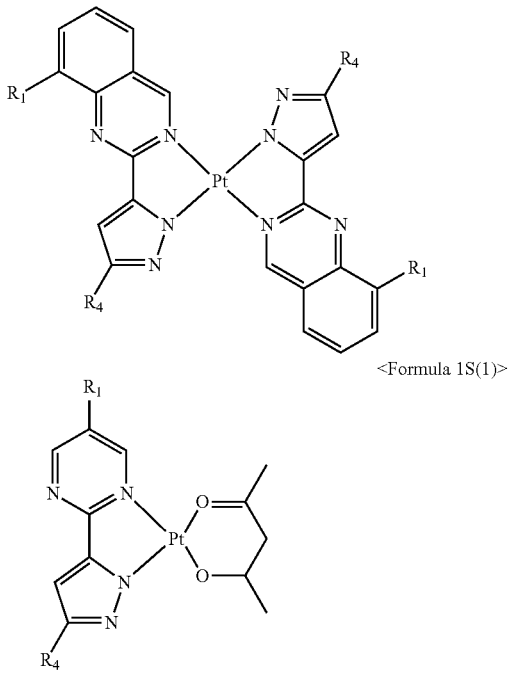

<Formula 1S(1)>

The detailed descriptions of substituents in the specification may be referred to as description of $R_1$, $R_3$, $R_4$, $R_{21}$, $R_{22}$, $R_{27}$, and $R_{28}$ in Formulae 1A(1), 1A(2), 1A(3), 1B(1), 1C(1), 1D(1), 1D(2), 1E(1), 1F(1), 1G(1), 1H(1), 1J(1), 1M(1), 1M(2), 1N(1), 1N(2), 1O(1), 1P(1), and 1S(1).

For example, in Formulae 1A(1), 1A(2), 1A(3), 1B(1), 1C(1), 1D(1), 1D(2), 1E(1), 1F(1), 1G(1), 1H(1), 1J(1), 1M(1), 1M(2), 1N(1), 1N(2), 1O(1), 1P(1), and 1S(1), $R_1$ may be one selected from among:

an ethyl group, a n-propyl group, an i-propyl group, a n-butyl group, an i-butyl group, a t-butyl group, a pentyl group, a hexyl group, a heptyl group, an octyl group, a nonyl group, and a decyl group; and an ethyl group, a n-propyl group, an i-propyl group, a n-butyl group, an i-butyl group, a t-butyl group, a pentyl group, a hexyl group, a heptyl group, an octyl group, a nonyl group, and a decyl group, each substituted with at least one of a deuterium atom, —F, a hydroxyl group, a cyano group, a nitro group, and an amino group, and $R_3$, $R_4$, $R_{21}$, $R_{22}$, $R_{27}$, and $R_{28}$ may be each independently one selected from among, a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phoshoric acid group or a salt thereof;

a methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, a methoxy group, an ethoxy group, propoxy group, a butoxy group, and a pentoxy group; and a methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, each substituted with at least one of a deuterium atom, —F, a hydroxyl group, a cyano group, a nitro group, and an amino group.

In some other embodiments, the organometallic compound of Formula 1 may be one of Compounds 1 to 35 below, but it is not limited thereto:

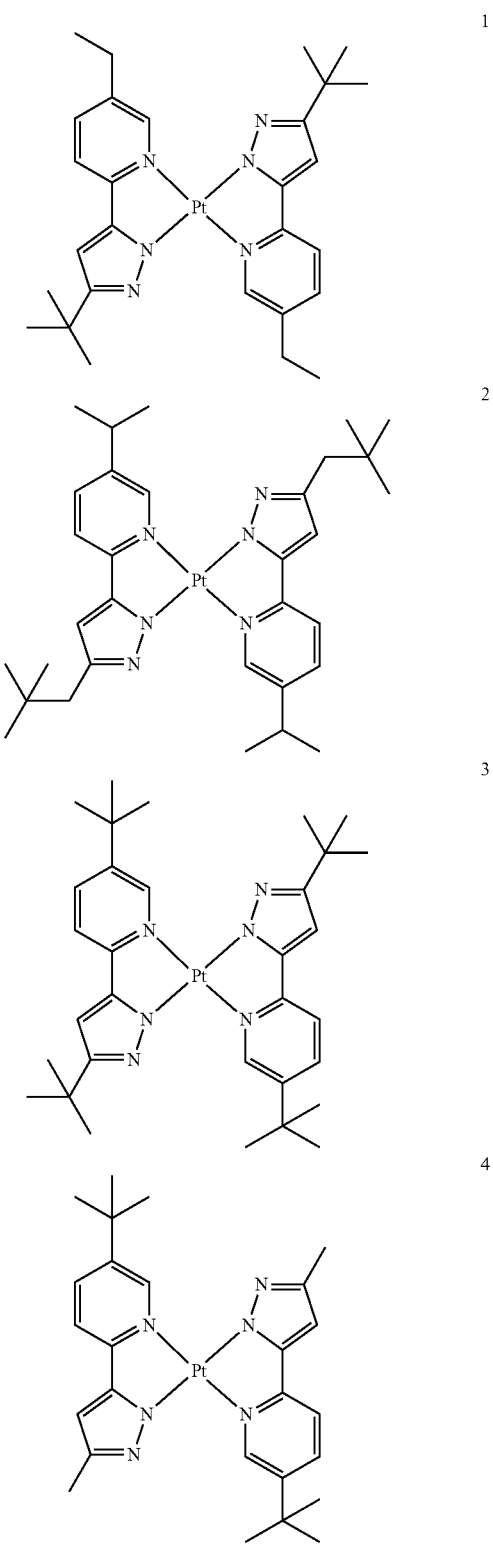

5
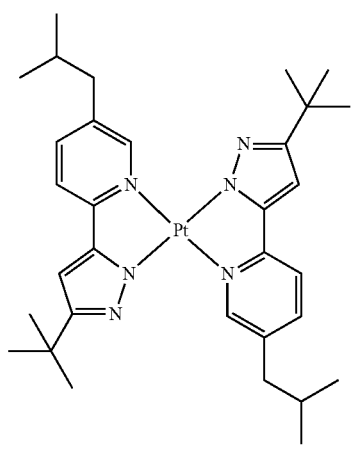
6
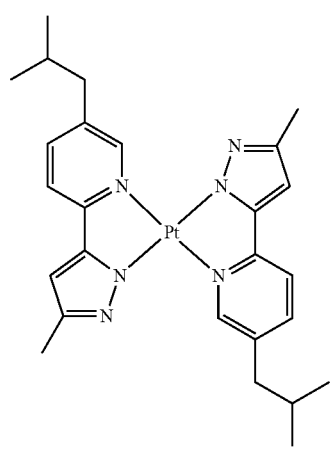
7
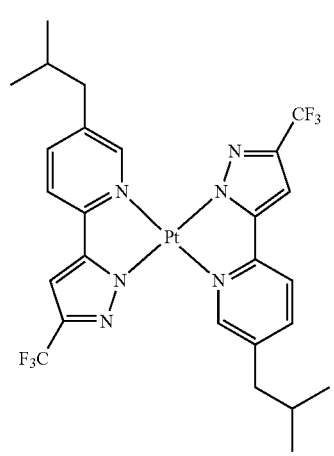
8
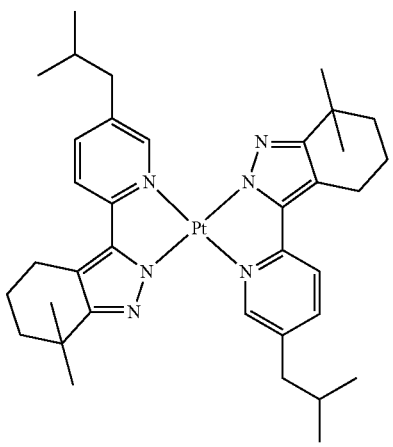
9
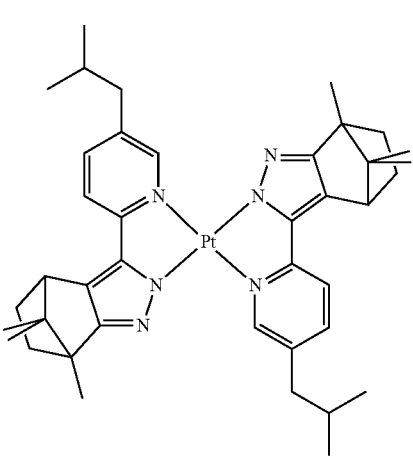
10
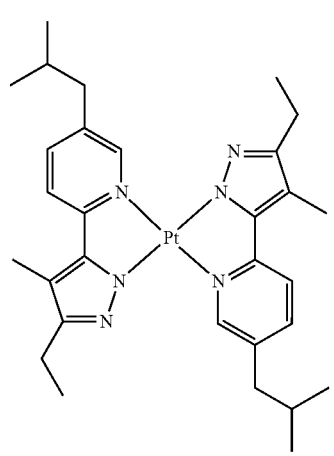

11
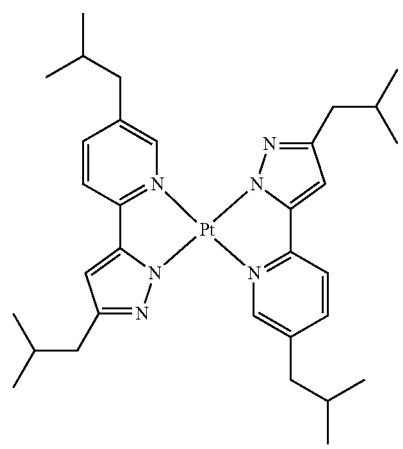
12
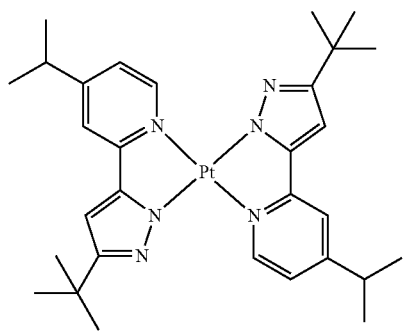
13
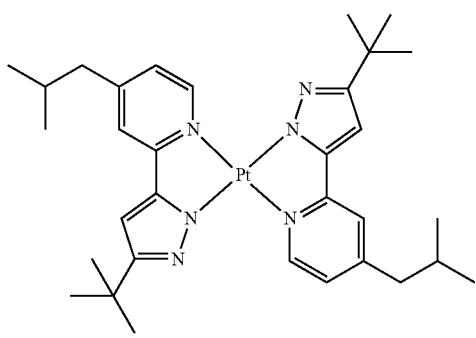
14
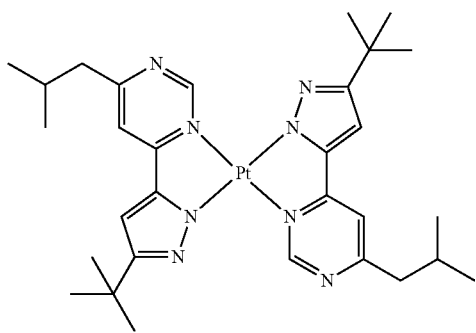
15
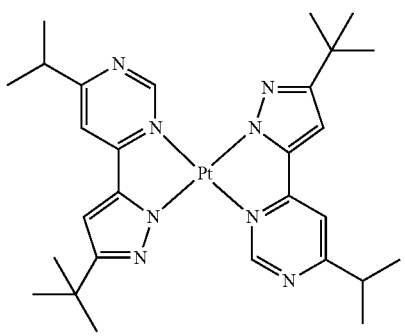
16
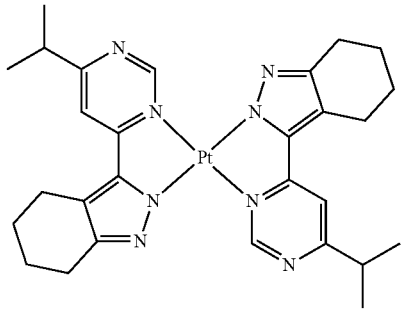
17
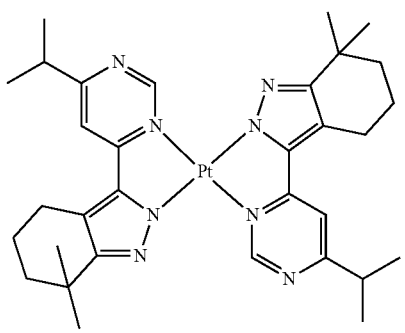
18
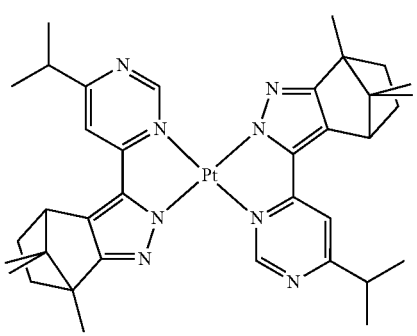
19
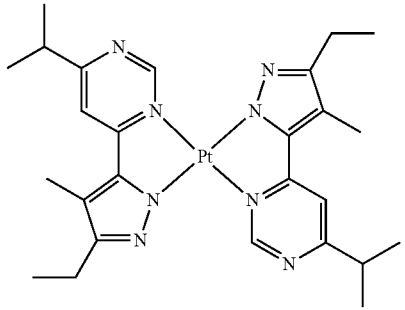

20
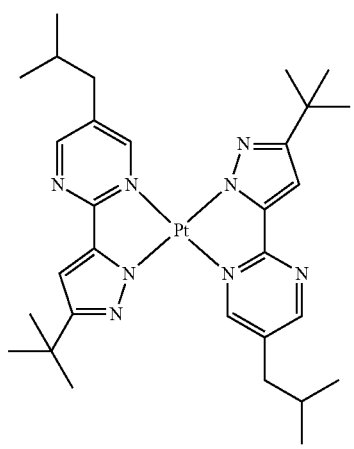
21
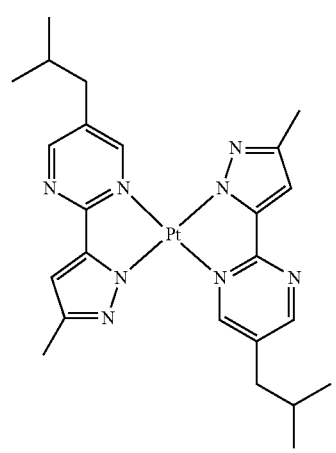
22
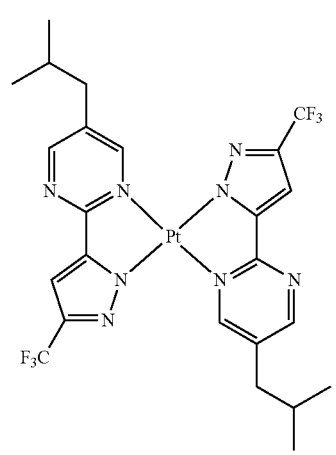
23
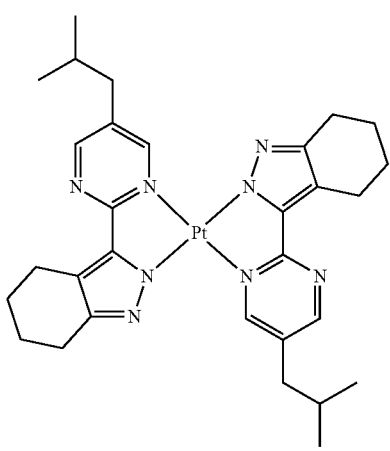
24
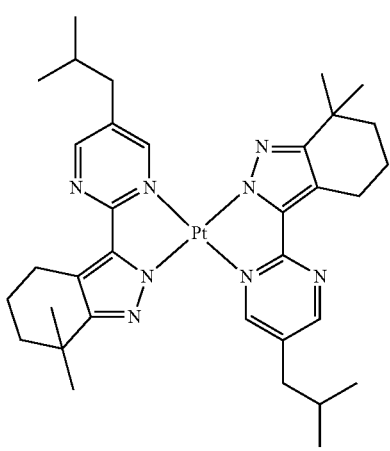
25
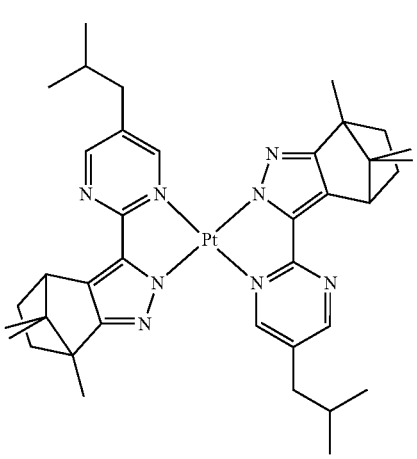

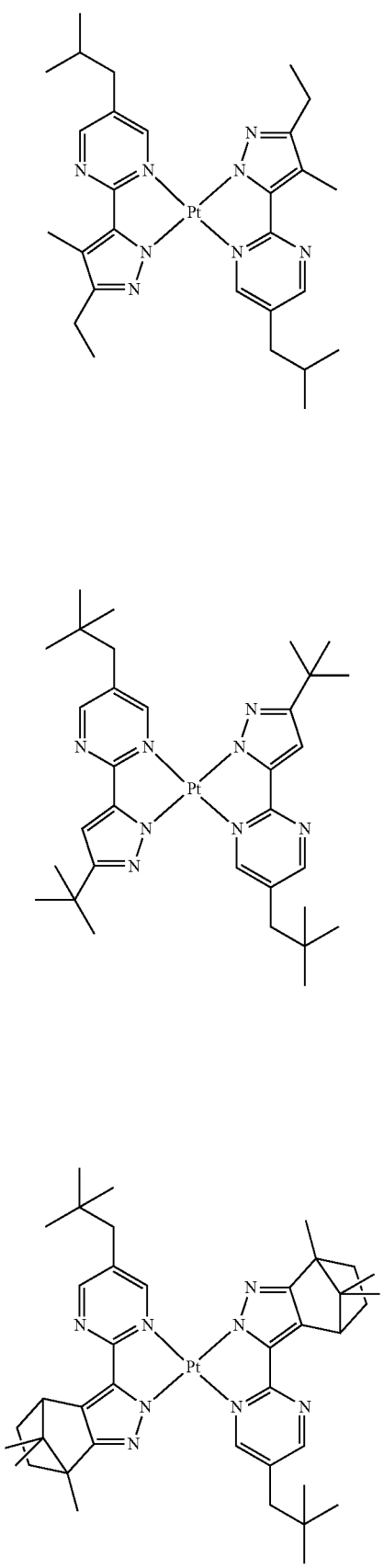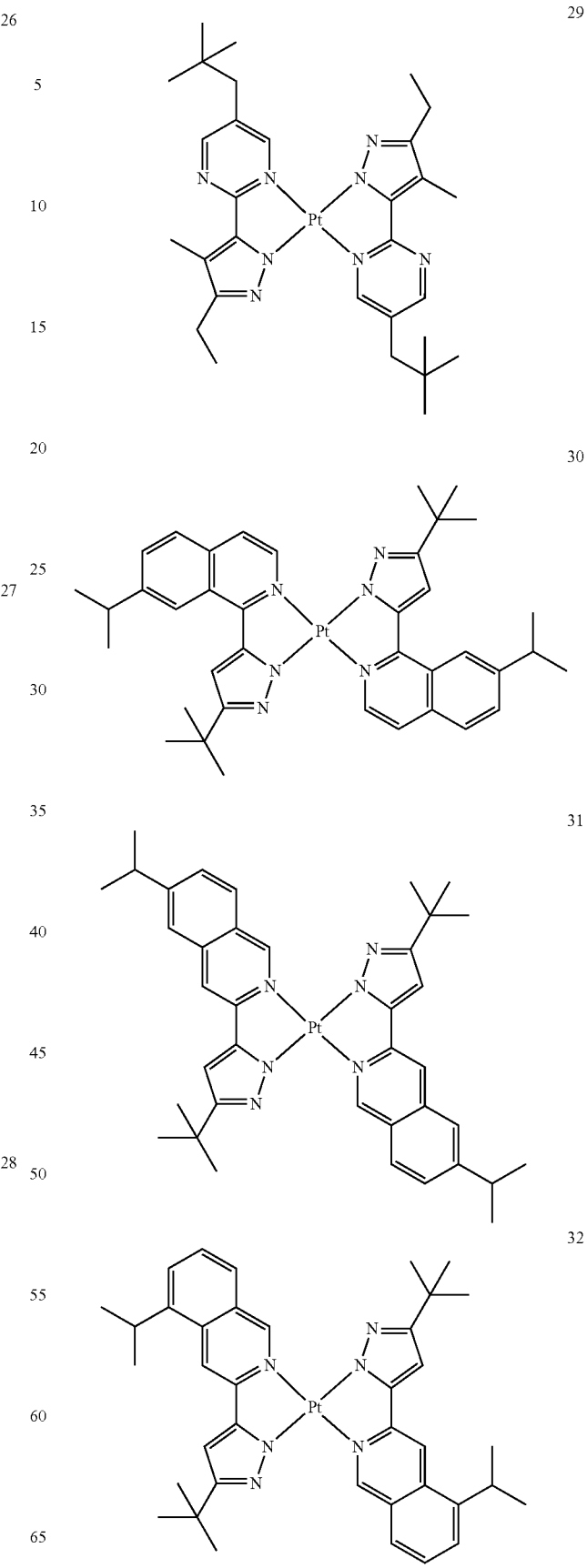

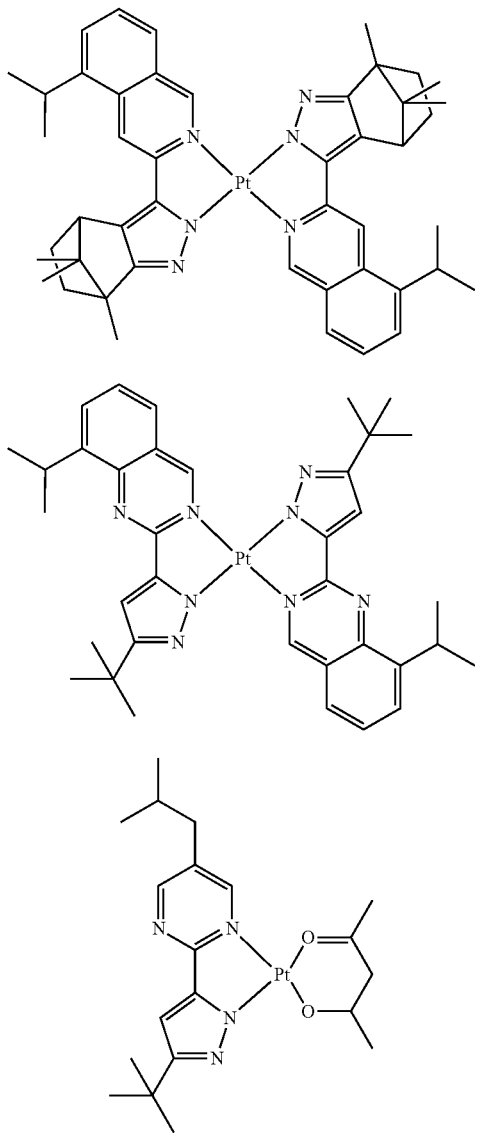

In the organometallic compound of Formula 1 above, $R_1$ as an alkyl group having at least "two" carbon atoms serves as an essential substituent of the A ring, molecular agglomeration in the organometallic compound may be reduced or substantially prevented. As a result, an organic light-emitting diode including the organometallic compound of Formula 1 above may have a high light-emitting efficiency.

Because the organometallic compound of Formula 1 above has high thermal stability, an organic light-emitting diode including the organometallic compound may have a low driving voltage, a high luminance, a high efficiency and a long lifetime.

The organometallic compound of Formula 1 may be synthesized using a known organic synthesis method. A synthesis method of the organometallic compound of Formula 1 may be understood by those of ordinary skill in the art from the examples that will be described below.

The organometallic compound of Formula 1 may be used between a pair of electrodes of an organic light-emitting diode, for example, in an emission layer of an organic light-emitting diode.

According to another embodiment of the present invention, an organic light-emitting diode includes a first electrode, a second electrode disposed opposite to the first electrode, and an organic layer disposed between the first electrode and the second electrode, the first layer including the organometallic compound of Formula 1 described above.

As used herein, "(for example, the organic layer) including at least one organometallic compound" means "(the organic layer) including one of the organometallic compounds of Formula 1 above, or at least two different organometallic compounds of Formula 1 above".

The organic layer may include at least one layer selected from among a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

The term "organic layer" as used herein refers to a single layer and/or a plurality of layers disposed between the first and second electrodes of the organic light-emitting diode.

The organic layer may include an emission layer, and the emission layer may include the organometallic compound of Formula 1 described above. The emission layer including the organometallic compound may emit light based on the mechanism of phosphorescence.

In some embodiments, the organometallic compound in the emission layer of the organic light-emitting diode may serve as a dopant. The emission layer may further include a carbazole-based compound as a host.

For example, the carbazole-based compound available as the host of the emission layer may be a compound represented by Formula 10 below, but is not limited thereto:

<Formula 10>

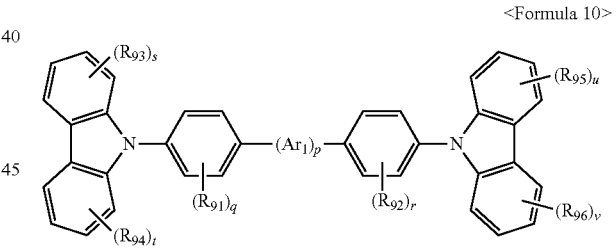

In Formula 10, $Ar_1$ may be one selected from among a substituted or unsubstituted $C_1$-$C_{60}$ alkylene group, a substituted or unsubstituted $C_2$-$C_{60}$ alkenylene group, —C(=O)—, —N($R_{100}$)— (where $R_{100}$ is one of a substituted or unsubstituted $C_6$-$C_{60}$ aryl group and a substituted or unsubstituted $C_2$-$C_{60}$ heteroaryl group), a substituted or unsubstituted $C_6$-$C_{60}$ arylene group, and a substituted or unsubstituted $C_2$-$C_{60}$ heteroarylene group, p may be an integer from 0 to 10, $R_{91}$ to $R_{96}$ may be each independently selected from among a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, and a substituted or unsubstituted $C_2$-$C_{60}$ heteroaryl group, two adjacent substituents of $R_{91}$ to $R_{96}$ being optionally linked to each other to form a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, or a substituted or unsubstituted $C_2$-$C_{20}$ heteroaromatic group; and q, r, s, t, u, and v may be each independently an integer from 1 to 4.

In some other embodiments, in Formula 10, $Ar_1$ may be one of a $C_1$-$C_5$ alkylene group, a $C_2$-$C_5$ alkenylene group, —C(=O)—, and —N($R_{100}$)—, where $R_{100}$ may be one selected from among:

a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group, each substituted with at least one of a deuterium atom, a halogen atom, a hydroxyl group, a cyano group, a nitro group, an amino group, $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group.

In Formula 10 above, $R_{91}$ to $R_{96}$ may be each independently one selected from among a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group; and a $C_1$-$C_{20}$ alkyl group, and a $C_1$-$C_{20}$ alkoxy group, each substituted with at least one of a deuterium atom, a halogen atom, a hydroxyl group, a cyano group, a nitro group, and an amino group.

For example, the carbazole-based compound may be one of Compounds H1 to H30 below, but is not limited thereto:

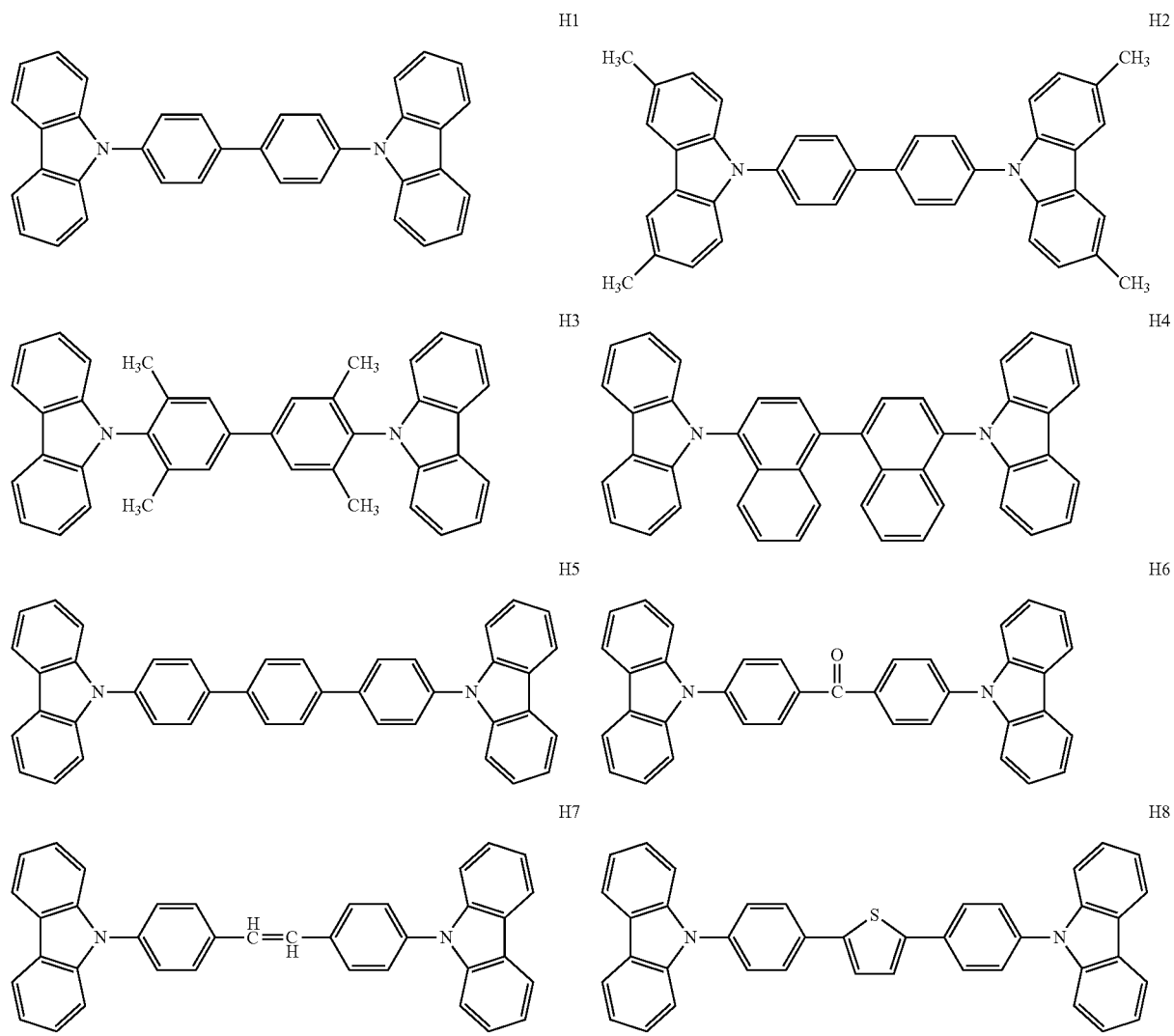

-continued
H9
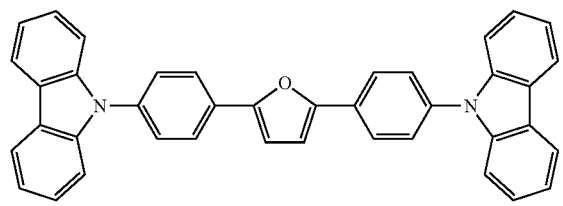
H10
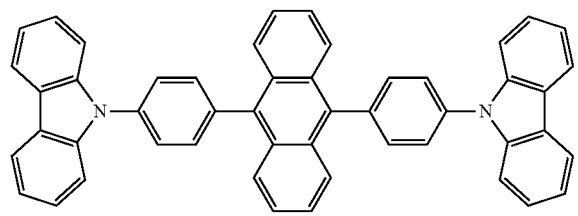
H11
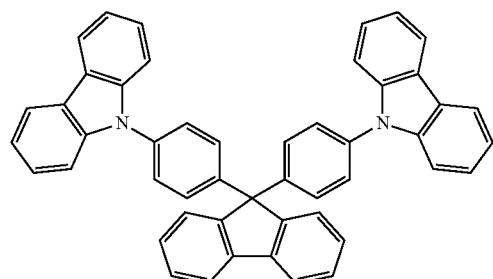
H12
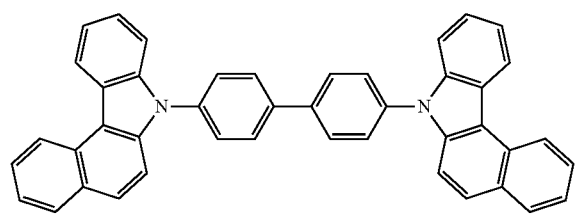
H13
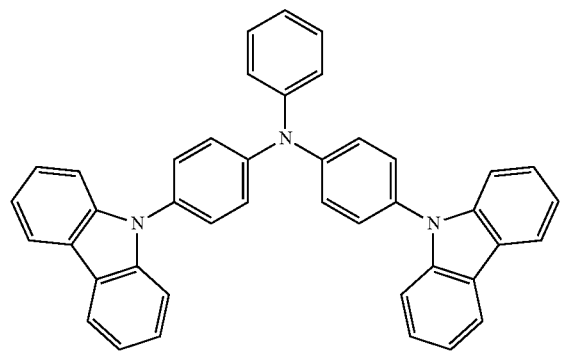
H14
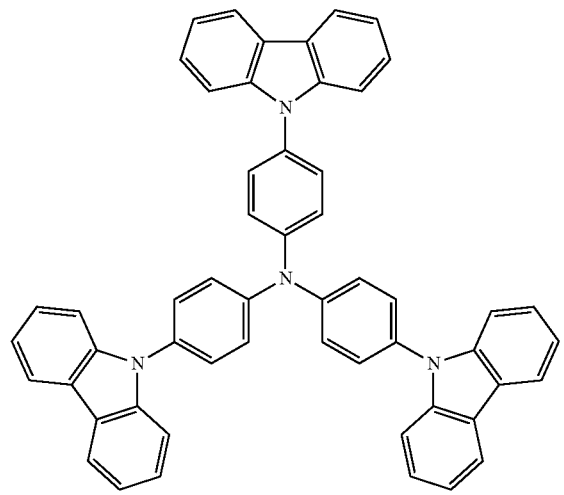
H15
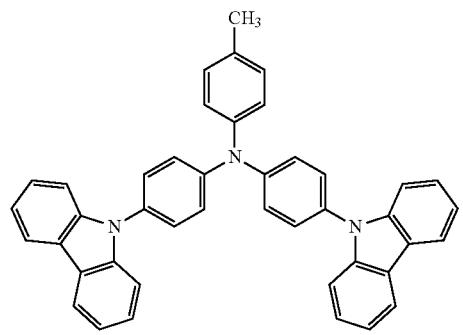
H16
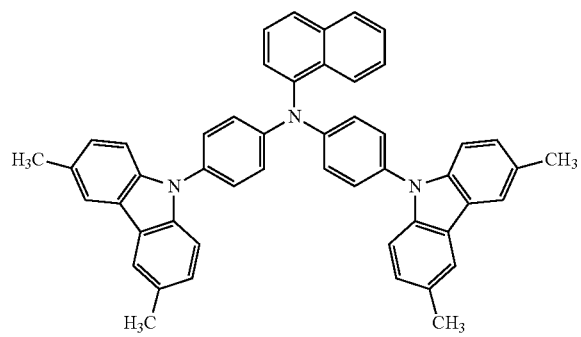

-continued
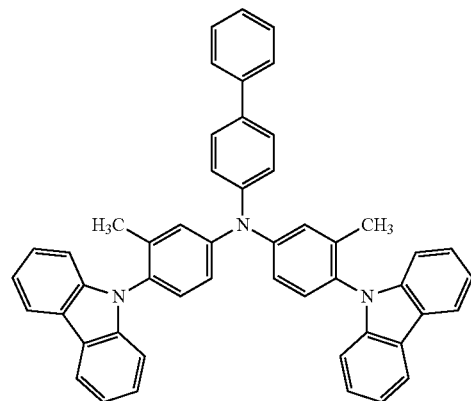
H17
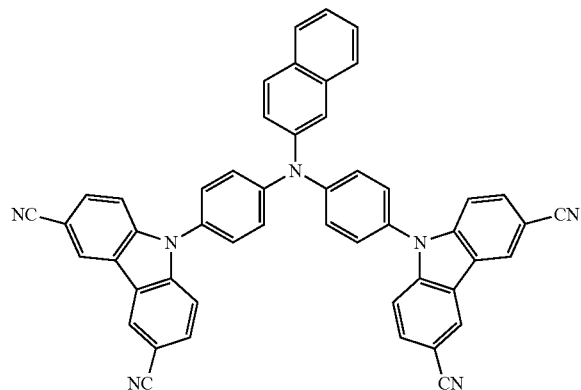
H18
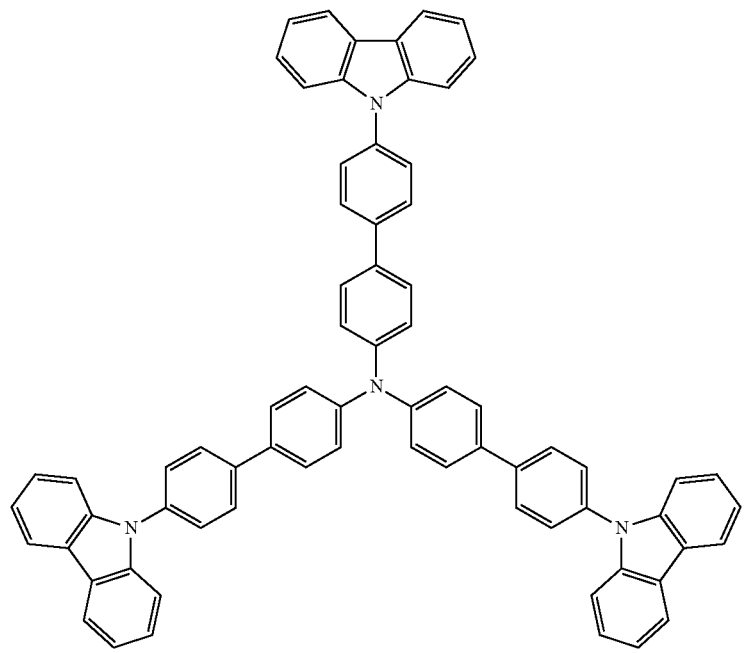
H19
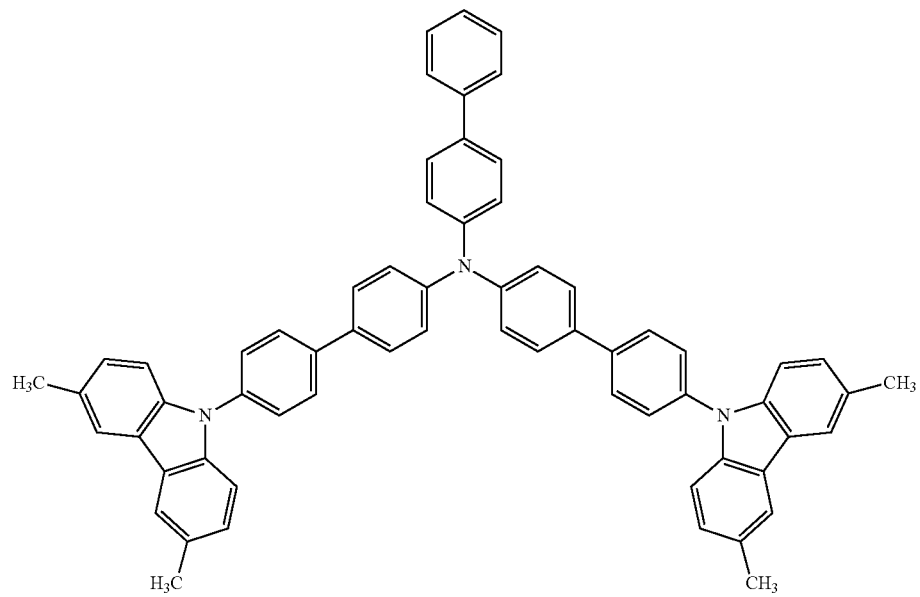
H20

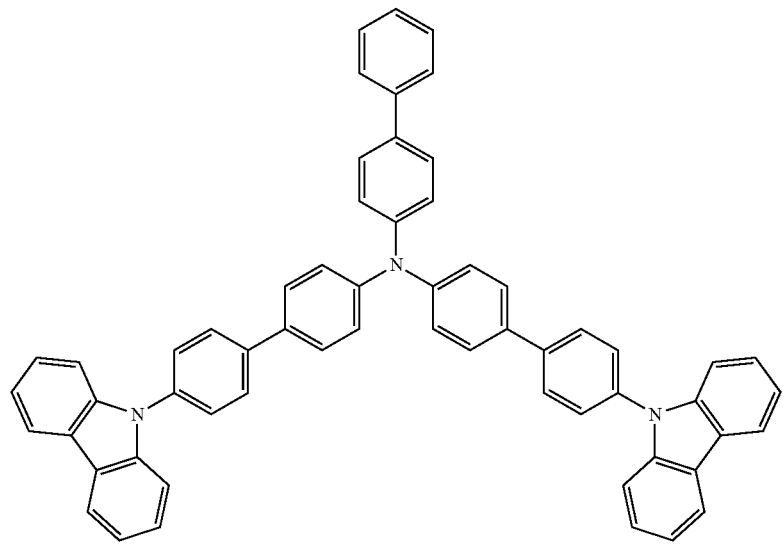
H21
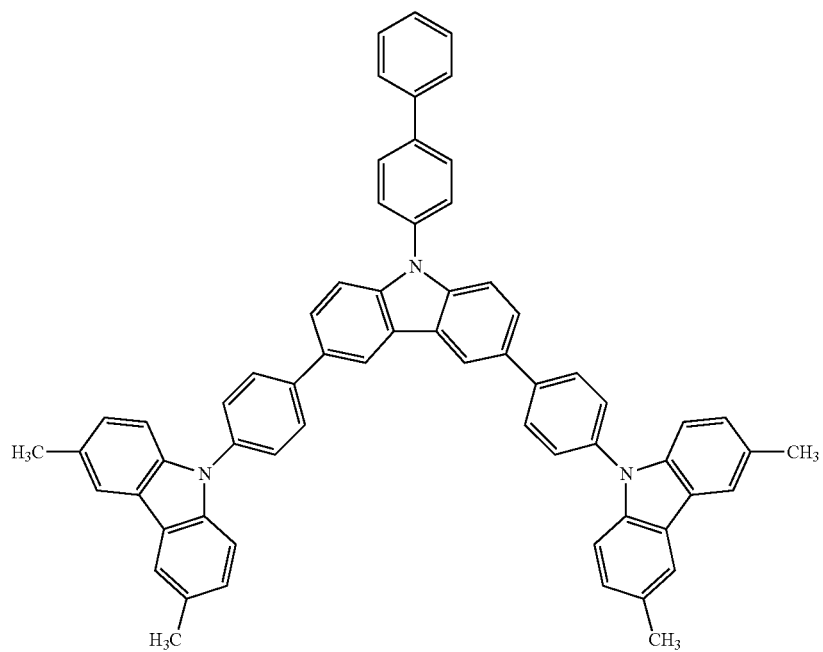
H22
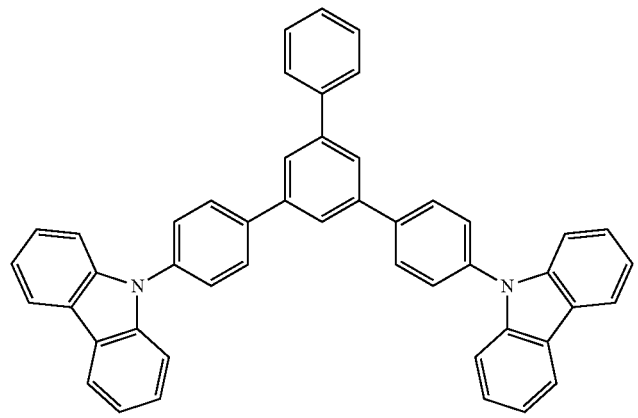
H23

-continued
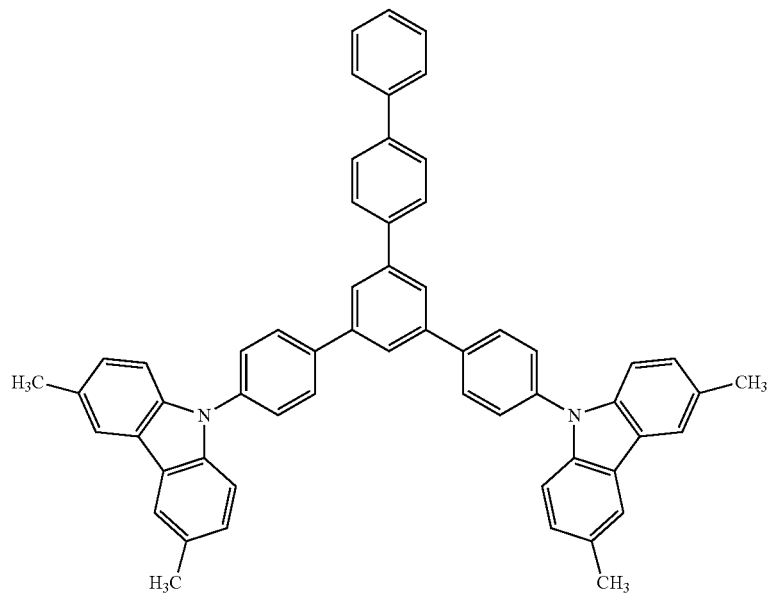
H24
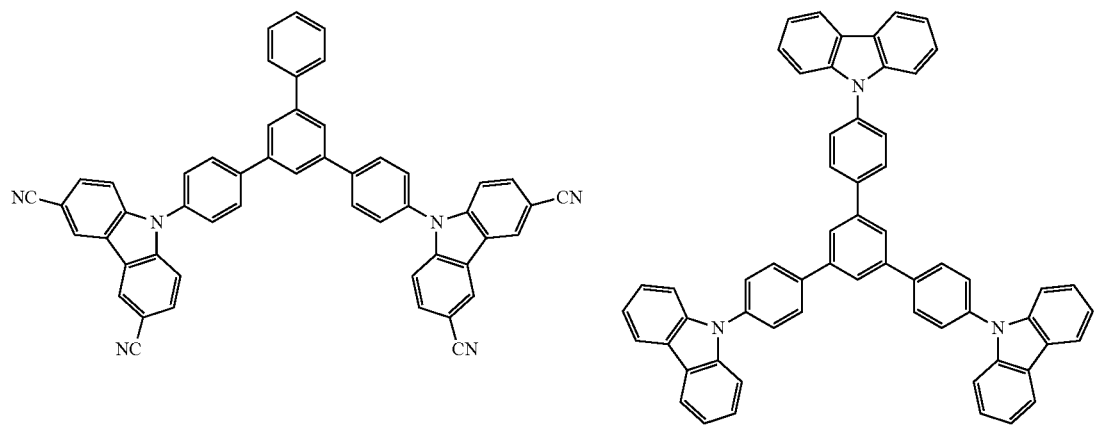
H25
H26
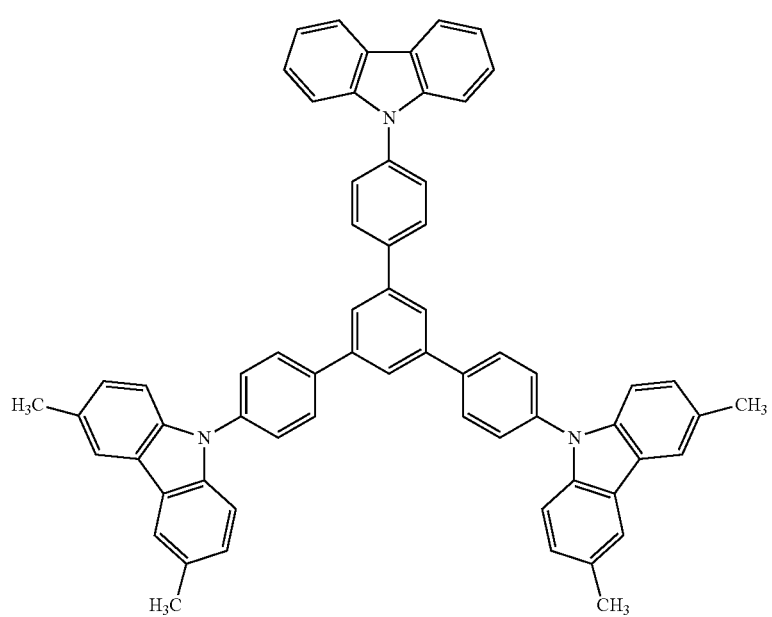
H27

-continued

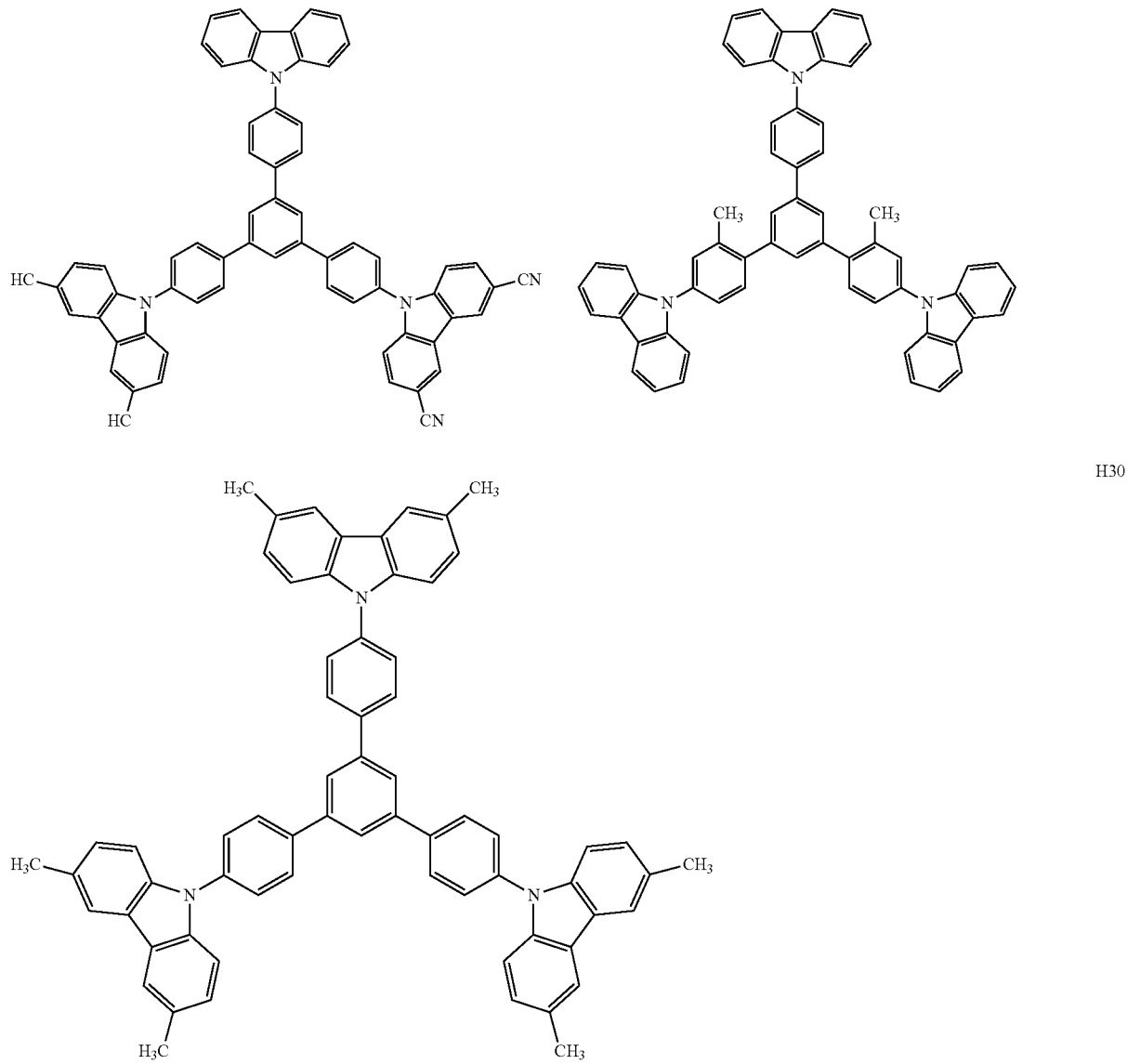

Hereinafter, a structure of an organic light-emitting diode according to an embodiment of the present invention and a method of manufacturing the same will now be described with reference to the FIGURE. The FIGURE is a schematic sectional view of an organic light-emitting diode 10 according to an embodiment of the present invention.

Referring to the FIGURE, the organic light emitting diode 10 has a structure including a substrate 11, a first electrode 13, an organic layer 15, and a second electrode 17 that are sequentially stacked on one another.

The substrate 11 may be any substrate that is used in existing organic light-emitting diodes. In some embodiments, the substrate 11 may be a glass substrate or a transparent plastic substrate with strong mechanical strength, thermal stability, transparency, surface smoothness, ease of handling and water resistance.

The first electrode 13 may be formed by depositing or sputtering a first electrode-forming material on the substrate 11. When the first electrode 13 is an anode, a material having a high work function may be used as the first electrode-forming material to facilitate hole injection. The first electrode 13 may be a reflective electrode or a transmissive electrode. Transparent and conductive materials such as indium tin oxide (ITO), indium zinc oxide (IZO), $SnO_2$, and ZnO may be used to form the first electrode. The first electrode 13 may be formed as a reflective electrode using one of magnesium (Mg), aluminum (Al), aluminum-lithium (Al—Li), calcium (Ca), magnesium-indium (Mg—In), magnesium-silver (Mg—Ag), and the like.

The first electrode 13 may have a single-layer structure or a multi-layer structure including at least two layers. For example, the first electrode 13 may have a three-layered structure of ITO/Ag/ITO, but it is not limited thereto.

The organic layer 15 may be disposed on the first electrode 13.

The organic layer 15 may include a hole injection layer (HIL), a hole transport layer (HTL), a buffer layer, an emission layer (EML), an electron transport layer (ETL), and an electron injection layer (EIL).

The HIL may be formed on the first electrode 13 by one of vacuum deposition, spin coating, casting, Langmuir-Blodgett (LB) deposition, and the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of from about 100° C. to about 500° C., a pressure of from about $10^{-8}$ torr to about $10^{-3}$ torr, and a deposition rate of from about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in the range of from about 2000 rpm to about 5000 rpm, and a temperature at which heat treatment is performed to remove a solvent after coating may be in the range of from about 80° C. to about 200° C. However, the coating conditions are not limited thereto.

A material for forming the HIL may be a known hole injecting material. Non-limiting examples of the hole injecting material are N,N'-diphenyl-N,N'-bis-[4-(phenyl-m-tolylamino)-phenyl]-biphenyl-4,4'-diamine (DNTPD), a phthalocyanine compound such as copper phthalocyanine, 4,4',4"-tris (3-methylphenylphenylamino)triphenylamine (m-MTDATA), 4,4',4"-tris(diphenylamino)triphenylamine (TDATA), 4,4',4"-tris(N-(naphthalene-2-yl)-N-phenylamino)triphenylamine (2-TNATA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline/poly(4-styrenesulfonate (PANI/PSS).

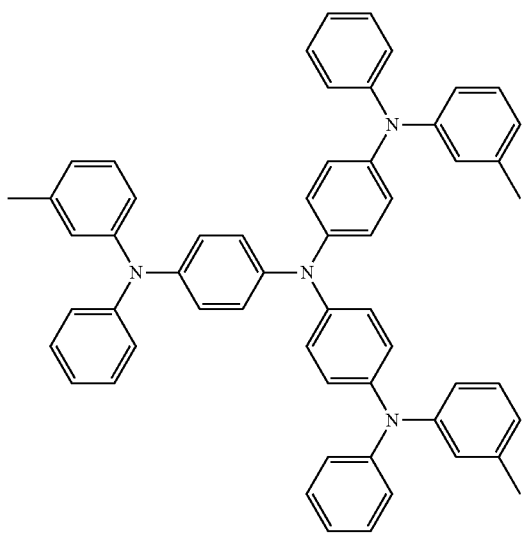

m-MTDATA

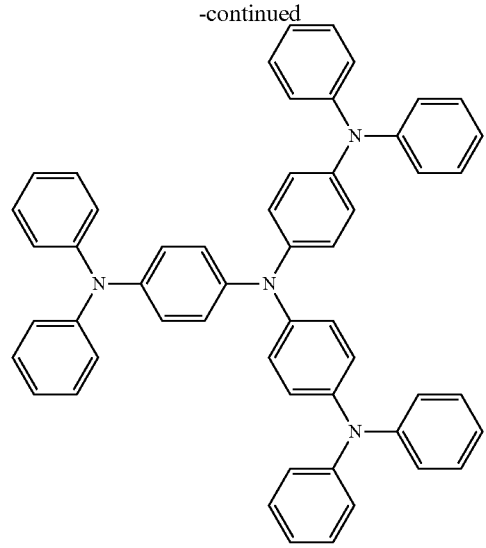

TDATA

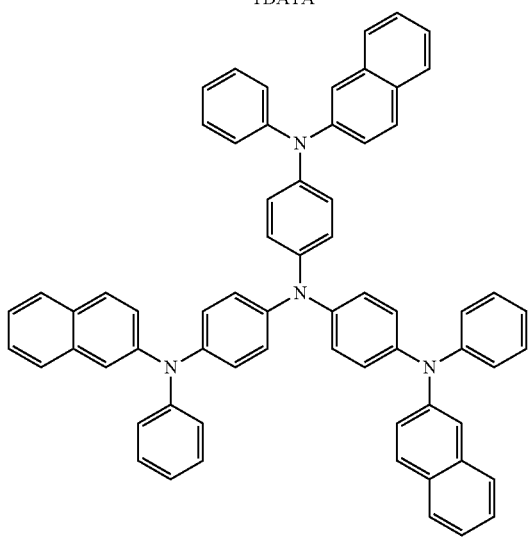

2-TNATA

The thickness of the HIL may be about 100 Å to about 10000 Å, and, in some embodiments, may be from about 100 Å to about 1000 Å. When the thickness of the HIL is within these ranges, the HIL may have good hole injecting ability without imparting a substantial increase in driving voltage to an OLED including it.

Then, a HTL may be formed on the HIL by using one of vacuum deposition, spin coating, casting, Langmuir-Blodgett (LB) deposition, and the like. When the HTL is formed using vacuum deposition or spin coating, the conditions for deposition and coating may be similar to those for the formation of the HIL, though the conditions for the deposition and coating may vary according to the material that is used to form the HTL.

Non-limiting examples of suitable HTL forming materials are carbazole derivatives, such as N-phenylcarbazole or polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine) (NPB).

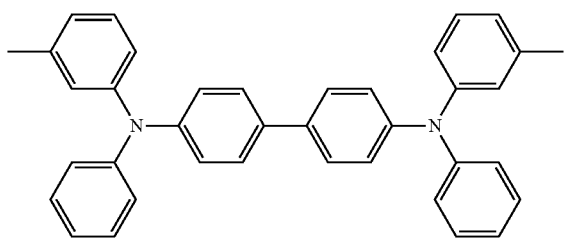

TPD

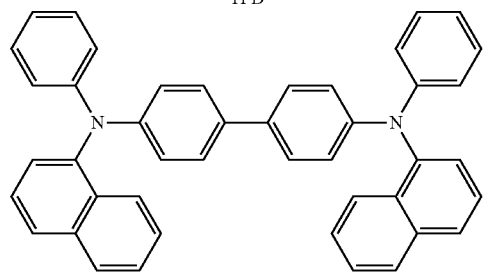

NPB

The thickness of the HTL may be from about 50 Å to about 2000 Å, and, in some embodiments, may be from about 100 Å to about 1500 Å. When the thickness of the HTL is within these ranges, the HTL may have good hole transporting ability without imparting a substantial increase in driving voltage to an OLED including it.

The H-functional layer (having both hole injection and hole transport capabilities) may contain at least one material from each group of the hole injection layer materials and hole transport layer materials. The thickness of the H-functional layer may be from about 500 Å to about 10,000 Å, and, in some embodiments, may be from about 100 Å to about 1,000 Å. When the thickness of the H-functional layer is within these ranges, the H-functional layer may have good hole injection and transport capabilities without imparting a substantial increase in driving voltage to an OLED including it.

In some embodiments, at least one of the HIL, HTL, and H-functional layer may include at least one of a compound of Formula 300 below and a compound of Formula 301 below:

<Formula 300>

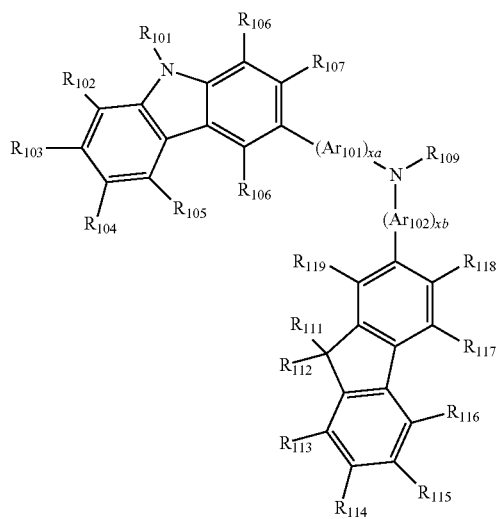

<Formula 301>

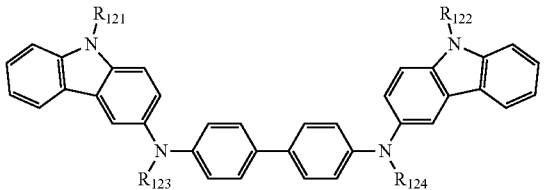

In Formula 300, $Ar_{101}$ and $Ar_{102}$ may be each independently a substituted or unsubstituted $C_6$-$C_{60}$ arylene group. In some embodiments, $Ar_{101}$ and $Ar_{102}$ may be each independently one of a phenylene group, a pentalenylene group, an indenylene group, a naphthylene group, an azulenylene group, a heptalenylene group, a substituted or unsubstituted acenaphthylene group, a fluorenylene group, a phenalenylene group, a phenanthrenylene group, an anthracenylene group, a fluoranthenylene group, a triphenylenylene group, a pyrenylenylene group, a chrysenylene group, a naphthacenylene group, a picenylene group, a perylenylene group, and a pentacenylene group; and a phenylene group, a pentalenylene group, an indenylene group, a naphthylene group, an azulenylene group, a heptalenylene group, a substituted or unsubstituted acenaphthylene group, a fluorenylene group, a phenalenylene group, a phenanthrenylene group, an anthracenylene group, a fluoranthenylene group, a triphenylenylene group, a pyrenylenylene group, a chrysenylene group, a naphthacenylene group, a picenylene group, a perylenylene group, and a pentacenylene group that are substituted with at least one of a deuterium atom, a halogen atom, a hydroxyl group, a nitro group, a cyano group, an amino group, an amidino group, hydrazine, hydrazone, a carboxyl group or salt thereof, a sulfuric acid group or salt thereof, a phosphoric acid group or salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group.

In Formula 300, xa and xb may be each independently an integer from 0 to 5, for example, may be 0, 1, or 2. For example, xa may be 1, and xb may be 0, but they are not limited thereto.

In Formulae 300 and 301 above, $R_{101}$ to $R_{108}$, $R_{111}$ to $R_{119}$, and $R_{121}$ to $R_{124}$ may be each independently one of a hydrogen atom, a deuterium atom, a halogen atom, a hydroxyl group, a cyano group, a nitro group, an amino group, an amidino group, a hydrazine group, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstiuted $C_5$-$C_{60}$ aryl group, a substituted or unsubstituted $C_5$-$C_{60}$ aryloxy group, and a substituted or unsubstituted $C_5$-$C_{60}$ arylthio group. In some embodiments, $R_{51}$ to $R_{58}$, $R_{61}$ to $R_{69}$, $R_{71}$, and $R_{72}$ may be each independently one of a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 300, $R_{109}$ may be one of a phenyl group, a naphthyl group, an anthryl group, a biphenyl group, a pyridyl group; and a phenyl group, a naphthyl group, an anthryl group, a biphenyl group, and a pyridyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In an embodiment the compound of Formula 300 may be a compound represented by Formula 300A below:

<Formula 300A>

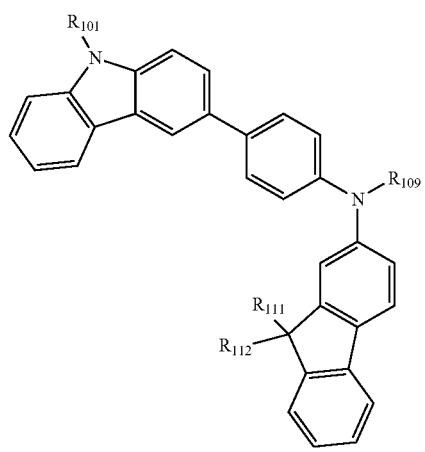

In Formula 300A, $R_{101}$, $R_{110}$, $R_{121}$, and $R_{109}$ may be as defined above.

In some non-limiting embodiments, at least one of the HIL, HTL, and H-functional layer may include at least one of compounds represented by Formulae 301 to 320 below:

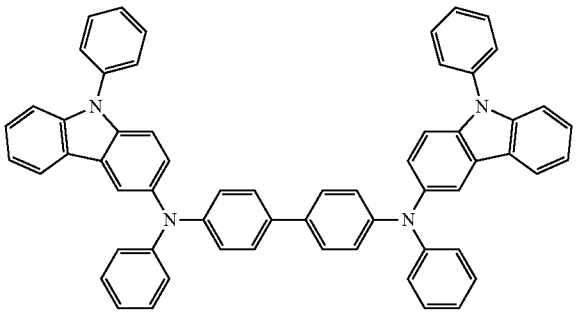

301

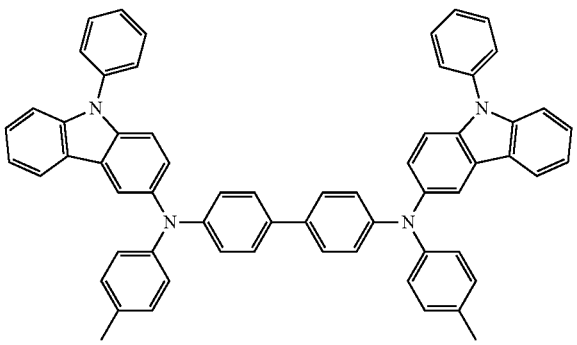

302

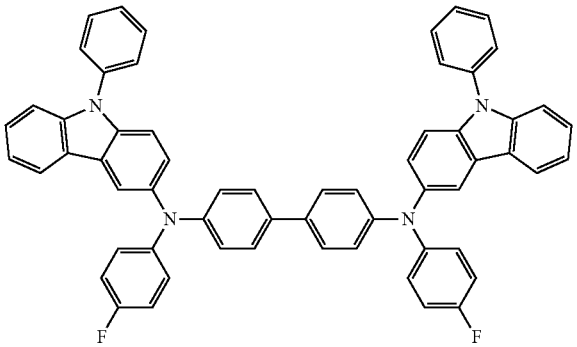

303

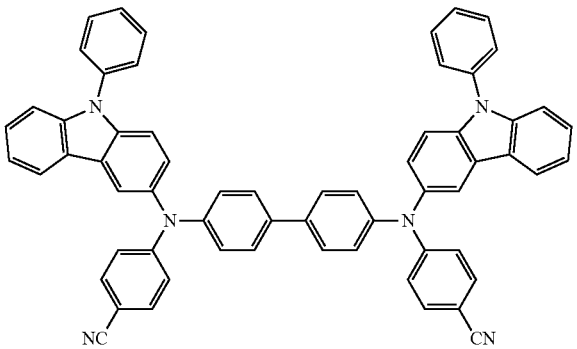

304

305
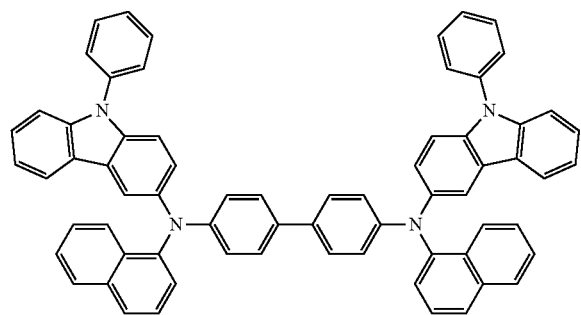
306
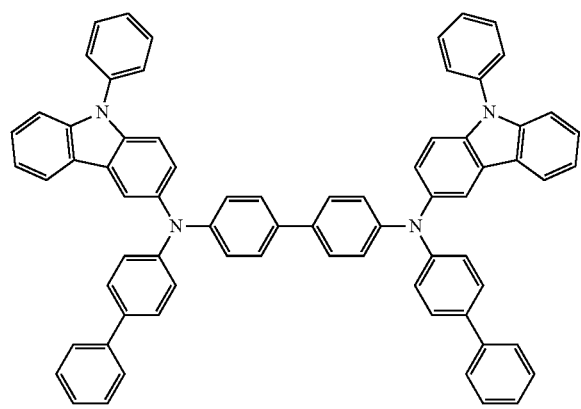
307
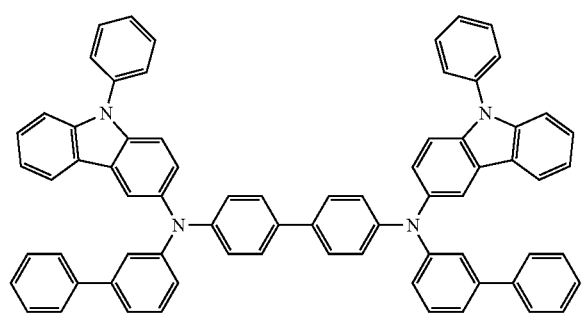
308
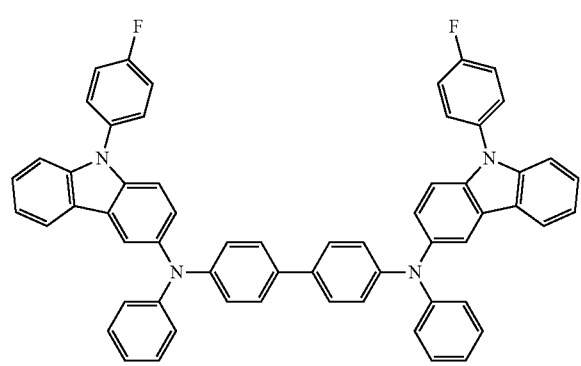
309
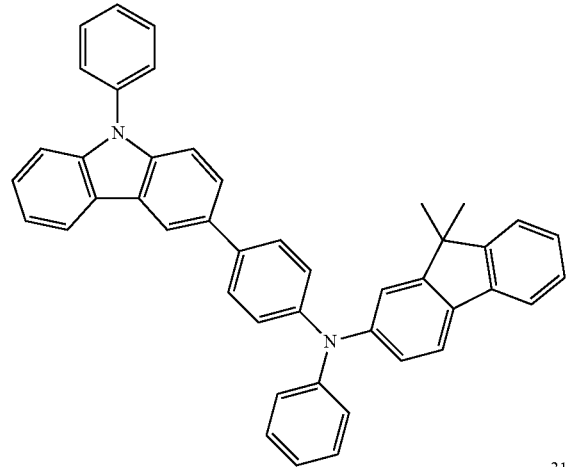
310
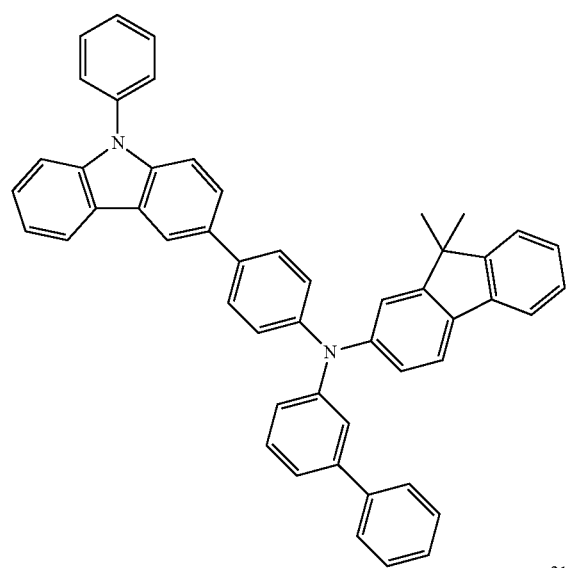
311
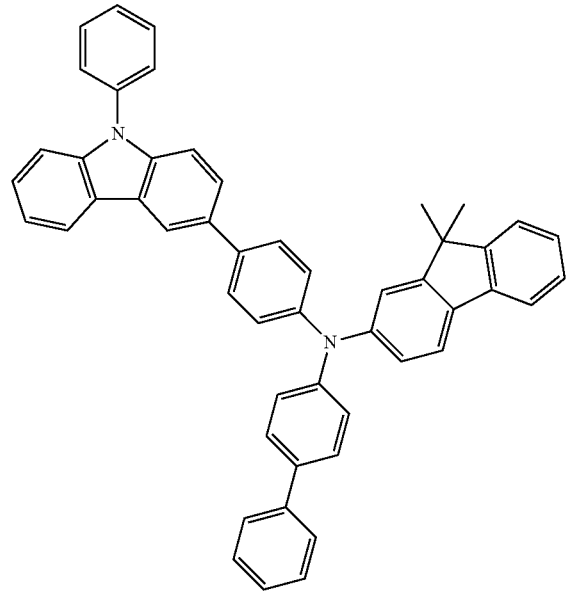

312
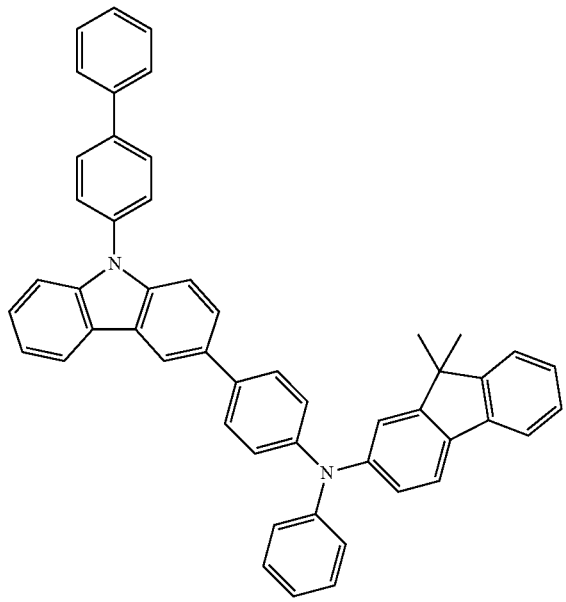
313
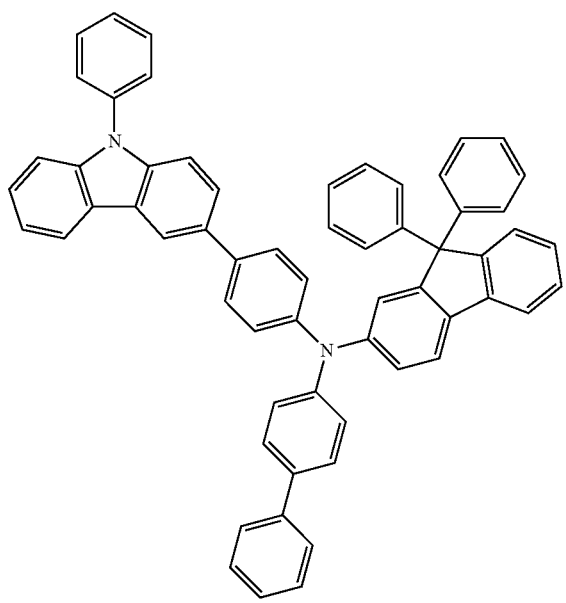
314
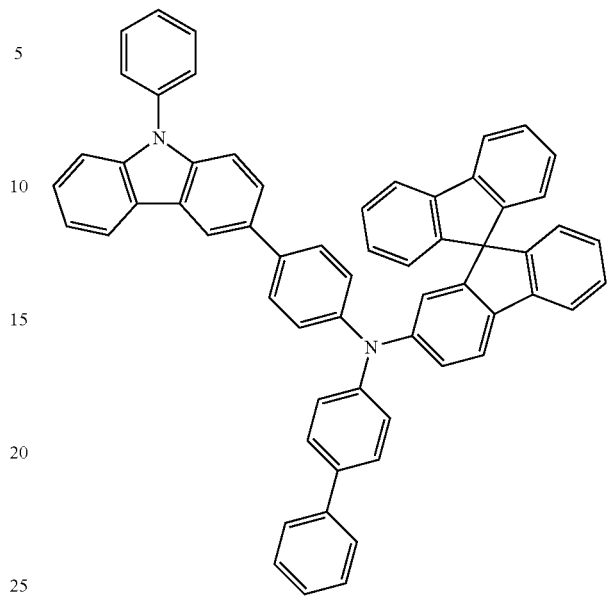
315
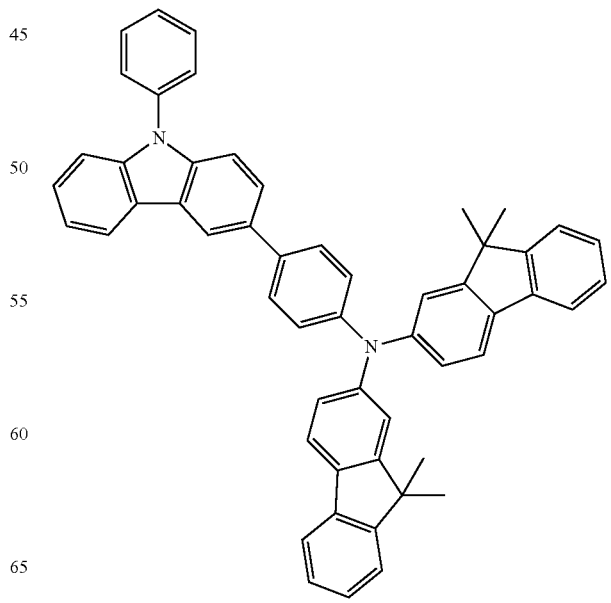

316

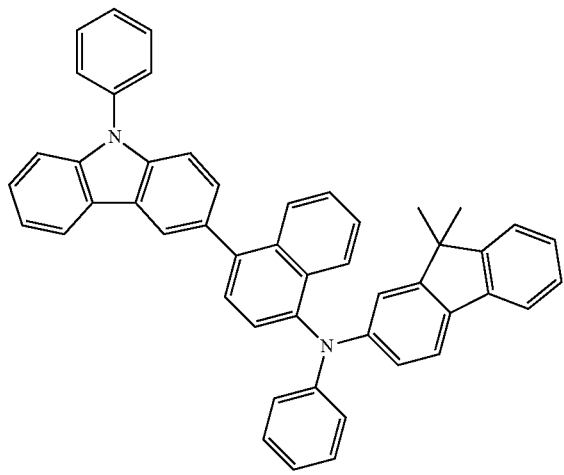

317

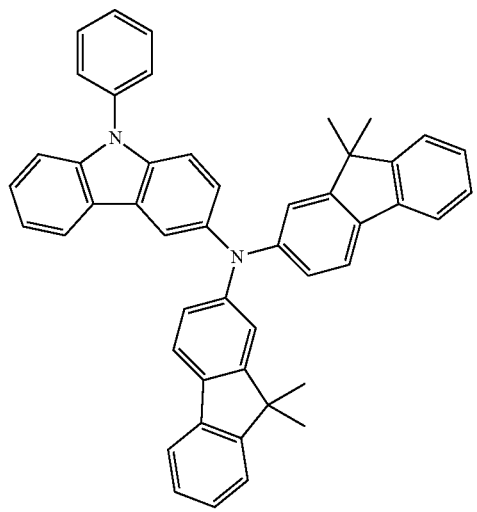

318

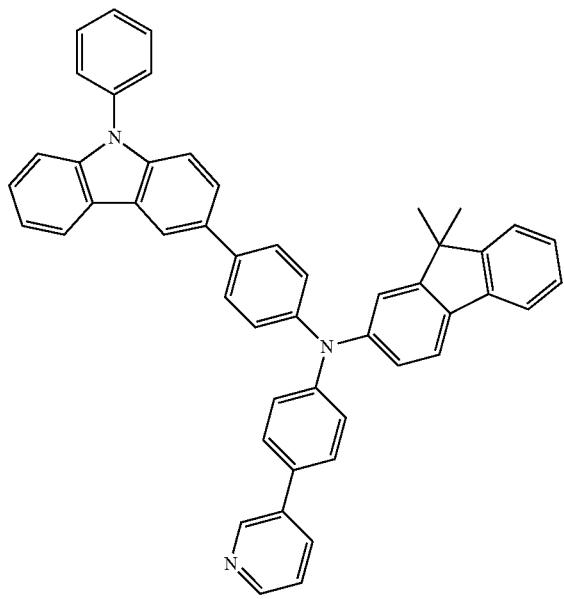

319

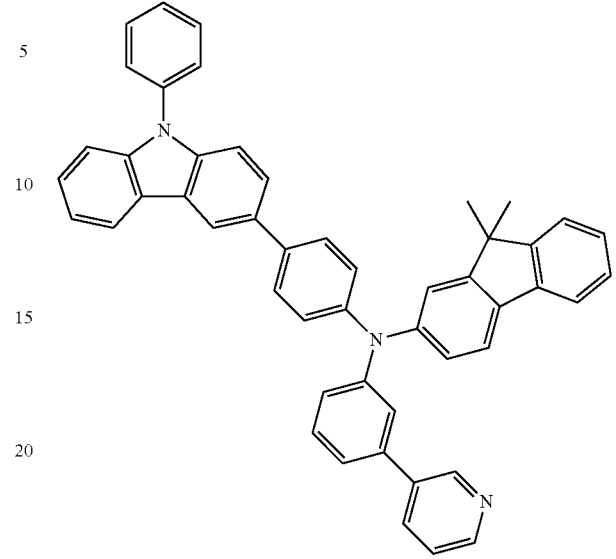

320

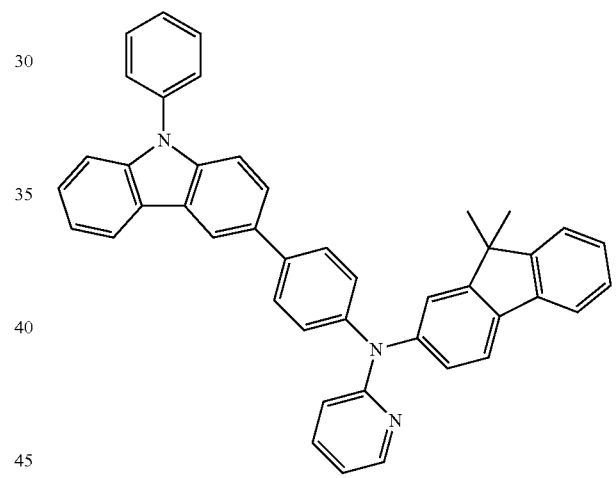

At least one of the HIL, HTL, and H-functional layer may further include a charge-generating material for improved layer conductivity, in addition to a hole injecting material, hole transport material, and/or material having both hole injection and hole transport capabilities as described above.

The charge-generating material may be, for example, a p-dopant. The p-dopant may be selected from quinine derivatives, metal oxides, and compounds with a cyano group, but it is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200 below.

<Compound 200>

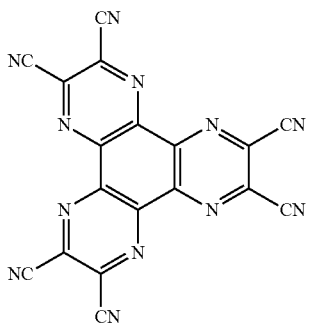

<F4-TCNQ>

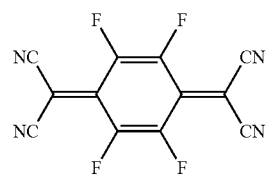

When one of the hole injection layer, the hole transport layer and the H-functional layer further includes a charge-generating material, the charge-generating material may be homogeneously dispersed or inhomogeneously distributed in the layer.

A buffer layer may be disposed between the EML and at least one of the HIL, the HTL and the H-functional layer. The buffer layer may compensate for an optical resonance distance of light according to a wavelength of the light emitted from the EML, and thus may increase efficiency. The butter layer may include one of a hole injecting material and a hole transporting material. In some other embodiments, the buffer layer may include the same material as one of the materials included in the HIL, HTL, and H-functional layer that underlie the buffer layer.

Then, an EML may be formed on the HTL, H-functional layer, or buffer layer by one of vacuum deposition, spin coating, casting, Langmuir-Blodget (LB) deposition and the like. When the EML is formed using vacuum deposition or spin coating, the deposition and coating conditions may be similar to those for the formation of the HIL, though the conditions for deposition and coating may vary according to the material that is used to form the EML.

The EML may include the organometallic compound (dopant) of Formula 1 described above and a host.

An amount of the dopant (i.e., the organometallic compound of Formula 1) in the EML may be from about 0.01 parts to about 15 parts by weight based on about 100 parts by weight of the host, but it is not limited thereto.

The thickness of the EML may be from about 100 Å to about 1000 Å, and, in some embodiments, may be from about 200 Å to about 600 Å. When the thickness of the EML is within these ranges, the EML may have good light emitting ability without imparting a substantial increase in driving voltage to an OLED including it.

In some embodiments, a hole blocking layer (HBL) may be formed on the EML to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. Any known hole-blocking material may be used. Non-limiting examples of hole-blocking materials are oxadiazole derivatives, triazole derivatives, and phenanthroline derivatives. For example, bathocuproine (BCP) represented by the following formula may be used as a material for forming the HBL.

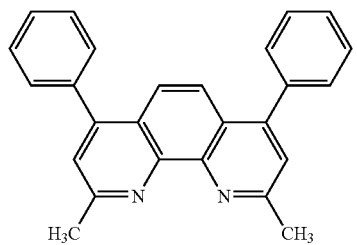

BCP

The thickness of the HBL may be from about 20 Å to about 1000 Å, and, in some embodiments, may be from about 30 Å to about 300 Å. When the thickness of the HBL is within these ranges, the HBL may have improved hole blocking ability without imparting a substantial increase in driving voltage to an OLED including it.

Then, an ETL may be formed on the HBL by any of a variety of methods, for example, one of vacuum deposition, spin coating and casting. When the ETL is formed using vacuum deposition or spin coating, the deposition and coating conditions may be similar to those for the formation of the HIL, though the deposition and coating conditions may vary according to a compound that is used to form the ETL. A material for forming the ETL may be any known material that can stably transport electrons injected from an electron injecting electrode (cathode). Non-limiting examples of materials for forming the ETL are a quinoline derivative, such as tris(8-quinolinorate)aluminum (Alq3), 3-(biphenyl-4-yl)-5-(4-tert-butylphenyl)-4-phenyl-4H-1,2,4-triazole (TAZ), bis(2-methyl-8-quinolinato)-4-phenylphenolate (BAlq), beryllium bis(benzoquinolin-10-olate (Bebq₂), 9,10-di(naphthalene-2-yl)anthracene (ADN), Compound 201, and Compound 202, but they are not limited thereto.

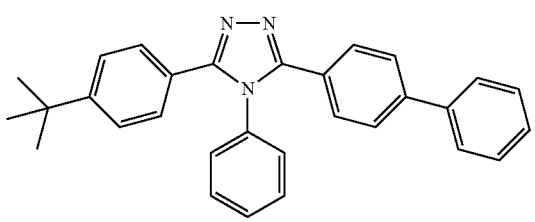

TAZ

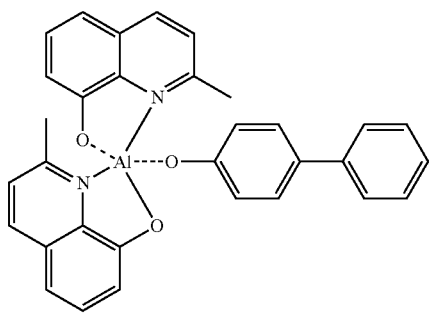

BAlq

<Compound 201>

<Compound 202>

BCP

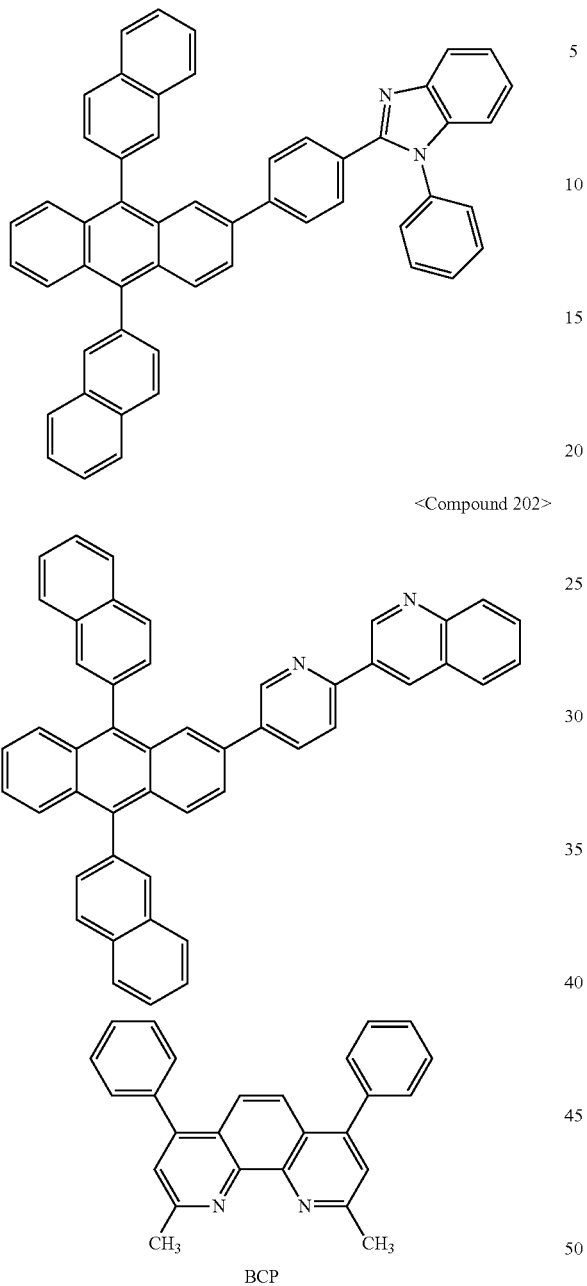

<Compound 203>

<LiQ>

The thickness of the ETL may be from about 100 Å to about 1,000 Å, and, in some embodiments, may be from about 150 Å to about 500 Å. When the thickness of the ETL is within these ranges, the ETL may have satisfactory electron transporting ability without imparting a substantial increase in driving voltage to an OLED including it.

In some embodiments, the ETL may further include a metal-containing material, in addition to an electron-transporting organic compound.

The metal-containing material may include a lithium (Li)-containing compound. Non-limiting examples of the Li-containing compound are lithium quinolate (LiQ) and Compound 203 below:

Then, an EIL, which facilitates injection of electrons from the cathode, may be formed on the ETL. Any suitable electron-injecting material may be used to form the EIL. Non-limiting examples of materials for forming the EIL are LiF, NaCl, CsF, $Li_2O$, and BaO. The deposition and coating conditions for forming the EIL 18 may be similar to those for the formation of the HIL, though the deposition and coating conditions may vary according to the material that is used to form the EIL 18.

The thickness of the EIL may be from about 1 Å to about 100 Å, and, in some embodiments, may be from about 3 Å to about 90 Å. When the thickness of the EIL is within these ranges, the EIL may have satisfactory electron injection ability without imparting a substantial increase in driving voltage to an OLED including it.

The second electrode 17 is disposed on the organic layer 15. The second electrode 17 may be a cathode that is an electron injection electrode. A metal material for forming the second electrode 17 may be one of a metal, an alloy, an electro-conductive compound that has a low work function and a mixture thereof. In this regard, the second electrode 17 may be formed of one of lithium (Li), magnesium (Mg), aluminum (Al), aluminum (Al)-lithium (Li), calcium (Ca), magnesium (Mg)-indium (In), magnesium (Mg)-silver (Ag) and the like, and the second electrode may be formed as a thin film type transmission electrode. In some embodiments, to manufacture a top-emission light-emitting diode, the transmission electrode may be formed of indium tin oxide (ITO) or indium zinc oxide (IZO).

Although the organic light-emitting diode of FIG. 1 is described above, the present invention is not limited thereto.

As used herein, the unsubstituted $C_1$-$C_{60}$ alkyl group (or a $C_1$-$C_{60}$ alkyl group) may be a linear or branched $C_1$-$C_{60}$ alkyl group, including a methyl group, an ethyl group, a propyl group, an isobutyl group, a sec-butyl group, a pentyl group, an iso-amyl group, and a hexyl group. The substituted $C_1$-$C_{60}$ alkyl group may be a $C_1$-$C_{60}$ alkyl group of which at least one hydrogen atom is substituted with at least one selected from among:

a deuterium atom, a halogen atom, a hydroxy group, a nitro group, a cyano group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_6$-$C_{60}$ aryl group, a $C_2$-$C_{60}$ heteroaryl group, —N($Q_{11}$)($Q_{12}$), and —Si($Q_{13}$)

($Q_{14}$)($Q_{15}$) (where $Q_{11}$ to $Q_{15}$ may be each independently one of a hydrogen atom, a $C_1$-$C_{60}$ alkyl group, a $C_2$-$C_{60}$ alkenyl group, a $C_2$-$C_{60}$ alkynyl group, a $C_5$-$C_{60}$ aryl group and a $C_2$-$C_{60}$ heteroaryl group).

The unsubstituted $C_1$-$C_{60}$ alkoxy group (or a $C_1$-$C_{60}$ alkoxy group) may be a group represented by —OA, A being an unsubstituted $C_1$-$C_{60}$ alkyl group as described above. Examples of the unsubstituted $C_1$-$C_{60}$ alkoxy group are a methoxy group, an ethoxy group, and an isopropyloxy group. At least one of the hydrogen atoms in the alkoxy group may be substituted with the substituents described above in conjunction with the substituted $C_1$-$C_{60}$ alkyl group.

The unsubstituted $C_2$-$C_{60}$ alkenyl group (a $C_2$-$C_{60}$ alkenyl group) is a $C_2$-$C_{60}$ alkyl group having at least one carbon-carbon triple bond in the center or at a terminal thereof. Examples of the alkenyl group are an ethenyl group, a propenyl group, a butenyl group, and the like. At least one hydrogen atom in the unsubstituted $C_2$-$C_{60}$ alkenyl group may be substituted with those substituents described above in conjunction with the substituted $C_1$-$C_{60}$ alkyl group.

The unsubstituted $C_2$-$C_{60}$ alkynyl group (a $C_2$-$C_{60}$ alkynyl group) is a $C_2$-$C_{60}$ alkyl group having at least one carbon-carbon triple bond in the center or at a terminal thereof. Examples of the unsubstituted $C_2$-$C_{60}$ alkynyl group (a $C_2$-$C_{60}$ alkynyl group) are an ethenyl group, a propynyl group, and the like. At least one hydrogen atom in the alkynyl group may be substituted with those substituents described above in conjunction with the substituted $C_1$-$C_{60}$ alkyl group.

The unsubstituted $C_6$-$C_{60}$ aryl group is a monovalent carbocyclic aromatic system having 6 to 60 carbon atoms including at least one aromatic ring. The unsubstituted $C_5$-$C_{60}$ arylene group is a divalent carbocyclic aromatic system having 6 to 60 carbon atoms including at least one aromatic ring. When the aryl group and the arylene group have at least two rings, they may be fused to each other via a single bond. At least one hydrogen atom in the aryl group and the arylene group may be substituted with those substituents described above in conjunction with the $C_1$-$C_{60}$ alkyl group.

Examples of the substituted or unsubstituted $C_6$-$C_{60}$ aryl group are a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m- or p-fluorophenyl group and a dichlorophenyl group), a dicyanophenyl group, a trifluoromethoxyphenyl group, an o-, m- or p-tolyl group, an o-, m- or p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, and an ovalenyl group. Examples of the substituted $C_5$-$C_{60}$ aryl group may be inferred based on those of the unsubstituted $C_5$-$C_{60}$ aryl group and the substituted $C_1$-$C_{30}$ alkyl group described above. Examples of the substituted or unsubstituted $C_5$-$C_{60}$ arylene group may be inferred based on those examples of the substituted or unsubstituted $C_5$-$C_{60}$ aryl group described above.

The unsubstituted $C_2$-$C_{60}$ heteroaryl group is a monovalent carbocyclic aromatic system having at least one aromatic ring and at least one of the heteroatoms selected from the group consisting of N, O, P, and S. The unsubstituted $C_2$-$C_{60}$ heteroarylene group is a divalent carbocyclic aromatic system having at least one aromatic ring and at least one of the heteroatoms selected from the group consisting of N, O, P, and S. In this regard, when the heteroaryl group and the heteroarylene group have at least two rings, they may be fused to each other via a single bond. At least one hydrogen atom in the heteroaryl group and the heteroarylene group may be substituted with those substituents described with reference to the $C_1$-$C_{60}$ alkyl group.

Examples of the unsubstituted $C_2$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group and an imidazopyrimidinyl group. Examples of the substituted or unsubstituted $C_2$-$C_{60}$ heteroarylene group may be inferred based on those examples of the substituted or unsubstituted $C_2$-$C_{60}$ arylene group described above.

The substituted or unsubstituted $C_6$-$C_{60}$ aryloxy group indicates —$OA_2$ (where $A_2$ is a substituted or unsubstituted $C_6$-$C_{60}$ aryl group described above). The substituted or unsubstituted $C_5$-$C_{60}$ arylthiol group indicates —$SA_3$ (where $A_3$ is a substituted or unsubstituted $C_6$-$C_{60}$ aryl group described above).

Hereinafter, the present invention will be described in detail with reference to the following synthesis examples and other examples. However, these examples are for illustrative purposes only and are not intended to limit the scope of the present invention.

SYNTHESIS EXAMPLES

Synthesis Example 1: Synthesis of Compound 5

Compound 5 was synthesized according to Reaction Scheme 1 below:

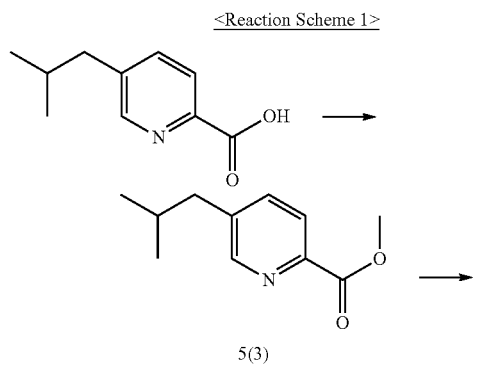

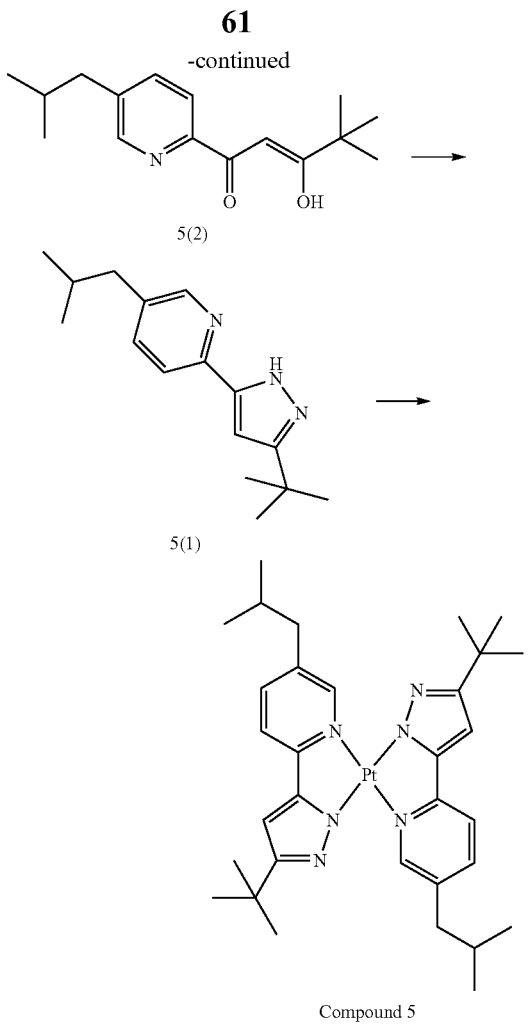

Compound 5

Synthesis of Intermediate 5(3)

After 25.7 g (143.6 mmol) of 5-isobutyl-pyridine-2-carboxylic acid was dissolved in 100 mL of methanol, 5 mL of concentrated sulfuric acid was added to the solution and heated under reflux at about 80° C. for about 18 hours. After completion of the reaction, the reaction mixture was concentrated under reduced pressure and mixed with 100 mL of dichloromethane. A saturated sodium hydrogen carbonate aqueous solution was slowly added into the resulting mixture at 0° C. for alkalification and then extracted to collect an organic layer, which was then dried using magnesium sulfate, and this was followed by distillation under reduced pressure to obtain 26.0 g (137.8 mmol) of Intermediate 5(3) (Yield: 96%).

LC-MS m/z=194 (M+H)$^+$ $^1$H NMR (500 MHz, CDCl$_3$) δ=8.87 (s, 1H), 8.31 (d, 1H), 8.19 (d, 1H), 3.92 (s, 3H), 2.55 (d, 2H), 2.01-1.99 (m, 1H), 1.01 (d, 6H).

Synthesis of Intermediate 5(2)

After 1.0 g (43.4 mmol) of NaH was added to 80 mL of anhydrous tetrahydrofuran, 4.5 mL (34.8 mmol) of 3,3-dimethyl-2-butanone was slowly added to the mixture. After 1 hour, 5.6 g (29.0 mmol) of Intermediate 5(3) was added to the mixture and heated under reflux at about 80° C. for about 16 hours. After completion of the reaction, 30 mL of distilled water, and then a 4N HCl solution were slowly added for neutralization, and this was followed by extraction five times with 100 mL portions of dichloromethane to collect an organic layer, which was then dried using magnesium sulfate. The solvents were then removed by distillation under reduced pressure, and the residue was purified by column chromatography to obtain 3.9 g (15.1 mmol) of Intermediate 5(2) (Yield: 52%).

LC-MS m/z=262 (M+H)$^+$

Synthesis of Intermediate 5(1)

After 3.6 g (13.9 mmol) of Intermediate 5(2) was dissolved in 50 mL of ethanol at room temperature, 4.0 mL (140.0 mmol) of hydrazine hydrate was added to the mixture and heated under reflex at about 80° C. for about 18 hours. The reaction product was concentrated under reduced pressure, and extracted with 80 mL of distilled water and 100 ml of dichloromethane to collect an organic layer, which was then dried using magnesium sulfate. The solvents were then removed by distillation under reduced pressure, and the product was purified by column chromatography to obtain 2.7 g (10.4 mmol) of Intermediate 5(1) (Yield: 75%).

LC-MS m/z=258 (M+H)$^+$ $^1$H NMR (500 MHz, CDCl$_3$) δ=8.67 (s, 1H), 7.81 (d, 1H), 7.36 (d, 1H), 6.75 (s, 1H), 2.52 (d, 2H), 1.98-1.96 (m, 1H), 1.31 (s, 9H), 0.98 (d, 6H).

Synthesis of Compound 5

After 0.6 g (2.5 mmol) of Intermediate 5(1) was dissolved in a mixed solvent of 30 mL of ethanol and 10 mL of distilled water at room temperature, 0.5 g (1.2 mmol) of K$_2$PtCl$_4$ was added to the mixture and heated under reflux for about 18 hours. After completion of the reaction was determined by liquid chromatography-mass spectrometry (LC-MS), the reaction product was filtered to obtain 0.7 g (1.0 mmol) of Compound 5 (Yield: 40%). This compound was identified using LC-MS and $^1$H nuclear magnetic resonance (NMR).

LC-MS m/z=708 (M+H)$^+$ $^1$H NMR (500 MHz, CDCl$_3$) δ=10.32 (s, 1H), 8.31 (d, 1H), 8.17 (d, 1H), 6.73 (s, 1H), 2.58 (d, 2H), 1.97-1.95 (m, 1H), 1.32 (s, 9H), 1.00 (d, 6H).

Synthesis Example 2: Synthesis of Compound 1

Compound 1 was synthesized according to Reaction Scheme 2 below:

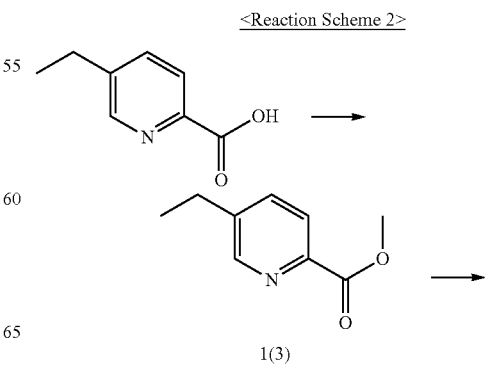

<Reaction Scheme 2>

-continued

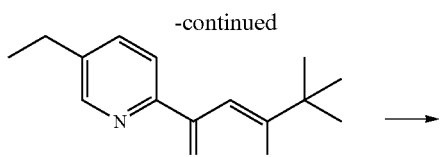

1(2)

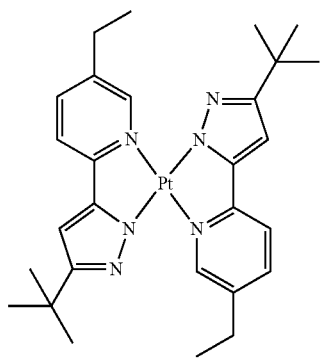

1(1)

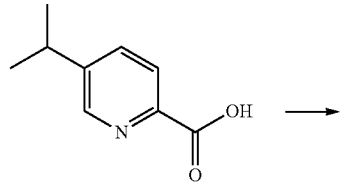

Compound 1

Synthesis of Intermediate 1(3)

Intermediate 1(3) was synthesized in the same manner as in the synthesis of Intermediate 5(3) of Synthesis Example 1, except that 5-ethyl-pyridine-2-carboxylic acid, instead of 5-isobutyl-pyridine-2-carboxylic acid, was used (Yield: 92%). This compound was identified using LC-MS.

LC-MS m/z=166 (M+H)$^+$

Synthesis of Intermediate 1(2)

Intermediate 1(2) was synthesized in the same manner as in the synthesis of Intermediate 5(2) of Synthesis Example 1, except that Intermediate 1(3), instead of Intermediate 5(3), was used (Yield: 52%). This compound was identified using LC-MS.

LC-MS m/z=234 (M+H)$^+$

Synthesis of Intermediate 1(1)

Intermediate 1(1) was synthesized in the same manner as in the synthesis of Intermediate 5(1) of Synthesis Example 1, except that Intermediate 1(2), instead of Intermediate 5(2), was used (Yield: 75%). This compound was identified using LC-MS.

LC-MS m/z=230 (M+H)$^+$ $^1$H NMR (500 MHz, CDCl$_3$) δ=8.62 (s, 1H), 7.82 (d, 1H), 7.34 (d, 1H), 6.78 (s, 1H), 2.58 (q, 2H), 1.33 (s, 9H), 1.22 (t, 3H)

Synthesis of Compound 1

Compound 1 was synthesized in the same manner as in the synthesis of Compound 5 of Synthesis Example 1, except that Intermediate 1(1), instead of Intermediate 5(1), was used (Yield: 51%). This compound was identified using LC-MS and $^1$H NMR.

LC-MS m/z=652 (M+H)$^+$ $^1$H NMR (500 MHz, CDCl$_3$) δ=10.28 (s, 1H), 8.27 (d, 1H), 8.19 (d, 1H), 6.71 (s, 1H), 2.43 (q, 2H), 1.35 (s, 9H), 1.26 (t, 3H).

Synthesis Example 3: Synthesis of Compound 2

Compound 2 was synthesized according to Reaction Scheme 3 below:

<Reaction Scheme 3>

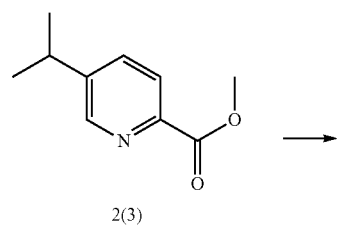

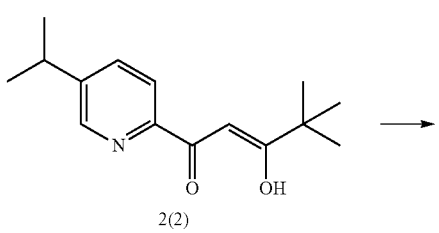

2(3)

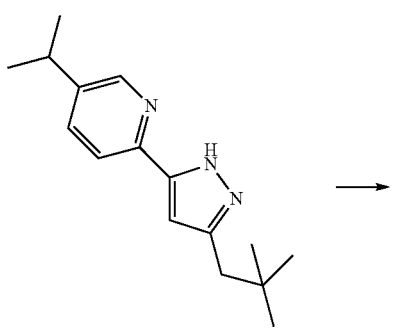

2(2)

2(1)

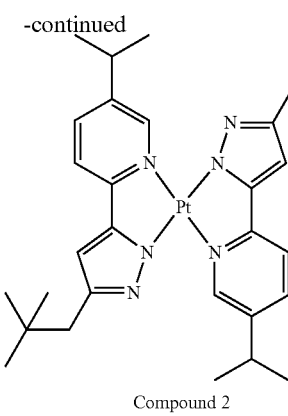

Compound 2

Synthesis of Intermediate 2(3)

Intermediate 2(3) was synthesized in the same manner as in the synthesis of Intermediate 5(3) of Synthesis Example 1, except that 5-isopropyl-pyridine-2-carboxylic acid, instead of 5-isobutyl-pyridine-2-carboxylic acid, was used (Yield: 96%). This compound was identified using LC-MS.

LC-MS m/z=180 (M+H)$^+$

Synthesis of Intermediate 2(2)

Intermediate 2(2) was synthesized in the same manner as in the synthesis of Intermediate 5(2) of Synthesis Example 1, except that 4,4-dimethyl-pentan-2-one, instead of 3,3-dimethyl-2-butanone, was used (Yield: 12%). This compound was identified using LC-MS.

LC-MS m/z=262 (M+H)$^+$

Synthesis of Intermediate 2(1)

Intermediate 2(1) was synthesized in the same manner as in the synthesis of Intermediate 5(1) of Synthesis Example 1, except that Intermediate 2(2), instead of Intermediate 5(2), was used (Yield: 70%). This compound was identified using LC-MS.

LC-MS m/z=258 (M+H)$^+$ $^1$H NMR (500 MHz, CDCl$_3$) δ=8.58 (s, 1H), 7.76 (d, 1H), 7.23 (d, 1H), 6.69 (s, 1H), 3.24-3.22 (m, 1H), 2.48 (s, 2H), 1.28 (d, 6H), 1.09 (t, 9H).

Synthesis of Compound 2

Compound 2 was synthesized in the same manner as in the synthesis of Compound 5 of Synthesis Example 1, except that Intermediate 2(1), instead of Intermediate 5(1), was used (Yield: 45%). This compound was identified using LC-MS and $^1$H NMR.

LC-MS m/z=708 (M+H)$^+$ $^1$H NMR (500 MHz, CDCl$_3$) δ=10.18 (s, 1H), 8.21 (d, 1H), 8.15 (d, 1H), 6.76 (s, 1H), 3.23-3.21 (m, 1H), 2.45 (s, 2H), 1.25 (d, 6H), 1.08 (t, 9H).

Synthesis Example 4: Synthesis of Compound 3

Compound 3 was synthesized according to Reaction Scheme 4 below:

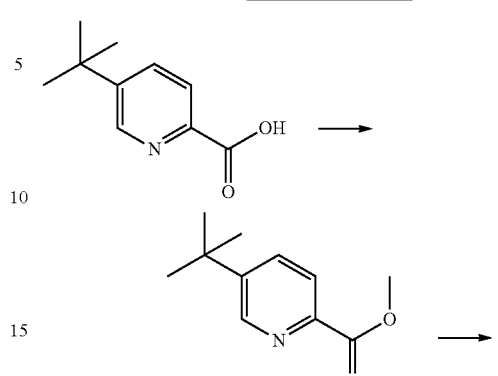

<Reaction Scheme 4>

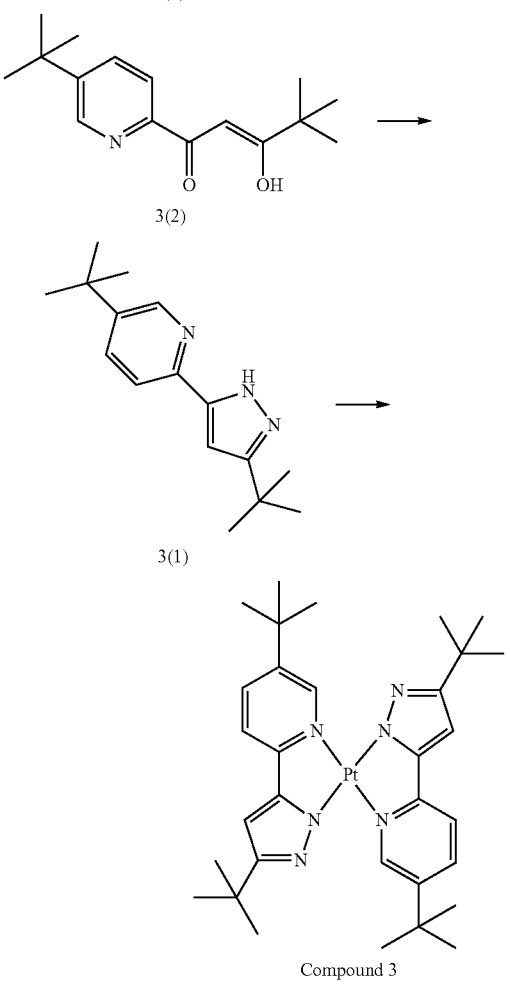

Compound 3

Synthesis of Intermediate 3(3)

Intermediate 3(3) was synthesized in the same manner as in the synthesis of Intermediate 5(3) of Synthesis Example 1, except that 5-tert-butyl-pyridine-2-carboxylic acid, instead of 5-isobutyl-pyridine-2-carboxylic acid, was used (Yield: 95%). This compound was identified using LC-MS.

LC-MS m/z=194 (M+H)$^+$

Synthesis of Intermediate 3(2)

Intermediate 3(2) was synthesized in the same manner as in the synthesis of Intermediate 5(2) of Synthesis Example 1, except that Intermediate 3(3), instead of Intermediate 5(3), was used (Yield: 50%). This compound was identified using LC-MS.

LC-MS m/z=262 (M+H)$^+$

Synthesis of Intermediate 3(1)

Intermediate 3(1) was synthesized in the same manner as in the synthesis of Intermediate 5(1) of Synthesis Example 1, except that Intermediate 3(2), instead of Intermediate 5(2), was used (Yield: 72%). This compound was identified using LC-MS.

LC-MS m/z=258 (M+H)$^+$ $^1$H NMR (500 MHz, CDCl$_3$) δ=8.66 (s, 1H), 7.54 (d, 1H), 7.31 (d, 1H), 6.84 (s, 1H), 1.35-1.31 (m, 18H).

Synthesis of Compound 3

Compound 3 was synthesized in the same manner as in the synthesis of Compound 5 of Synthesis Example 1, except that Intermediate 3(1), instead of Intermediate 5(1), was used (Yield: 71%). This compound was identified using LC-MS and $^1$H NMR.

LC-MS m/z=708 (M+H)$^+$ $^1$H NMR (500 MHz, CDCl$_3$) δ=10.26 (s, 1H), 8.25 (d, 1H), 8.11 (d, 1H), 6.81 (s, 1H), 1.36-1.33 (m, 18H).

Synthesis Example 5: Synthesis of Compound 4

Compound 4 was synthesized according to Reaction Scheme 5 below:

<Reaction Scheme 5>

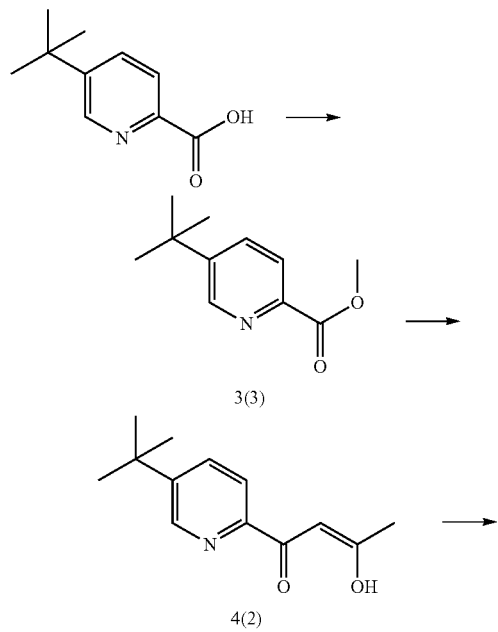

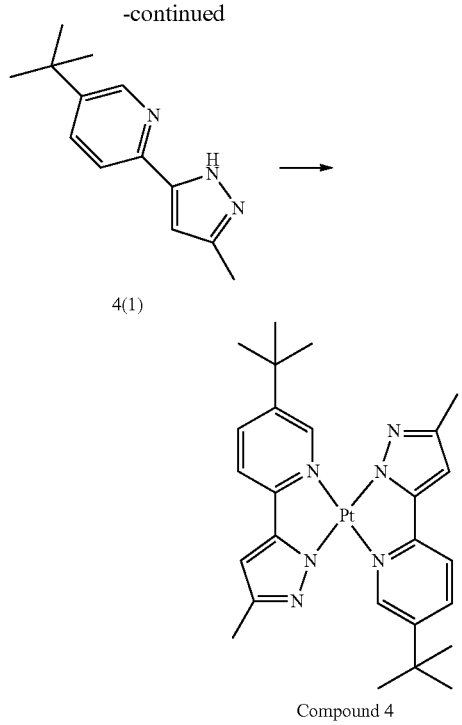

Compound 4

Synthesis of Intermediate 4(2)

Intermediate 4(2) was synthesized in the same manner as in the synthesis of Intermediate 5(2) of Synthesis Example 1, except that Intermediate 3(3) and acetone, respectively, instead of Intermediate 5(3) and 3,3-dimethyl-2-butanone, were used (Yield: 32%). This compound was identified using LC-MS.

LC-MS m/z=220 (M+H)$^+$

Synthesis of Intermediate 4(1)

Intermediate 4(1) was synthesized in the same manner as in the synthesis of Intermediate 5(1) of Synthesis Example 1, except that Intermediate 4(2), instead of Intermediate 5(2), was used (Yield: 75%). This compound was identified using LC-MS.

LC-MS m/z=216 (M+H)$^+$ $^1$H NMR (500 MHz, CDCl$_3$) δ=8.64 (s, 1H), 7.56 (d, 1H), 7.28 (d, 1H), 6.81 (s, 1H), 2.26 (s, 3H), 1.36 (s, 9H).

Synthesis of Compound 4

Compound 4 was synthesized in the same manner as in the synthesis of Compound 5 of Synthesis Example 1, except that Intermediate 4(1), instead of Intermediate 5(1), was used (Yield: 62%). This compound was identified using LC-MS and $^1$H NMR.

LC-MS m/z=624 (M+H)$^+$ $^1$H NMR (500 MHz, CDCl$_3$) δ=10.24 (s, 1H), 8.22 (d, 1H), 8.06 (d, 1H), 6.82 (s, 1H), 2.18 (s, 3H), 1.33 (s, 9H).

Synthesis Example 6: Synthesis of Compound 6

Compound 6 was synthesized according to Reaction Scheme 6 below:

Reaction Scheme 6

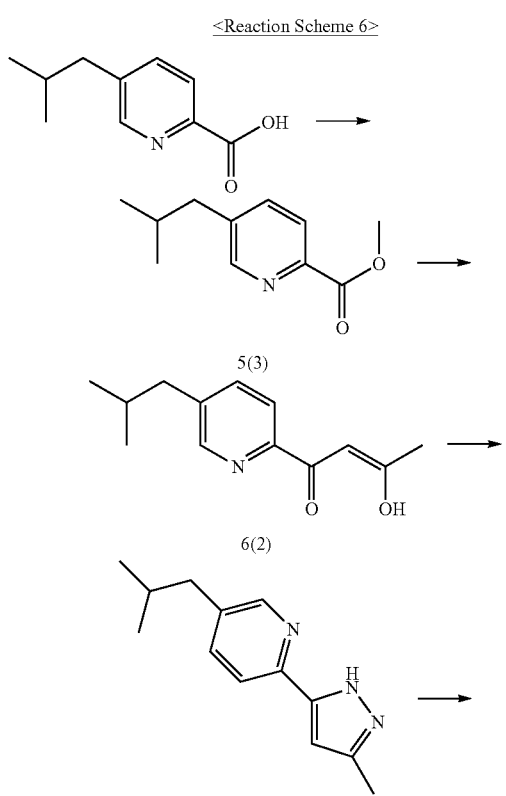

Synthesis of Intermediate 6(2)

Intermediate 6(2) was synthesized in the same manner as in the synthesis of Intermediate 5(2) of Synthesis Example 1, except that acetone, instead of 3,3-dimethyl-2-butanone, was used (Yield: 30%). This compound was identified using LC-MS.

LC-MS m/z=220 (M+H)⁺

Synthesis of Intermediate 6(1)

Intermediate 6(1) was synthesized in the same manner as in the synthesis of Intermediate 5(1) of Synthesis Example 1, except that Intermediate 6(2), instead of Intermediate 5(2), was used (Yield: 70%). This compound was identified using LC-MS.

LC-MS m/z=216 (M+H)⁺

$^1$H NMR (500 MHz, CDCl$_3$) δ=8.63 (s, 1H), 7.76 (d, 1H), 7.32 (d, 1H), 6.77 (s, 1H), 2.56 (d, 2H), 2.23 (s, 3H), 1.98-1.96 (m, 1H), 0.98 (d, 6H).

Synthesis of Compound 6

Compound 6 was synthesized in the same manner as in the synthesis of Compound 5 of Synthesis Example 1, except that Intermediate 6(1), instead of Intermediate 5(1), was used (Yield: 70%). This compound was identified using LC-MS and $^1$H NMR.

LC-MS m/z=624 (M+H)⁺

$^1$H NMR (500 MHz, CDCl$_3$) δ=10.22 (s, 1H), 8.25 (d, 1H), 8.10 (d, 1H), 6.81 (s, 1H), 2.52 (d, 2H), 2.21 (s, 3H), 1.97-1.95 (m, 1H), 1.00 (d, 6H).

Synthesis Example 7: Synthesis of Compound 7

Compound 7 was synthesized according to Reaction Scheme 7 below:

Reaction Scheme 7

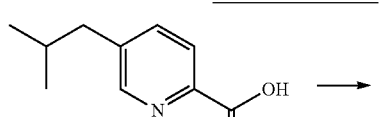

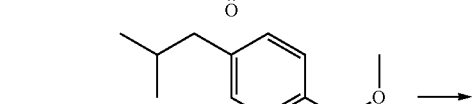

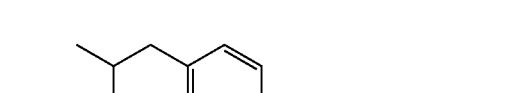

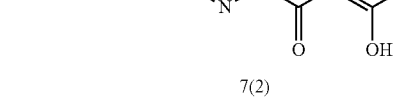

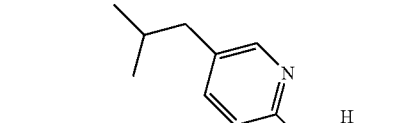

-continued

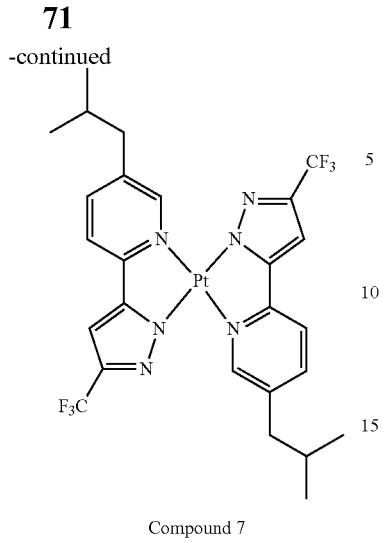

Compound 7

Synthesis of Intermediate 7(2)

Intermediate 7(2) was synthesized in the same manner as in the synthesis of Intermediate 5(2) of Synthesis Example 1, except that 1,1,1-trifluoro-propan-2-one, instead of 3,3-dimethyl-2-butanone, was used (Yield: 56%). This compound was identified using LC-MS.

LC-MS m/z=274 (M+H)$^+$

Synthesis of Intermediate 7(1)

Intermediate 7(1) was synthesized in the same manner as in the synthesis of Intermediate 5(1) of Synthesis Example 1, except that Intermediate 7(2), instead of Intermediate 5(2), was used (Yield: 75%). This compound was identified using LC-MS.

LC-MS m/z=270 (M+H)$^+$
$^1$H NMR (500 MHz, CDCl$_3$) δ=8.58 (s, 1H), 7.51 (d, 1H), 7.20 (br s, 1H), 6.56 (s, 1H), 2.51 (d, 2H), 1.99-1.96 (m, 1H), 0.96 (d, 6H).

Synthesis of Compound 7

Compound 7 was synthesized in the same manner as in the synthesis of Compound 5 of Synthesis Example 1, except that Intermediate 7(1), instead of Intermediate 5(1), was used (Yield: 65%). This compound was identified using LC-MS and $^1$H NMR.

LC-MS m/z=732 (M+H)$^+$
$^1$H NMR (500 MHz, CDCl$_3$) δ=10.42 (s, 1H), 8.31 (d, 1H), 8.05 (d, 1H), 6.85 (s, 1H), 2.55 (d, 2H), 1.95-1.93 (m, 1H), 1.02 (d, 6H).

Synthesis Example 8: Synthesis of Compound 8

Compound 8 was synthesized according to Reaction Scheme 8 below:

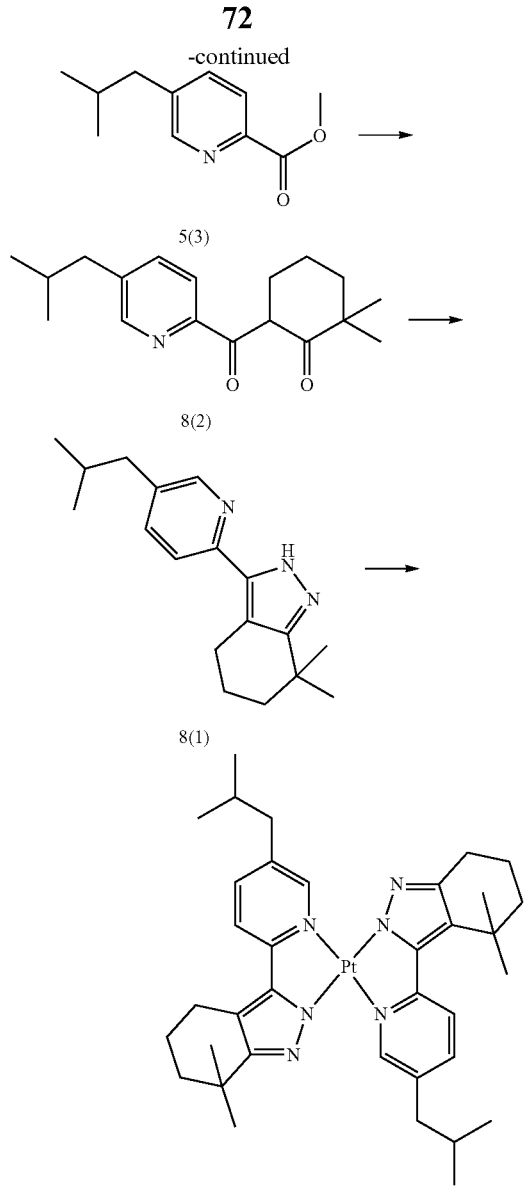

Compound 8

Synthesis of Intermediate 8(2)

Intermediate 8(2) was synthesized in the same manner as in the synthesis of Intermediate 5(2) of Synthesis Example 1, except that 2,2-dimethyl-cyclohexanone, instead of 3,3-dimethyl-2-butanone, was used (Yield: 45%). This compound was identified using LC-MS.

LC-MS m/z=288 (M+H)$^+$

Synthesis of Intermediate 8(1)

Intermediate 8(1) was synthesized in the same manner as in the synthesis of Intermediate 5(1) of Synthesis Example 1, except that Intermediate 8(2), instead of Intermediate 5(2), was used (Yield: 55%). This compound was identified using LC-MS.

LC-MS m/z=284 (M+H)$^+$
$^1$H NMR (500 MHz, CDCl$_3$) δ=8.50 (s, 1H), 7.41 (d, 1H), 7.22 (d, 1H), 2.51-2.49 (m, 4H), 1.99-1.96 (m, 1H), 1.62-1.53 (m, 4H), 1.29 (s, 6H), 0.96 (d, 6H).

Synthesis of Compound 8

Compound 8 was synthesized in the same manner as in the synthesis of Compound 5 of Synthesis Example 1, except that Intermediate 8(1), instead of Intermediate 5(1), was used (Yield: 60%). This compound was identified using LC-MS and $^1$H NMR.

LC-MS m/z=760 (M+H)$^+$ $^1$H NMR (500 MHz, CDCl$_3$) δ=10.52 (s, 1H), 8.36 (d, 1H), 8.09 (d, 1H), 2.55-2.46 (m, 4H), 1.97-1.94 (m, 1H), 1.61-1.54 (m, 4H), 1.26 (s, 6H), 1.00 (d, 6H).

Synthesis Example 9: Synthesis of Compound 9

Compound 9 was synthesized according to Reaction Scheme 9 below:

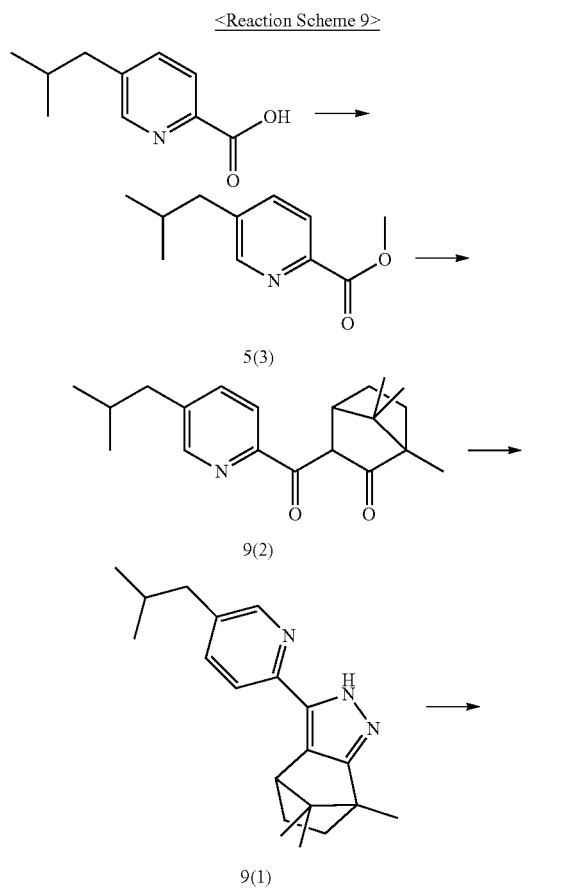

Synthesis of Intermediate 9(2)

Intermediate 9(2) was synthesized in the same manner as in the synthesis of Intermediate 5(2) of Synthesis Example 1, except that camphor, instead of 3,3-dimethyl-2-butanone, was used (Yield: 72%). This compound was identified using LC-MS.

LC-MS m/z=314 (M+H)$^+$

Synthesis of Intermediate 9(1)

Intermediate 9(1) was synthesized in the same manner as in the synthesis of Intermediate 5(1) of Synthesis Example 1, except that Intermediate 9(2), instead of Intermediate 5(2), was used (Yield: 70%). This compound was identified using LC-MS.

LC-MS m/z=310 (M+H)$^+$ $^1$H NMR (500 MHz, CDCl$_3$) δ=8.47 (s, 1H), 7.38 (d, 1H), 7.12 (d, 1H), 2.82 (br s, 1H), 2.73 (d, 2H), 2.26-2.24 (m, 1H). 1.71~1.66 (m, 4H), 1.51 (s, 3H), 1.12 (s, 6H), 0.97 (s, 6H)

Synthesis of Compound 9

Compound 9 was synthesized in the same manner as in the synthesis of Compound 5 of Synthesis Example 1, except that Intermediate 9(1), instead of Intermediate 5(1), was used (Yield: 55%). This compound was identified using LC-MS and $^1$H NMR.

LC-MS m/z=812 (M+H)$^+$ $^1$H NMR (500 MHz, CDCl$_3$) δ=10.36 (s, 1H), 8.22 (d, 1H), 8.14 (d, 1H), 2.86 (br s, 1H), 2.79 (d, 2H), 2.24-2.21 (m, 1H). 1.68~1.64 (m, 4H), 1.62 (s, 3H), 1.21 (s, 6H), 1.04 (s, 6H)

Synthesis Example 10: Synthesis of Compound 10

Compound 10 was synthesized according to Reaction Scheme 1 below:

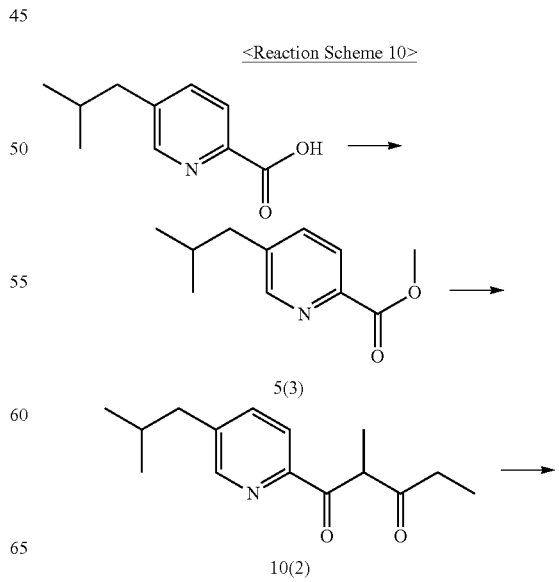

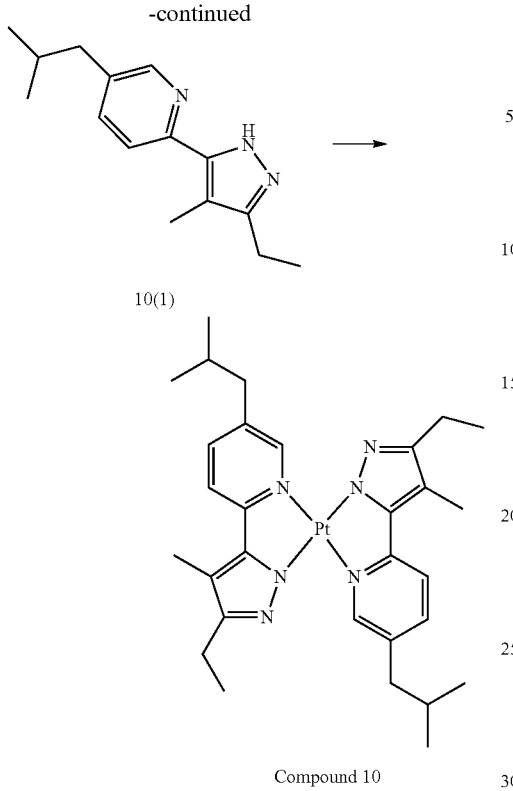

10(1)

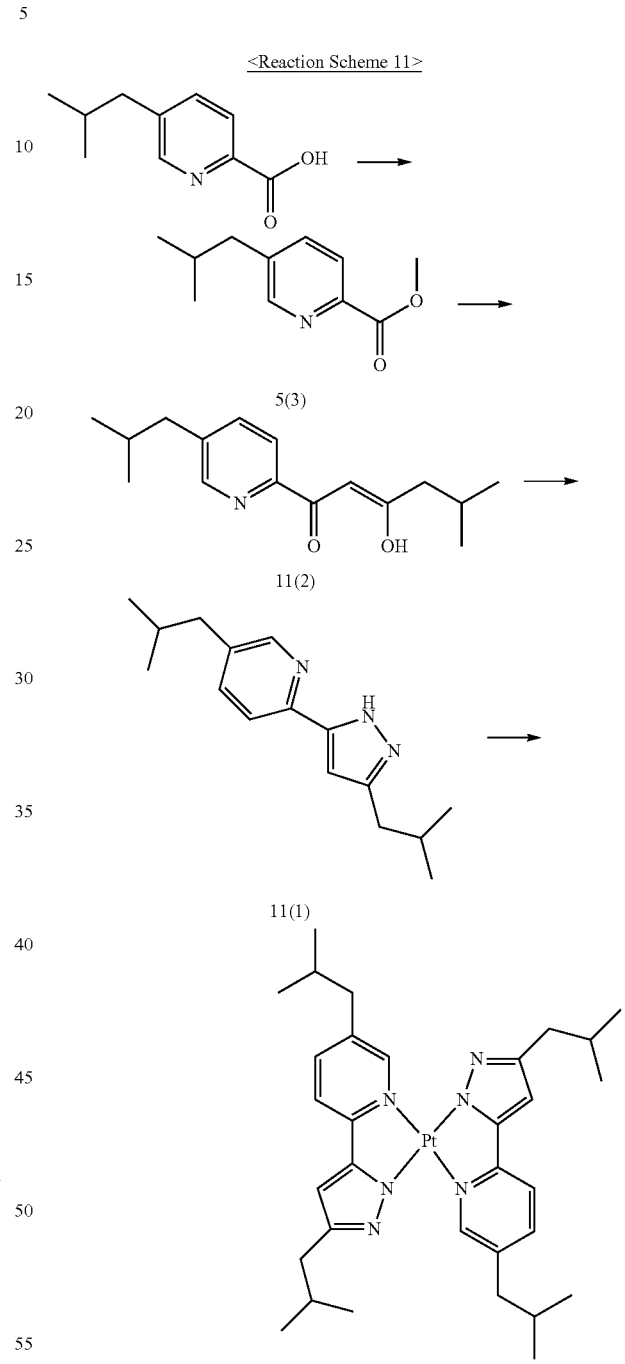

Compound 10

Synthesis of Intermediate 10(2)

Intermediate 10(2) was synthesized in the same manner as in the synthesis of Intermediate 5(2) of Synthesis Example 1, except that 3-pentanone, instead of 3,3-dimethyl-2-butanone, was used (Yield: 51%). This compound was identified using LC-MS.

LC-MS m/z=248 (M+H)$^+$

Synthesis of Intermediate 10(1)

Intermediate 10(1) was synthesized in the same manner as in the synthesis of Intermediate 5(1) of Synthesis Example 1, except that Intermediate 10(2), instead of Intermediate 5(2), was used (Yield: 65%). This compound was identified using LC-MS.

LC-MS m/z=244 (M+H)$^+$ $^1$H NMR (500 MHz, CDCl$_3$) δ=8.41 (s, 1H), 7.35 (d, 1H), 7.11 (d, 1H), 2.48 (q, 2H), 2.45 (d, 2H), 2.22-2.21 (m, 1H), 2.06 (s, 3H), 1.25 (t, 3H), 1.03 (t, 6H)

Synthesis of Compound 10

Compound 10 was synthesized in the same manner as in the synthesis of Compound 5 of Synthesis Example 1, except that Intermediate 10(1), instead of Intermediate 5(1), was used (Yield: 65%). This compound was identified using LC-MS and $^1$H NMR.

LC-MS m/z=666 (M+H)$^+$ $^1$H NMR (500 MHz, CDCl$_3$) δ=10.74 (s, 1H), 8.63 (d, 1H), 8.31 (d, 1H), 2.38 (q, 2H), 2.32 (d, 2H), 2.22-2.21 (m, 1H), 2.13 (s, 3H), 1.21 (t, 3H), 1.00 (t, 6H)

Synthesis Example 11: Synthesis of Compound 11

Compound 11 was synthesized according to Reaction Scheme 11 below:

<Reaction Scheme 11>

Compound 11

Synthesis of Intermediate 11(2)

Intermediate 11(2) was synthesized in the same manner as in the synthesis of Intermediate 5(2) of Synthesis Example 1, except that 4-methyl-pentan-2-one, instead of 3,3-dimethyl-2-butanone, was used (Yield: 16%). This compound was identified using LC-MS.

LC-MS m/z=262 (M+H)$^+$

Synthesis of Intermediate 11(1)

Intermediate 11(1) was synthesized in the same manner as in the synthesis of Intermediate 5(1) of Synthesis Example 1, except that Intermediate 11(2), instead of Intermediate 5(2), was used (Yield: 50%). This compound was identified using LC-MS.

LC-MS m/z=258 (M+H)$^+$ $^1$H NMR (500 MHz, CDCl$_3$) δ=8.59 (s, 1H), 7.72 (d, 1H), 7.41 (d, 1H), 6.54 (s, 1H), 2.53 (d, 2H), 2.49 (d, 2H), 1.96-1.92 (m, 2H), 1.03-0.98 (m, 12H).

Synthesis of Compound 11

Compound 11 was synthesized in the same manner as in the synthesis of Compound 5 of Synthesis Example 1, except that Intermediate 11(1), instead of Intermediate 5(1), was used (Yield: 60%). This compound was identified using LC-MS and $^1$H NMR.

LC-MS m/z=708 (M+H)$^+$ $^1$H NMR (500 MHz, CDCl$_3$) δ=10.46 (s, 1H), 8.31 (d, 1H), 8.12 (d, 1H), 6.77 (s, 1H), 2.49 (d, 2H), 2.47 (d, 2H), 1.95-1.91 (m, 2H), 1.04-1.00 (m, 12H).

Synthesis Example 12: Synthesis of Compound 12

Compound 12 was synthesized according to Reaction Scheme 12 below:

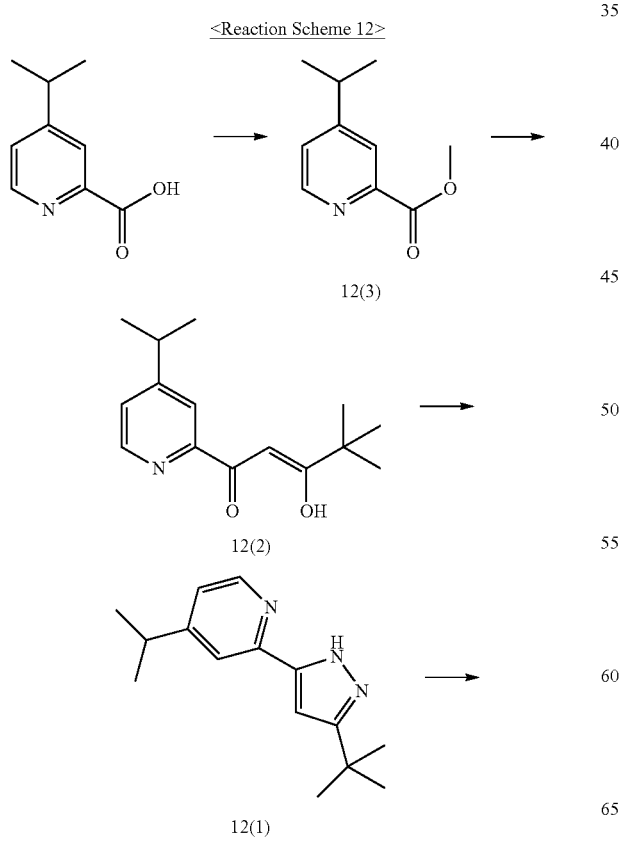

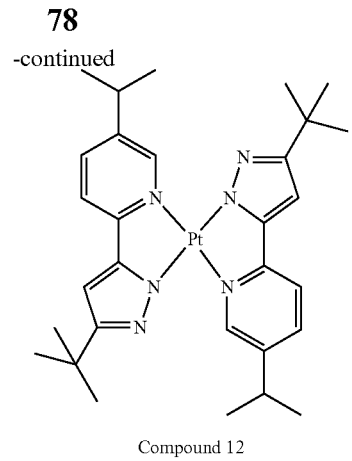

Compound 12

Synthesis of Intermediate 12(3)

Intermediate 12(3) was synthesized in the same manner as in the synthesis of Intermediate 5(3) of Synthesis Example 1, except that 4-isopropyl-pyridine-2-carboxylic acid, instead of 5-isobutyl-pyridine-2-carboxylic acid, was used (Yield: 96%). This compound was identified using LC-MS.

LC-MS m/z=180 (M+H)$^+$

Synthesis of Intermediate 12(2)

Intermediate 12(2) was synthesized in the same manner as in the synthesis of Intermediate 5(2) of Synthesis Example 1, except that Intermediate 5(3), instead of Intermediate 12(3), was used (Yield: 46%). This compound was identified using LC-MS.

LC-MS m/z=248 (M+H)$^+$

Synthesis of Intermediate 12(1)

Intermediate 12(1) was synthesized in the same manner as in the synthesis of Intermediate 5(1) of Synthesis Example 1, except that Intermediate 12(2), instead of Intermediate 5(2), was used (Yield: 50%). This compound was identified using LC-MS.

LC-MS m/z=245 (M+H)$^+$ $^1$H NMR (500 MHz, CDCl$_3$) δ=8.66 (d, 1H), 7.63 (s, 1H), 7.23 (d, 1H), 6.71 (s, 1H), 3.02-2.99 (m, 1H), 1.31 (s, 9H), 1.21 (d, 6H)

Synthesis of Compound 12

Compound 12 was synthesized in the same manner as in the synthesis of Compound 5 of Synthesis Example 1, except that Intermediate 12(1), instead of Intermediate 5(1), was used (Yield: 71%). This compound was identified using LC-MS and $^1$H NMR.

LC-MS m/z=680 (M+H)$^+$ $^1$H NMR (500 MHz, CDCl$_3$) δ=10.74 (d, 1H), 8.45 (s, 1H), 7.26-7.25 (m, 1H), 6.82 (s, 1H), 3.00-2.97 (m, 1H), 1.34 (s, 9H), 1.18 (d, 6H)

Synthesis Example 13: Synthesis of Compound 13

Compound 12 was synthesized according to Reaction Scheme 13 below:

<Reaction Scheme 13>

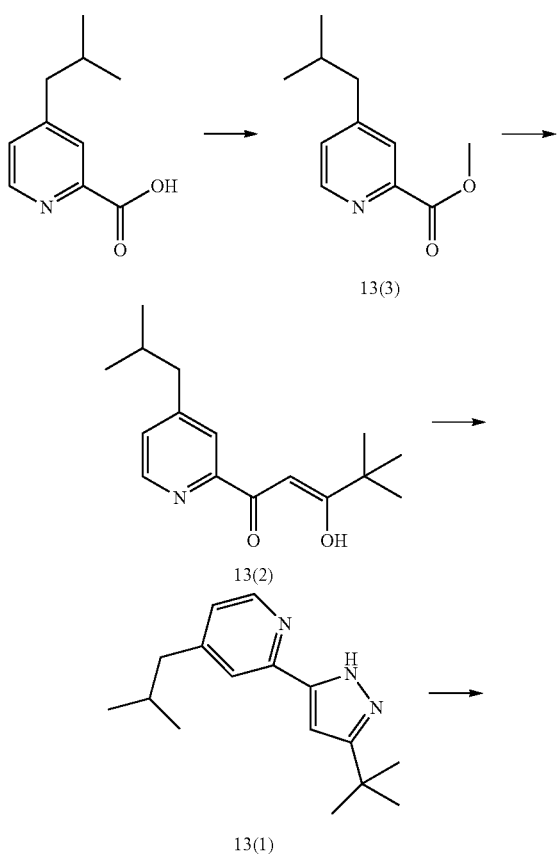

Synthesis of Intermediate 13(3)

Intermediate 13(3) was synthesized in the same manner as in the synthesis of Intermediate 5(3) of Synthesis Example 1, except that 4-isopropyl-pyridine-2-carboxylic acid, instead of 5-isobutyl-pyridine-2-carboxylic acid, was used (Yield: 95%). This compound was identified using LC-MS.
LC-MS m/z=194 (M+H)$^+$

Synthesis of Intermediate 13(2)

Intermediate 13(2) was synthesized in the same manner as in the synthesis of Intermediate 5(2) of Synthesis Example 1, except that Intermediate 13(3), instead of Intermediate 5(3), was used (Yield: 50%). This compound was identified using LC-MS.
LC-MS m/z=262 (M+H)$^+$

Synthesis of Intermediate 13(1)

Intermediate 13(1) was synthesized in the same manner as in the synthesis of Intermediate 5(1) of Synthesis Example 1, except that Intermediate 13(2), instead of Intermediate 5(2), was used (Yield: 50%). This compound was identified using LC-MS.
LC-MS m/z=258 (M+H)$^+$
$^1$H NMR (500 MHz, CDCl$_3$) δ=8.48 (d, 1H), 7.69 (s, 1H), 7.34 (d, 1H), 6.65 (s, 1H), 2.45 (d, 2H), 2.23-2.21 (m, 1H), 1.27 (s, 9H), 0.97 (d, 6H)

Synthesis of Compound 13

Compound 13 was synthesized in the same manner as in the synthesis of Compound 5 of Synthesis Example 1, except that Intermediate 13(1), instead of Intermediate 5(1), was used (Yield: 60%). This compound was identified using LC-MS and $^1$H NMR.
LC-MS m/z=708 (M+H)$^+$
$^1$H NMR (500 MHz, CDCl$_3$) δ=10.71 (d, 1H), 8.84 (s, 1H), 7.524 (d, 1H), 6.78 (s, 1H), 2.32 (d, 2H), 2.21-2.20 (m, 1H), 1.30 (s, 9H), 1.01 (d, 6H)

Synthesis Example 14: Synthesis of Compound 14

Compound 14 was synthesized according to Reaction Scheme 14 below:

<Reaction Scheme 14>

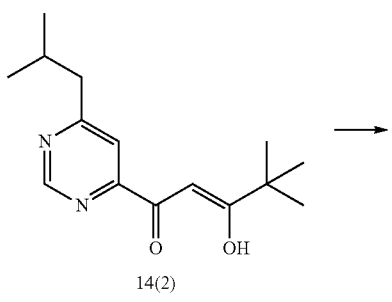

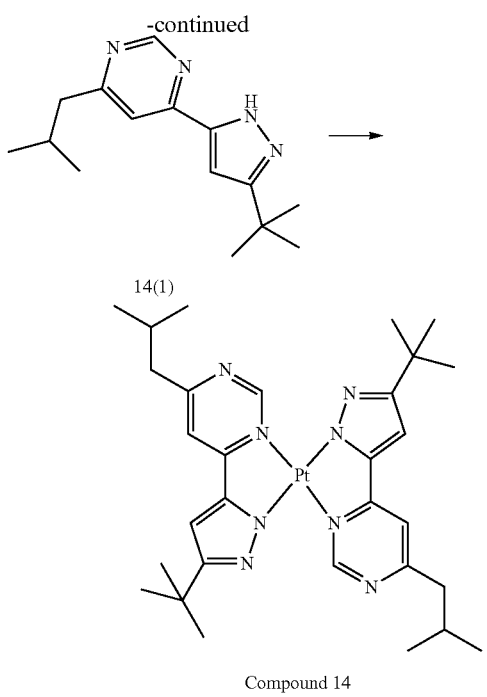

14(1)

Compound 14

Synthesis of Intermediate 14(3)

After 10 g (57.9 mmol) of 6-chloro-pyrimidine-4-carboxylic acid methyl ester was dissolved in 200 mL of a mixed solvent of toluene and water, 7.1 g (69.5 mmol) of (2-methylpropyl)boronic acid, 2.0 g (9.3 mmol) of Pd(OAc)$_2$, 4.2 g (15.0 mmol) of tricyclohexyl phosphine, and 4.3 g (202 mmol) of K$_3$PO$_4$ 4.3 g (202 mmol) were added to the solution and heated under reflux at about 100° C. for about 18 hours. After completion of the reaction, the reaction product was filtered using Celite, the solvent was removed by distillation under reduced pressure, and the product residue was extracted with 100 mL of distilled water and 300 mL of dichloromethane. The organic phase was dried using magnesium sulfate, and the solvent was removed by distillation under reduced pressure. The resulting product was purified by column chromatography to obtain 5.3 g (27.2 mmol) of Intermediate 14(3) (Yield: 47%).

LC-MS m/z=193 (M+H)$^+$

Synthesis of Intermediate 14(2)

Intermediate 14(2) was synthesized in the same manner as in the synthesis of Intermediate 5(2) of Synthesis Example 1, except that Intermediate 14(3), instead of Intermediate 5(3), was used (Yield: 40%). This compound was identified using LC-MS.

LC-MS m/z=263 (M+H)$^+$

Synthesis of Intermediate 14(1)

Intermediate 14(1) was synthesized in the same manner as in the synthesis of Intermediate 5(1) of Synthesis Example 1, except that Intermediate 14(2), instead of Intermediate 5(2), was used (Yield: 48%). This compound was identified using LC-MS.

LC-MS m/z=259 (M+H)$^+$ $^1$H NMR (500 MHz, CDCl$_3$) δ=9.07 (s, 1H), 7.45 (s, 1H), 6.81 (s, 1H), 2.62 (d, 2H), 1.98-1.93 (m, 1H), 1.32 (s, 9H), 0.97 (d, 6H)

Synthesis of Compound 14

Compound 14 was synthesized in the same manner as in the synthesis of Compound 5 of Synthesis Example 1, except that Intermediate 14(1), instead of Intermediate 5(1), was used (Yield: 76%). This compound was identified using LC-MS and $^1$H NMR.

LC-MS m/z=710 (M+H)$^+$ $^1$H NMR (500 MHz, CDCl$_3$) δ=10.85 (s, 1H), 8.60 (s, 1H), 6.85 (s, 1H), 2.71 (d, 2H), 2.01-1.96 (m, 1H), 1.30 (s, 9H), 1.03 (d, 6H)

Synthesis Example 15: Synthesis of Compound 15

Compound 15 was synthesized according to Reaction Scheme 15 below:

<Reaction Scheme 15>

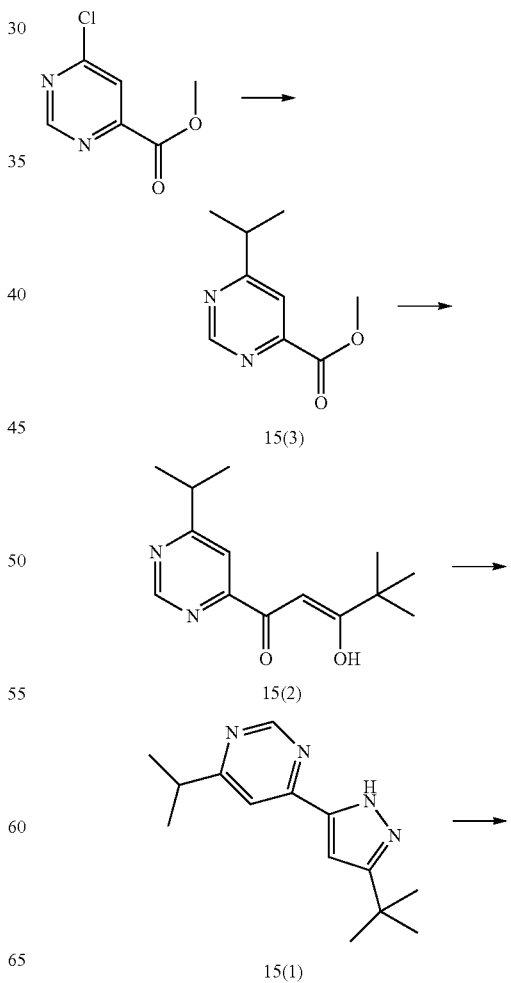

15(3)

15(2)

15(1)

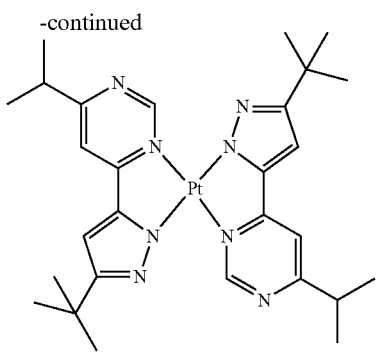

Compound 15

Synthesis of Intermediate 15(3)

Intermediate 15(3) was synthesized in the same manner as in the synthesis of Intermediate 14(3) of Synthesis Example 14, except that isopropylboronic acid, instead of (2-methylpropyl)boronic acid, was used (Yield: 42%). This compound was identified using LC-MS.

LC-MS m/z=181 (M+H)$^+$

Synthesis of Intermediate 15(2)

Intermediate 15(2) was synthesized in the same manner as in the synthesis of Intermediate 5(2) of Synthesis Example 1, except that Intermediate 15(3), instead of Intermediate 5(3), was used (Yield: 46%). This compound was identified using LC-MS.

LC-MS m/z=249 (M+H)$^+$

Synthesis of Intermediate 15(1)

Intermediate 15(1) was synthesized in the same manner as in the synthesis of Intermediate 5(1) of Synthesis Example 1, except that Intermediate 15(2), instead of Intermediate 5(2), was used (Yield: 55%). This compound was identified using LC-MS.

LC-MS m/z=245 (M+H)$^+$

Synthesis of Compound 15

Compound 15 was synthesized in the same manner as in the synthesis of Compound 5 of Synthesis Example 1, except that Intermediate 15(1), instead of Intermediate 5(1), was used (Yield: 65%). This compound was identified using LC-MS and $^1$H NMR.

LC-MS m/z=682 (M+H)$^+$ $^1$H NMR (500 MHz, CDCl$_3$) δ=10.77 (s, 1H), 8.43 (s, 1H), 6.79 (s, 1H), 3.12-3.08 (m, 1H), 1.32 (s, 9H), 1.24 (d, 6H)

Synthesis Example 16: Synthesis of Compound 16

Compound 16 was synthesized according to Reaction Scheme 16 below:

<Reaction Scheme 16>

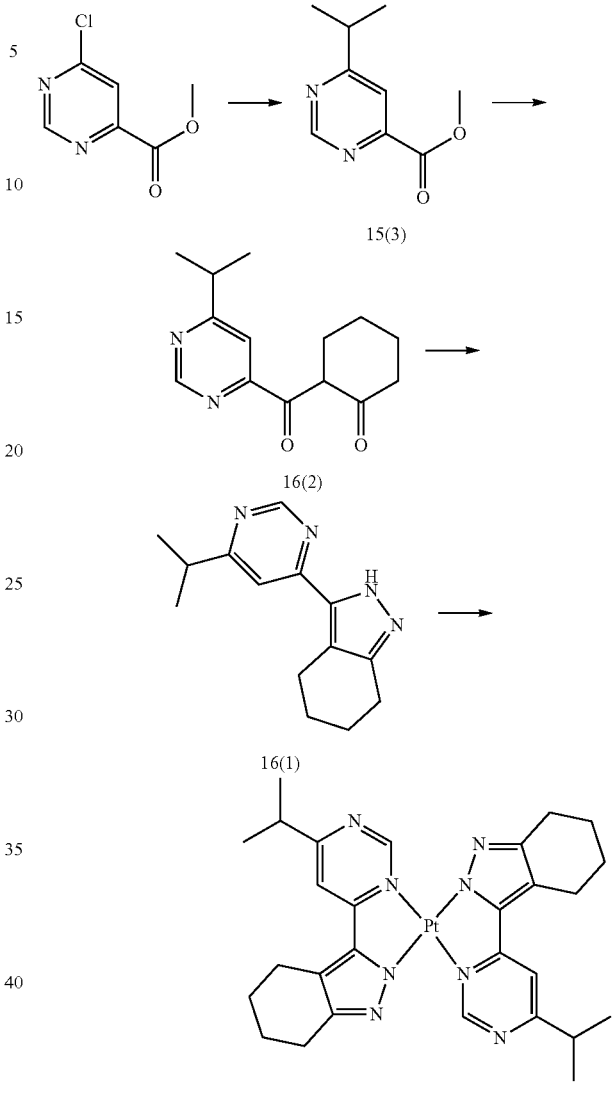

Compound 16

Synthesis of Intermediate 16(2)

Intermediate 16(2) was synthesized in the same manner as in the synthesis of Intermediate 5(2) of Synthesis Example 1, except that Intermediate 15(3) and cyclohexanone, respectively, instead of Intermediate 5(3) and 3,3-dimethyl-2-butanone, were used (Yield: 66%). This compound was identified using LC-MS.

LC-MS m/z=247 (M+H)$^+$

Synthesis of Intermediate 16(1)

Intermediate 16(1) was synthesized in the same manner as in the synthesis of Intermediate 5(1) of Synthesis Example 1, except that Intermediate 16(2), instead of Intermediate 5(2), was used (Yield: 52%). This compound was identified using LC-MS.

LC-MS m/z=243 (M+H)$^+$

¹H NMR (500 MHz, CDCl₃) δ=9.13 (s, 1H), 7.50 (s, 1H), 3.10-3.05 (m, 1H), 2.96-2.84 (m, 2H), 2.78-2.75 (m, 2H), 1.87-1.82 (m, 4H), 1.32 (s, 9H), 1.24 (d, 6H)

Synthesis of Compound 16

Compound 16 was synthesized in the same manner as in the synthesis of Compound 5 of Synthesis Example 1, except that Intermediate 16(1), instead of Intermediate 5(1), was used (Yield: 50%). This compound was identified using LC-MS and ¹H NMR.

LC-MS m/z=678 (M+H)⁺
¹H NMR (500 MHz, CDCl₃) δ=10.70 (s, 1H), 8.39 (s, 1H), 3.12-3.08 (m, 1H), 2.91-2.80 (m, 2H), 2.75-2.71 (m, 2H), 1.85-1.81 (m, 4H), 1.31 (s, 9H), 1.26 (d, 6H)

Synthesis Example 17: Synthesis of Compound 17

Compound 17 was synthesized according to Reaction Scheme 17 below:

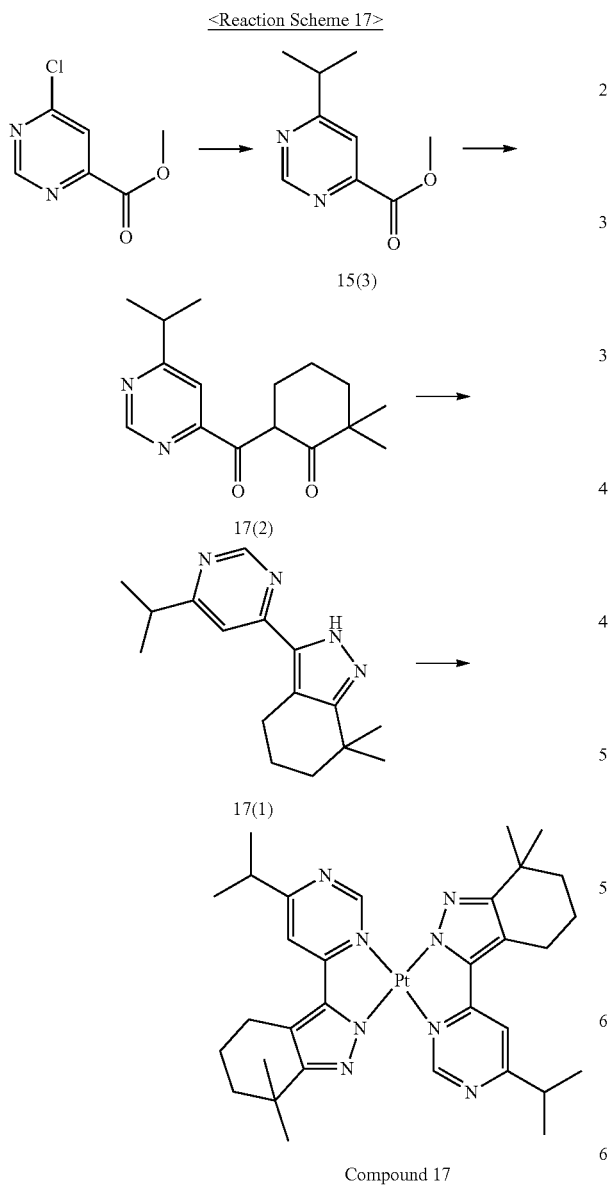

Synthesis of Intermediate 17(2)

Intermediate 17(2) was synthesized in the same manner as in the synthesis of Intermediate 8(2) of Synthesis Example 8, except that Intermediate 15(3), instead of Intermediate 5(3), was used (Yield: 65%). This compound was identified using LC-MS.

LC-MS m/z=275 (M+H)⁺

Synthesis of Intermediate 17(1)

Intermediate 17(1) was synthesized in the same manner as in the synthesis of Intermediate 5(1) of Synthesis Example 1, except that Intermediate 17(2), instead of Intermediate 5(2), was used (Yield: 60%). This compound was identified using LC-MS.

LC-MS m/z=271 (M+H)⁺

Synthesis of Compound 17

Compound 17 was synthesized in the same manner as in the synthesis of Compound 5 of Synthesis Example 1, except that Intermediate 17(1), instead of Intermediate 5(1), was used (Yield: 58%). This compound was identified using LC-MS and ¹H NMR.

LC-MS m/z=734 (M+H)⁺
¹H NMR (500 MHz, CDCl₃) δ=10.72 (s, 1H), 8.36 (s, 1H), 3.16-3.11 (m, 1H), 2.55-2.43 (m, 2H), 1.85-1.81 (m, 4H), 1.36-1.31 (m, 15H), 1.26 (d, 6H)

Synthesis Example 18: Synthesis of Compound 18

Compound 18 was synthesized according to Reaction Scheme 18 below:

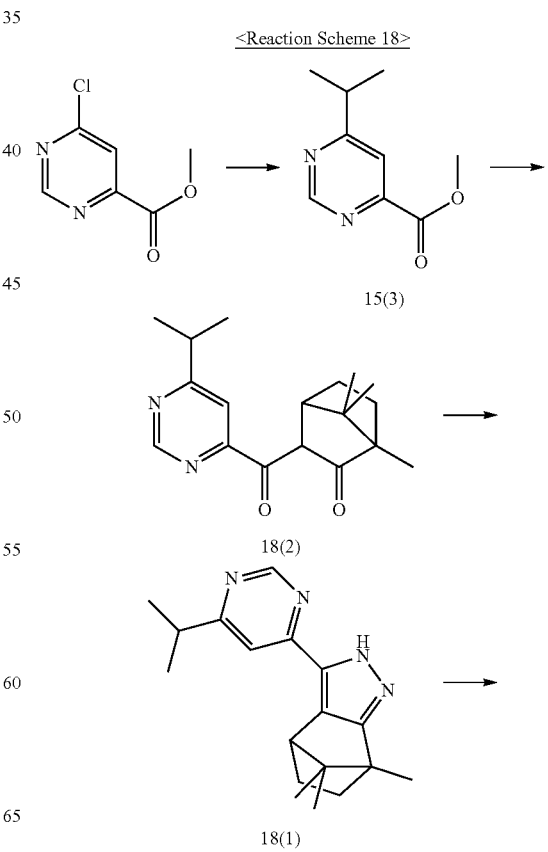

-continued

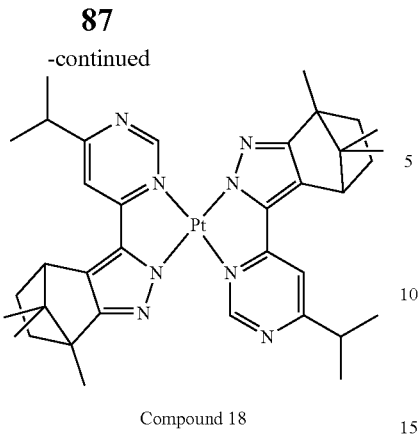

Compound 18

Synthesis of Intermediate 18(2)

Intermediate 18(2) was synthesized in the same manner as in the synthesis of Intermediate 9(2) of Synthesis Example 9, except that Intermediate 15(3), instead of Intermediate 5(3), was used (Yield: 60%). This compound was identified using LC-MS.

LC-MS m/z=301 (M+H)$^+$

Synthesis of Intermediate 18(1)

Intermediate 18(1) was synthesized in the same manner as in the synthesis of Intermediate 5(1) of Synthesis Example 1, except that Intermediate 18(2), instead of Intermediate 5(2), was used (Yield: 50%). This compound was identified using LC-MS.

LC-MS m/z=297 (M+H)$^+$

Synthesis of Compound 18

Compound 18 was synthesized in the same manner as in the synthesis of Compound 5 of Synthesis Example 1, except that Intermediate 18(1), instead of Intermediate 5(1), was used (Yield: 72%). This compound was identified using LC-MS and $^1$H NMR.

LC-MS m/z=786 (M+H)$^+$ $^1$H NMR (500 MHz, CDCl$_3$) δ=10.68 (s, 1H), 8.31 (s, 1H), 3.14-3.07 (m, 1H), 2.24-2.21 (m, 1H), 1.68~1.64 (m, 4H), 1.57 (s, 3H), 1.26 (d, 6H), 1.21 (s, 6H).

Synthesis Example 19: Synthesis of Compound 19

Compound 19 was synthesized according to Reaction Scheme 19 below:

<Reaction Scheme 19>

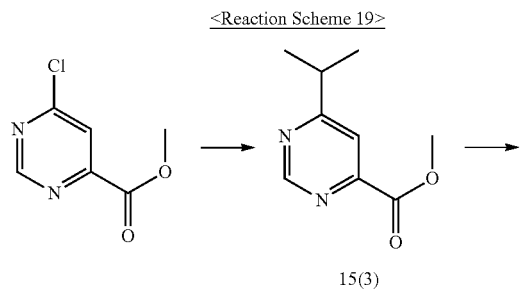

15(3)

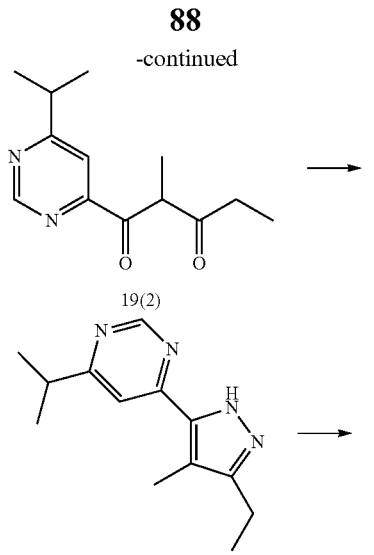

19(2)

19(1)

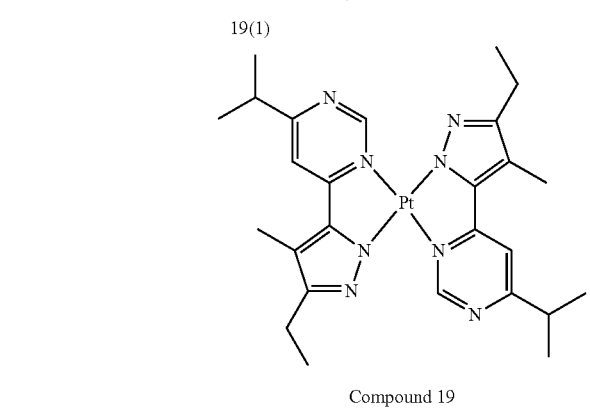

Compound 19

Synthesis of Intermediate 19(2)

Intermediate 19(2) was synthesized in the same manner as in the synthesis of Intermediate 10(2) of Synthesis Example 10, except that Intermediate 15(3), instead of Intermediate 5(3), was used (Yield: 38%). This compound was identified using LC-MS.

LC-MS m/z=235 (M+H)$^+$

Synthesis of Intermediate 19(1)

Intermediate 19(1) was synthesized in the same manner as in the synthesis of Intermediate 5(1) of Synthesis Example 1, except that Intermediate 19(2), instead of Intermediate 5(2), was used (Yield: 52%). This compound was identified using LC-MS.

LC-MS m/z=231 (M+H)$^+$

Synthesis of Compound 19

Compound 19 was synthesized in the same manner as in the synthesis of Compound 5 of Synthesis Example 1, except that Intermediate 19(1), instead of Intermediate 5(1), was used (Yield: 55%). This compound was identified using LC-MS and $^1$H NMR.

LC-MS m/z=654 (M+H)$^+$ $^1$H NMR (500 MHz, CDCl$_3$) δ=10.70 (s, 1H), 8.33 (s, 1H), 3.13-3.05 (m, 1H), 2.68 (q, 2H), 2.41 (s, 3H), 1.36 (t, 3H), 1.22 (d, 6H)

Synthesis Example 20: Synthesis of Compound 20

Compound 20 was synthesized according to Reaction Scheme 20 below:

<Reaction Scheme 20>

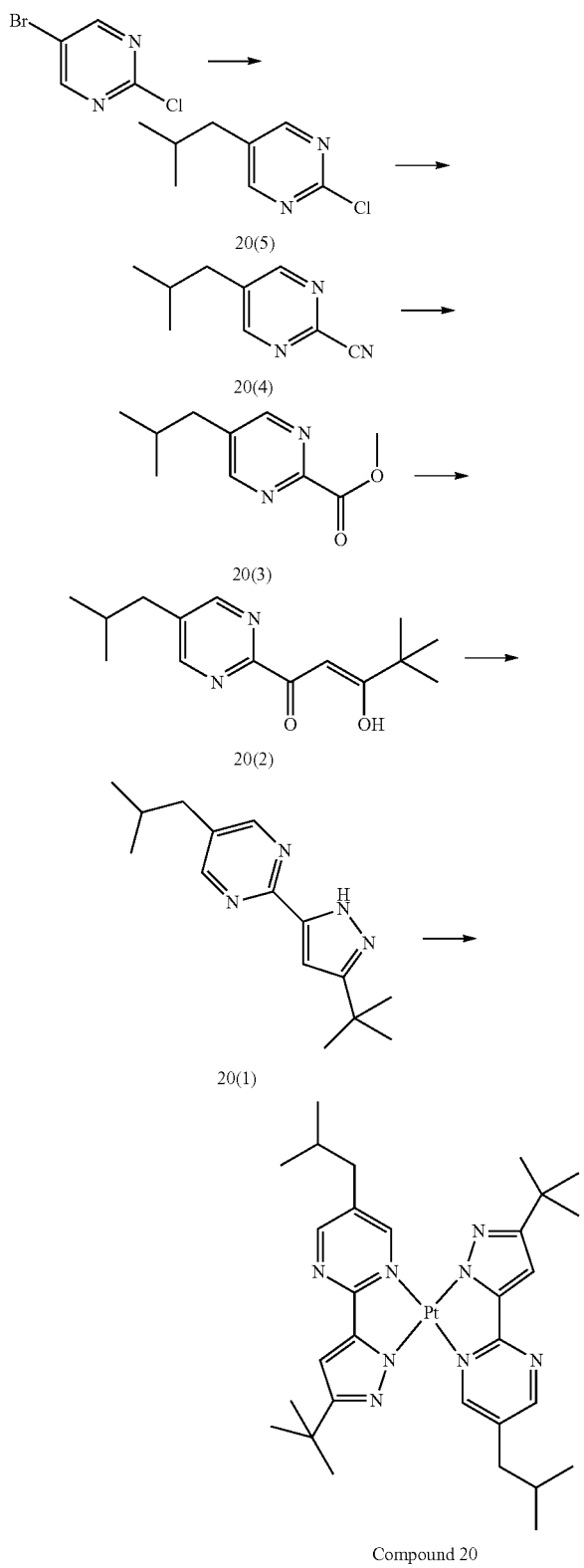

Compound 20

Synthesis of Intermediate 20(5)

After 5 g (25.9 mmol) of 5-bromo-2-chloropyrimidine, 3.1 g (31.0 mmol) of (2-methylpropyl)boronic acid, 0.9 g (3.8 mmol) of $Pd(OAc)_2$, 1.4 g (5.2 mmol) of tricyclohexyl phosphine, and 16.5 g (78 mmol) of $K_3PO_4$ were dissolved in a mixed solvent of 90 mL of toluene and 6 mL of water, the solution was heated under reflux at about 80° C. for about 18 hours. After completion of the reaction, the reaction product was filtered using Celite, the filtrate was distilled under reduced pressure to remove the solvent, and the product residue was purified by column chromatography to obtain 2.2 g (12.7 mmol) of Intermediate 20(5) (Yield: 49%).

LC-MS m/z=171 $(M+H)^+$ $^1H$ NMR (500 MHz, $CDCl_3$) δ=8.43 (s, 2H), 2.47 (d, 2H), 1.91-1.83 (m, 1H), 0.94 (d, 6H).

Synthesis of Intermediate 20(4)

A quantity of 2.2 g (12.9 mmol) of Intermediate 20(5) was dissolved in a mixed solvent of 12 mL of dimethyl sulfoxide (DMSO) and 12 mL of water, and 0.7 g (14.1 mmol) of NaCN and 0.3 g (2.6 mmol) of DABCO were then added to the solution. The resulting solution was then stirred at room temperature for about 2 hours, and then heated at about 80° C. for about 16 hours. After completion of the reaction, the reaction product was extracted with water and ethyl acetate (EA). The ethyl acetate extracts were dried using magnesium sulfate, and the solvent was removed by distillation under reduced pressure to obtain 2.0 g (12.2 mmol) of Intermediate 20(4) (Yield: 95%).

LC-MS m/z=162 $(M+H)^+$ $^1H$ NMR (500 MHz, $CDCl_3$) δ=8.64 (s, 2H), 2.57 (d, 2H), 1.96-1.91 (m, 1H), 0.96 (d, 6H).

Synthesis of Intermediate 20(3)

After 2.0 g (12.2 mmol) of Intermediate 20(4) was dissolved in 40 mL of methanol, 10 mL of a 35% HCl solution was added to the methanol solution, and the resulting mixture was then heated under reflux at about 80° C. for about 18 hours. After completion of the reaction, the reaction product was distilled under reduced pressure to obtain a concentrated reaction mixture, which was dissolved in dichloromethane and then washed with a saturated sodium hydrogen carbonate aqueous solution for neutralization. The organic layer was collected and dried using magnesium sulfate. Column chromatography was used to obtain 1.0 g (5.1 mmol) of Intermediate 20(3) (Yield: 42%).

LC-MS m/z=195 $(M+H)^+$

Synthesis of Intermediate 20(2)

Intermediate 20(2) was synthesized in the same manner as in the synthesis of Intermediate 5(2) of Synthesis Example 1, except that Intermediate 20(3) and lithium bis(trimethylsilyl)amide (LiHMDS), respectively, instead of Intermediate 5(3) and NaH, were used (Yield: 60%). This compound was identified using LC-MS.

LC-MS m/z=263 $(M+H)^+$

Synthesis of Intermediate 20(1)

Intermediate 20(1) was synthesized in the same manner as in the synthesis of Intermediate 5(1) of Synthesis Example 1, except that Intermediate 20(2), instead of Intermediate 5(2), was used (Yield: 55%). This compound was identified using LC-MS.

LC-MS m/z=259 (M+H)+

Synthesis of Compound 20

Compound 20 was synthesized in the same manner as in the synthesis of Compound 5 of Synthesis Example 1, except that Intermediate 20(1), instead of Intermediate 5(1), was used (Yield: 75%). This compound was identified using LC-MS and $^1$H NMR.

LC-MS m/z=710 (M+H)+
$^1$H NMR (500 MHz, CDCl$_3$) δ=10.59 (s, 1H), 8.49 (s, 1H), 6.78 (s, 1H), 2.43 (d, 2H), 2.26-2.23 (m, 1H), 1.29 (s, 9H), 1.05 (s, 6H)

Synthesis Example 21: Synthesis of Compound 21

Compound 21 was synthesized according to Reaction Scheme 21 below:

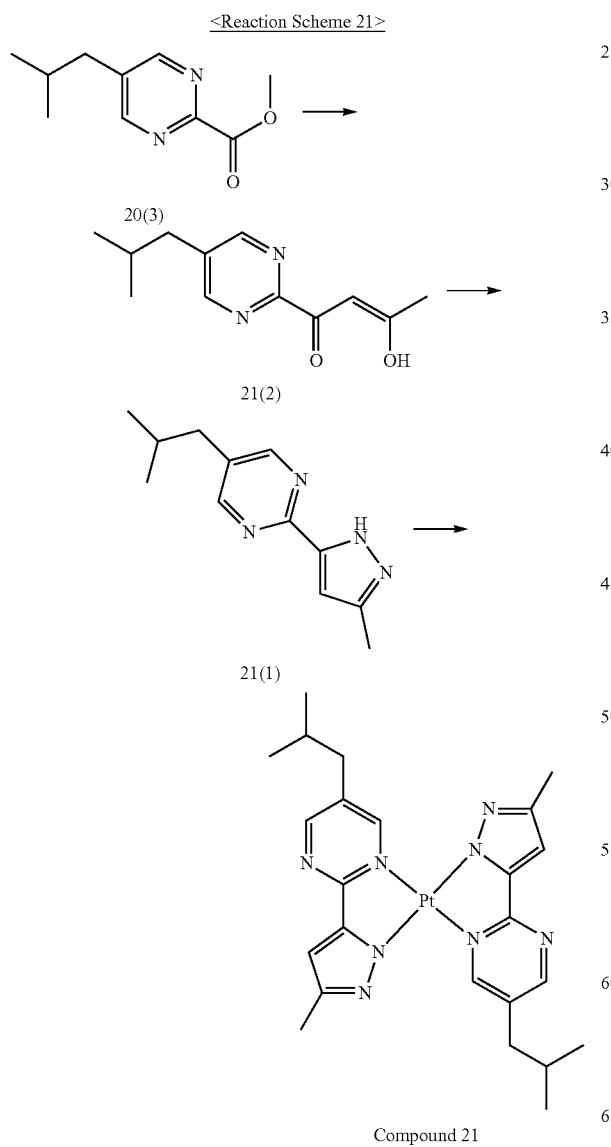

Synthesis of Intermediate 21(2)

Intermediate 21(2) was synthesized in the same manner as in the synthesis of Intermediate 4(2) of Synthesis Example 5, except that Intermediate 20(3), instead of Intermediate 5(3), was used (Yield: 21%). This compound was identified using LC-MS.

LC-MS m/z=221 (M+H)+

Synthesis of Intermediate 21(1)

Intermediate 2(1) was synthesized in the same manner as in the synthesis of Intermediate 5(1) of Synthesis Example 1, except that Intermediate 21(2), instead of Intermediate 5(2), was used (Yield: 55%). This compound was identified using LC-MS.

LC-MS m/z=217 (M+H)+

Synthesis of Compound 21

Compound 21 was synthesized in the same manner as in the synthesis of Compound 5 of Synthesis Example 1, except that Intermediate 21(1), instead of Intermediate 5(1), was used (Yield: 60%). This compound was identified using LC-MS and $^1$H NMR.

LC-MS m/z=626 (M+H)+
$^1$H NMR (500 MHz, CDCl$_3$) δ=10.68 (s, 1H), 8.66 (s, 1H), 6.80 (s, 1H), 2.76 (s, 3H), 2.27-2.24 (m, 1H), 1.03 (s, 6H)

Synthesis Example 22: Synthesis of Compound 22

Compound 22 was synthesized according to Reaction Scheme 22 below:

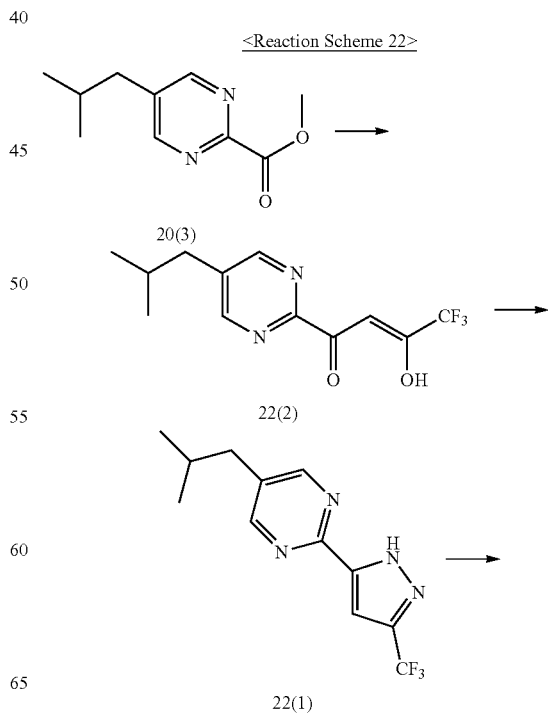

-continued

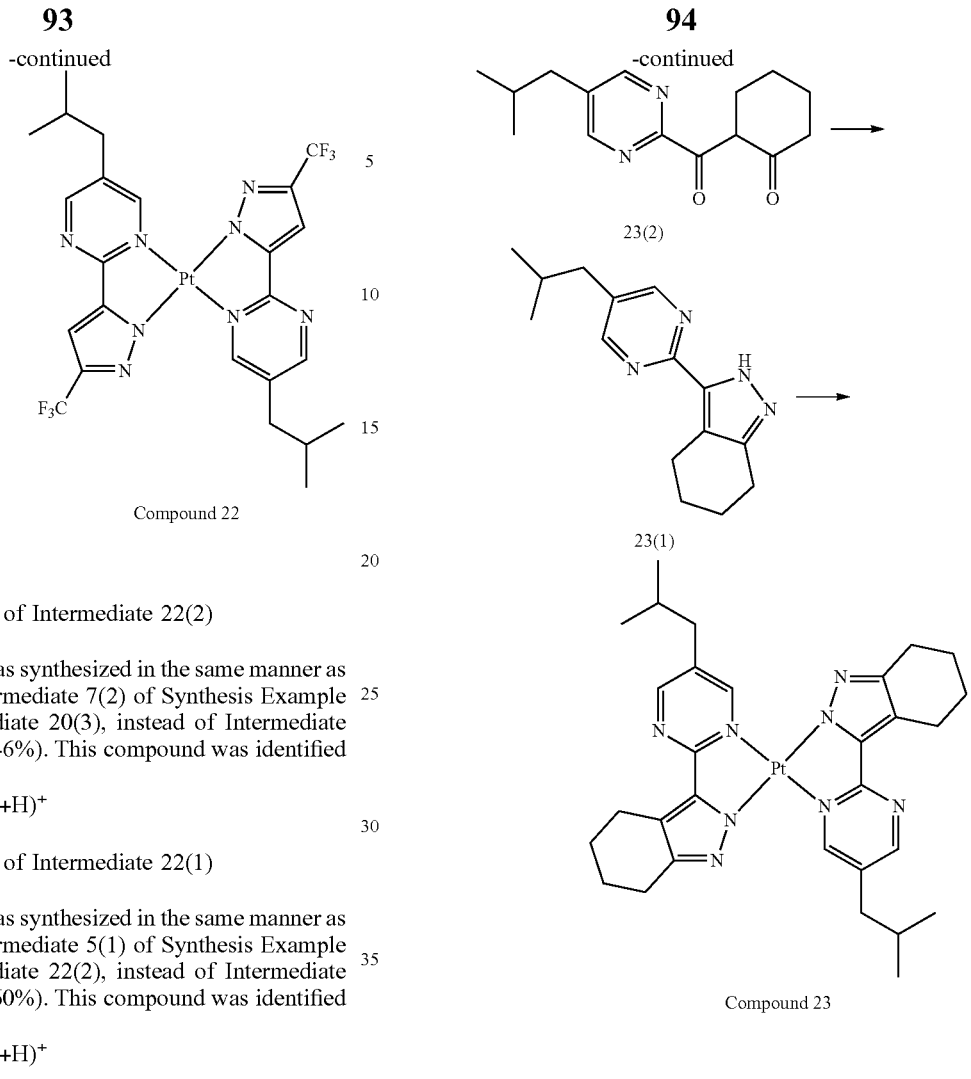

Compound 22

Compound 23

Synthesis of Intermediate 22(2)

Intermediate 22(2) was synthesized in the same manner as in the synthesis of Intermediate 7(2) of Synthesis Example 7, except that Intermediate 20(3), instead of Intermediate 5(3), was used (Yield: 46%). This compound was identified using LC-MS.

LC-MS m/z=275 (M+H)$^+$

Synthesis of Intermediate 22(1)

Intermediate 22(1) was synthesized in the same manner as in the synthesis of Intermediate 5(1) of Synthesis Example 1, except that Intermediate 22(2), instead of Intermediate 5(2), was used (Yield: 60%). This compound was identified using LC-MS.

LC-MS m/z=271 (M+H)$^+$

Synthesis of Compound 22

Compound 22 was synthesized in the same manner as in the synthesis of Compound 5 of Synthesis Example 1, except that Intermediate 22(1), instead of Intermediate 5(1), was used (Yield: 53%). This compound was identified using LC-MS and $^1$H NMR.

LC-MS m/z=734 (M+H)$^+$ $^1$H NMR (500 MHz, CDCl$_3$) δ=10.71 (s, 1H), 8.57 (s, 1H), 6.79 (s, 1H), 2.25-2.23 (m, 1H), 1.03 (s, 6H)

Synthesis Example 23: Synthesis of Compound 23

Compound 23 was synthesized according to Reaction Scheme 23 below:

<Reaction Scheme 23>

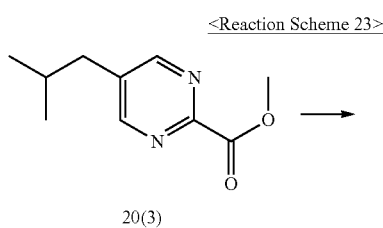

20(3)

Synthesis of Intermediate 23(2)

Intermediate 23(2) was synthesized in the same manner as in the synthesis of Intermediate 16(2) of Synthesis Example 16, except that Intermediate 20(3), instead of Intermediate 15(3), was used (Yield: 53%). This compound was identified using LC-MS.

LC-MS m/z=261 (M+H)$^+$

Synthesis of Intermediate 23(1)

Intermediate 23(1) was synthesized in the same manner as in the synthesis of Intermediate 5(1) of Synthesis Example 1, except that Intermediate 23(2), instead of Intermediate 5(2), was used (Yield: 70%). This compound was identified using LC-MS.

LC-MS m/z=257 (M+H)$^+$

Synthesis of Compound 23

Compound 23 was synthesized in the same manner as in the synthesis of Compound 5 of Synthesis Example 1, except that Intermediate 23(1), instead of Intermediate 5(1), was used (Yield: 60%). This compound was identified using LC-MS and $^1$H NMR.

LC-MS m/z=706 (M+H)$^+$ $^1$H NMR (500 MHz, CDCl$_3$) δ=10.76 (s, 1H), 8.59 (s, 1H), 6.79 (s, 1H), 2.90-2.82 (m, 2H), 2.75-2.71 (m, 2H), 2.25-2.23 (m, 1H), 1.87-1.82 (m, 4H), 1.03 (s, 6H)

Synthesis Example 24: Synthesis of Compound 24

Compound 24 was synthesized according to Reaction Scheme 24 below:

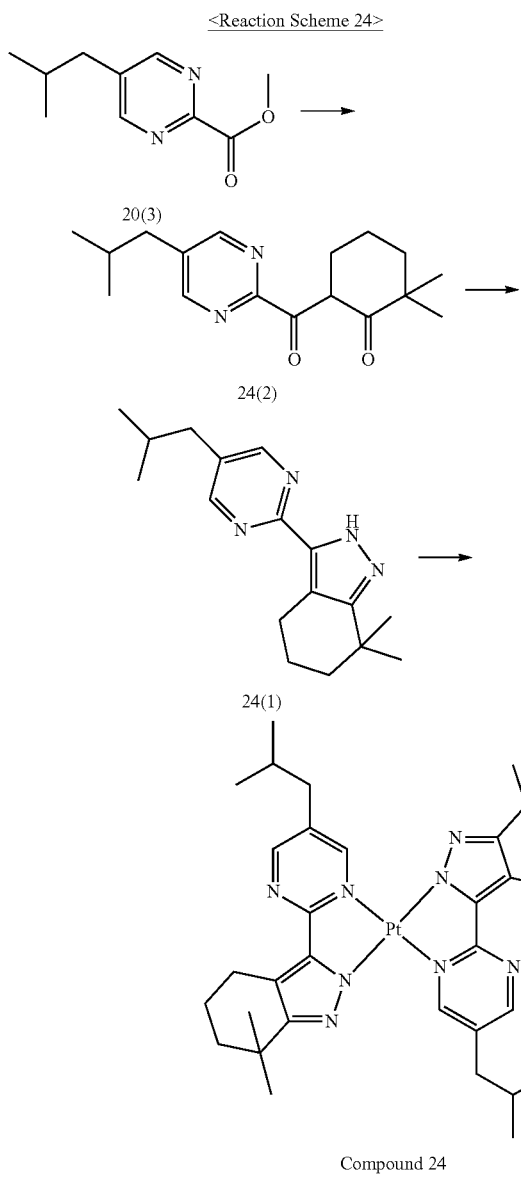

Compound 24

Synthesis of Intermediate 24(2)

Intermediate 24(2) was synthesized in the same manner as in the synthesis of Intermediate 8(2) of Synthesis Example 8, except that Intermediate 20(3), instead of Intermediate 5(3), was used (Yield: 55%). This compound was identified using LC-MS.

LC-MS m/z=289 (M+H)$^+$

Synthesis of Intermediate 24(1)

Intermediate 24(1) was synthesized in the same manner as in the synthesis of Intermediate 5(1) of Synthesis Example 1, except that Intermediate 8(2), instead of Intermediate 5(2), was used (Yield: 70%). This compound was identified using LC-MS.

LC-MS m/z=285 (M+H)$^+$

Synthesis of Compound 24

Compound 24 was synthesized in the same manner as in the synthesis of Compound 5 of Synthesis Example 1, except that Intermediate 8(1), instead of Intermediate 5(1), was used (Yield: 56%). This compound was identified using LC-MS and $^1$H NMR.

LC-MS m/z=762 (M+H)$^+$ $^1$H NMR (500 MHz, CDCl$_3$) δ=10.58 (s, 1H), 8.60 (s, 1H), 2.55-2.46 (m, 4H), 1.97-1.94 (m, 1H), 1.61-1.54 (m, 4H), 1.26 (s, 6H), 1.00 (d, 6H).

Synthesis Example 25: Synthesis of Compound 25

Compound 25 was synthesized according to Reaction Scheme 25 below:

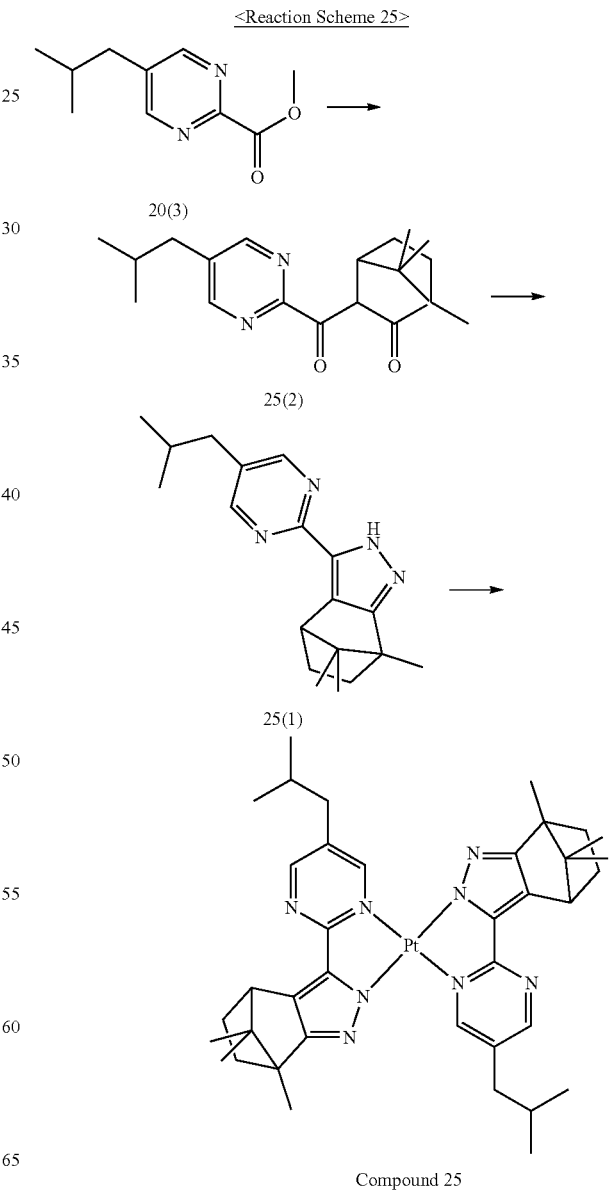

Compound 25

Synthesis of Intermediate 25(2)

Intermediate 25(2) was synthesized in the same manner as in the synthesis of Intermediate 9(2) of Synthesis Example 9, except that Intermediate 20(3), instead of Intermediate 5(3), was used (Yield: 60%). This compound was identified using LC-MS.

LC-MS m/z=315 (M+H)$^+$

Synthesis of Intermediate 25(1)

Intermediate 25(1) was synthesized in the same manner as in the synthesis of Intermediate 5(1) of Synthesis Example 1, except that Intermediate 25(2), instead of Intermediate 5(2), was used (Yield: 62%). This compound was identified using LC-MS.

LC-MS m/z=311 (M+H)$^+$

Synthesis of Compound 25

Compound 25 was synthesized in the same manner as in the synthesis of Compound 5 of Synthesis Example 1, except that Intermediate 25(1), instead of Intermediate 5(1), was used (Yield: 61%). This compound was identified using LC-MS and $^1$H NMR.

LC-MS m/z=813 (M+H)$^+$ $^1$H NMR (500 MHz, CDCl$_3$) δ=10.67 (s, 1H), 8.62 (s, 1H), 2.86 (br s, 1H), 2.79 (d, 2H), 2.24-2.21 (m, 1H). 1.68~1.64 (m, 4H), 1.62 (s, 3H), 1.21 (s, 6H), 1.04 (s, 6H)

Synthesis Example 26: Synthesis of Compound 26

Compound 26 was synthesized according to Reaction Scheme 26 below:

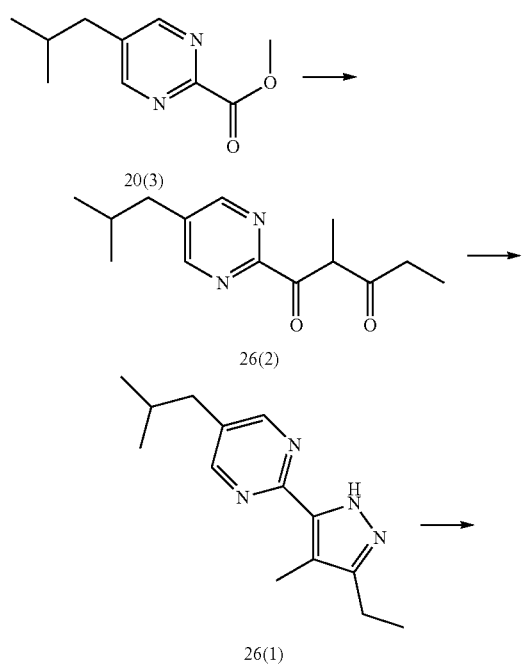

<Reaction Scheme 26>

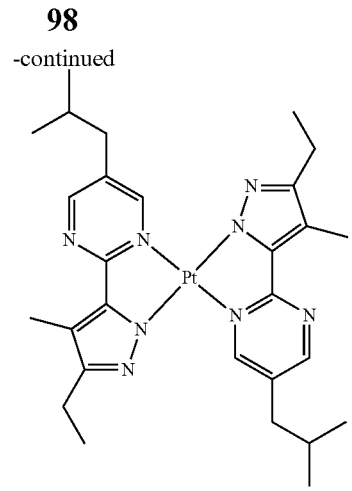

Compound 26

Synthesis of Intermediate 26(2)

Intermediate 26(2) was synthesized in the same manner as in the synthesis of Intermediate 10(2) of Synthesis Example 10, except that Intermediate 20(3), instead of Intermediate 5(3), was used (Yield: 47%). This compound was identified using LC-MS.

LC-MS m/z=249 (M+H)$^+$

Synthesis of Intermediate 26(1)

Intermediate 26(1) was synthesized in the same manner as in the synthesis of Intermediate 5(1) of Synthesis Example 1, except that Intermediate 26(2), instead of Intermediate 5(2), was used (Yield: 52%). This compound was identified using LC-MS.

LC-MS m/z=245 (M+H)$^+$

Synthesis of Compound 26

Compound 26 was synthesized in the same manner as in the synthesis of Compound 5 of Synthesis Example 1, except that Intermediate 26(1), instead of Intermediate 5(1), was used (Yield: 55%). This compound was identified using LC-MS and $^1$H NMR.

LC-MS m/z=682 (M+H)$^+$ $^1$H NMR (500 MHz, CDCl$_3$) δ=10.75 (s, 1H), 8.58 (s, 1H), 2.69 (q, 2H), 2.58 (d, 2H), 2.40 (s, 3H), 2.05-2.02 (m, 1H), 1.37 (t, 3H), 1.02 (d, 6H).

Synthesis Example 27: Synthesis of Compound 27

Compound 27 was synthesized according to Reaction Scheme 27 below:

<Reaction Scheme 27>

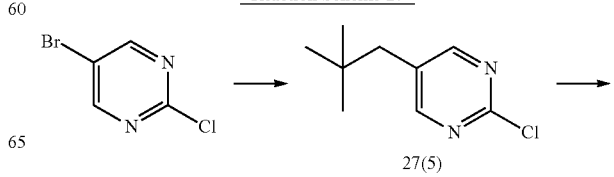

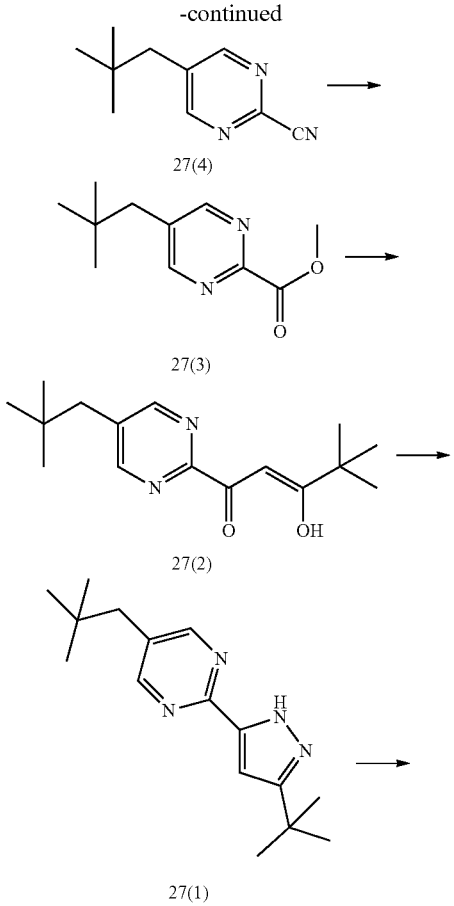

Compound 27

Synthesis of Intermediate 27(5)

Intermediate 27(5) was synthesized in the same manner as in the synthesis of Intermediate 20(5) of Synthesis Example 20, except that neopentylboronic acid, instead of (2-methylpropyl)boronic acid, was used (Yield: 42%). This compound was identified using LC-MS.
LC-MS m/z=185 (M+H)$^+$ Synthesis of Intermediate 27(4)

Intermediate 27(4) was synthesized in the same manner as in the synthesis of Intermediate 20(4) of Synthesis Example 20, except that Intermediate 27(5), instead of Intermediate 20(5), was used (Yield: 96%). This compound was identified using LC-MS.
LC-MS m/z=176 (M+H)$^+$ Synthesis of Intermediate 27(3)

Intermediate 27(3) was synthesized in the same manner as in the synthesis of Intermediate 20(3) of Synthesis Example 20, except that Intermediate 27(4), instead of Intermediate 20(4), was used (Yield: 51%). This compound was identified using LC-MS.
LC-MS m/z=209 (M+H)$^+$ Synthesis of Intermediate 27(2)

Intermediate 27(2) was synthesized in the same manner as in the synthesis of Intermediate 20(2) of Synthesis Example 20, except that Intermediate 27(3), instead of Intermediate 20(3), was used (Yield: 50%). This compound was identified using LC-MS.
LC-MS m/z=277 (M+H)$^+$ Synthesis of Intermediate 27(1)

Intermediate 27(1) was synthesized in the same manner as in the synthesis of Intermediate 20(1) of Synthesis Example 20, except that Intermediate 27(2), instead of Intermediate 20(2), was used (Yield: 62%). This compound was identified using LC-MS.
LC-MS m/z=273 (M+H)$^+$ Synthesis of Compound 27

Compound 27 was synthesized in the same manner as in the synthesis of Compound 20 of Synthesis Example 20, except that Intermediate 27(1), instead of Intermediate 20(1), was used (Yield: 76%). This compound was identified using LC-MS and $^1$H NMR.
LC-MS m/z=738 (M+H)$^+$
$^1$H NMR (500 MHz, CDCl$_3$) δ=10.68 (s, 1H), 8.52 (s, 1H), 6.81 (s, 1H), 2.47 (s, 2H), 1.34 (s, 9H), 1.06 (s, 9H)

Synthesis Example 28: Synthesis of Compound 28

Compound 28 was synthesized according to Reaction Scheme 28 below:

<Reaction Scheme 28>

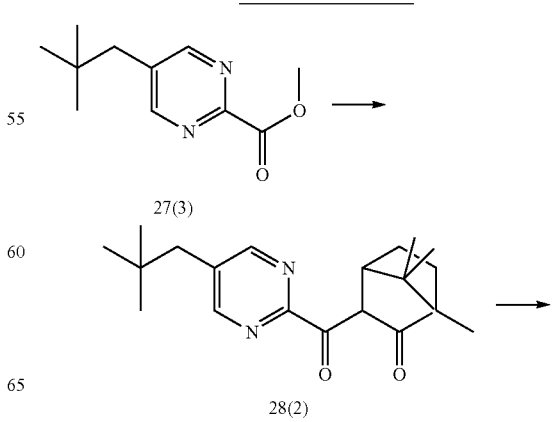

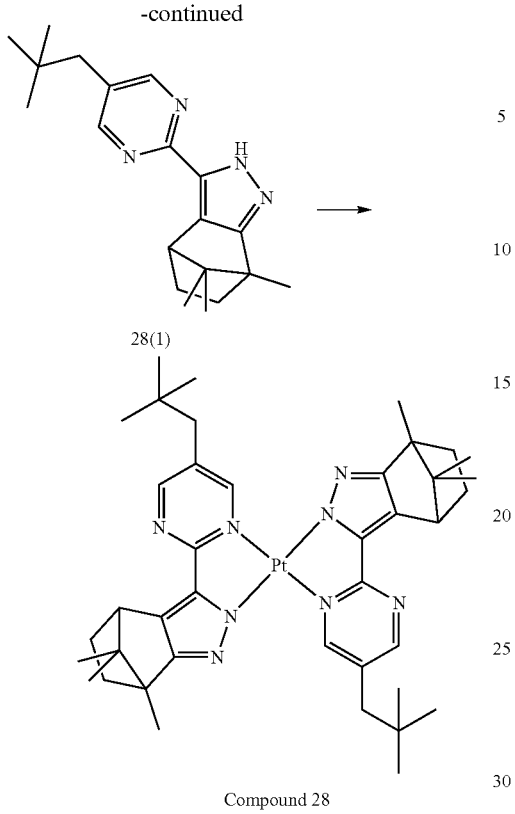

Compound 28

Synthesis of Intermediate 28(2)

Intermediate 28(2) was synthesized in the same manner as in the synthesis of Intermediate 9(2) of Synthesis Example 9, except that Intermediate 27(3), instead of Intermediate 5(3), was used (Yield: 51%). This compound was identified using LC-MS.

LC-MS m/z=329 (M+H)⁺

Synthesis of Intermediate 28(1)

Intermediate 28(1) was synthesized in the same manner as in the synthesis of Intermediate 5(1) of Synthesis Example 1, except that Intermediate 28(2), instead of Intermediate 5(2), was used (Yield: 66%). This compound was identified using LC-MS.

LC-MS m/z=325 (M+H)⁺

Synthesis of Compound 28

Compound 28 was synthesized in the same manner as in the synthesis of Compound 5 of Synthesis Example 1, except that Intermediate 28(1), instead of Intermediate 5(1), was used (Yield: 63%). This compound was identified using LC-MS and ¹H NMR.

LC-MS m/z=814 (M+H)⁺

¹H NMR (500 MHz, CDCl₃) δ=10.72 (s, 1H), 8.51 (s, 1H), 2.86 (br s, 1H), 2.45 (s, 2H), 1.68~1.64 (m, 4H), 1.64 (s, 3H), 1.18 (s, 6H), 1.07 (s, 9H)

Synthesis Example 29: Synthesis of Compound 29

Compound 29 was synthesized according to Reaction Scheme 29 below:

<Reaction Scheme 29>

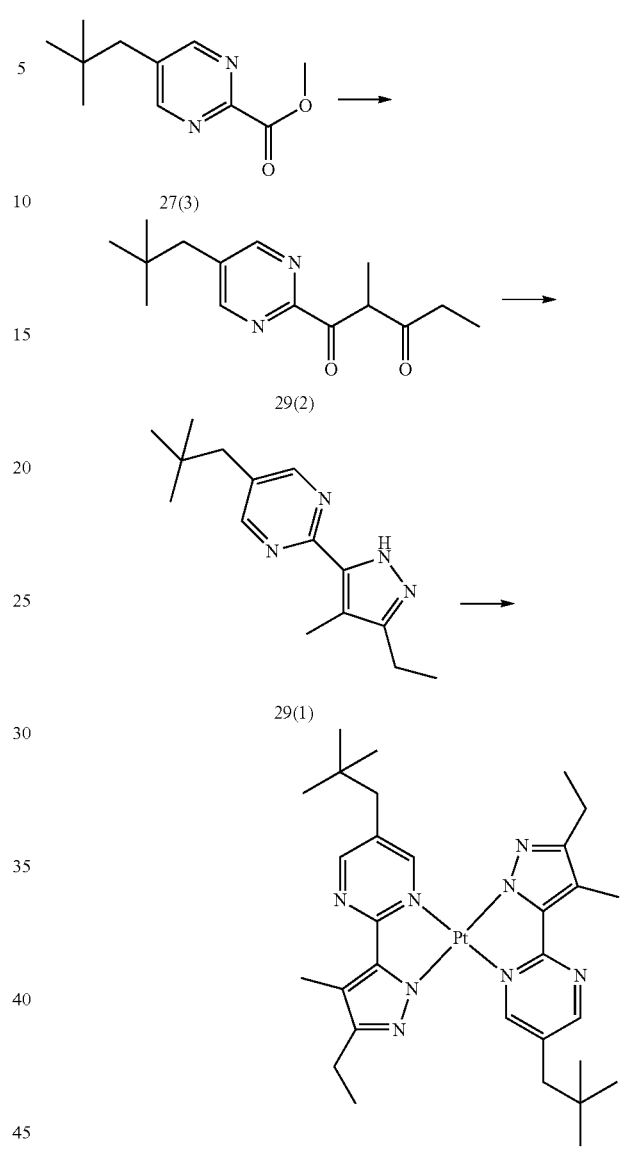

Compound 29

Synthesis of Intermediate 29(2)

Intermediate 29(2) was synthesized in the same manner as in the synthesis of Intermediate 10(2) of Synthesis Example 10, except that Intermediate 27(3), instead of Intermediate 5(3), was used (Yield: 46%). This compound was identified using LC-MS.

LC-MS m/z=263 (M+H)⁺

Synthesis of Intermediate 29(1)

Intermediate 29(1) was synthesized in the same manner as in the synthesis of Intermediate 5(1) of Synthesis Example 1, except that Intermediate 29(2), instead of Intermediate 5(2), was used (Yield: 75%). This compound was identified using LC-MS.

LC-MS m/z=259 (M+H)⁺

Synthesis of Compound 29

Compound 29 was synthesized in the same manner as in the synthesis of Compound 5 of Synthesis Example 1, except that Intermediate 28(1), instead of Intermediate 5(1), was used (Yield: 65%). This compound was identified using LC-MS and $^1$H NMR.

LC-MS m/z=710 (M+H)$^+$ $^1$H NMR (500 MHz, CDCl$_3$) δ=10.76 (s, 1H), 8.54 (s, 1H), 2.65 (q, 2H), 2.46 (s, 2H), 2.41 (s, 3H), 1.35 (t, 3H), 1.05 (s, 9H).

Synthesis Example 30: Synthesis of Compound 30

Compound 30 was synthesized according to Reaction Scheme 30 below:

<Reaction Scheme 30>

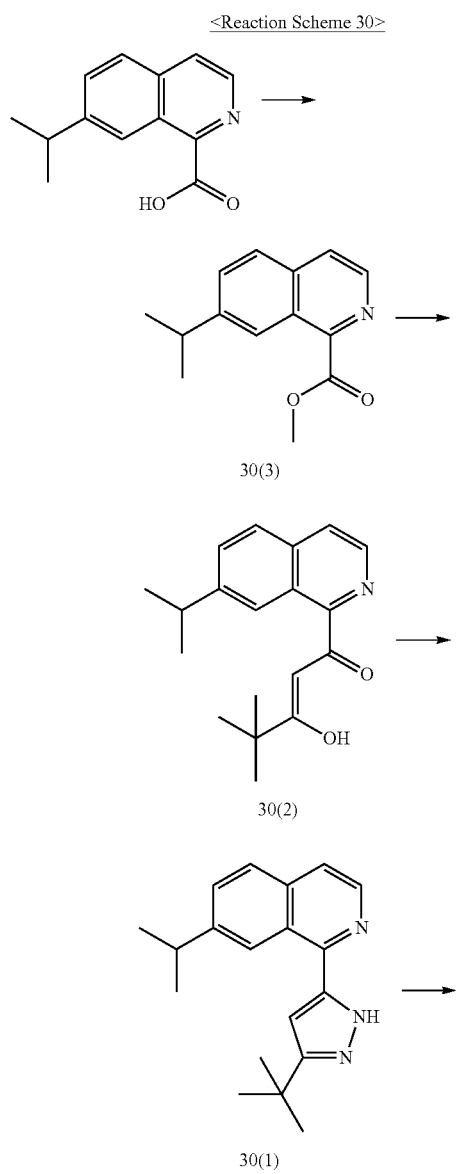

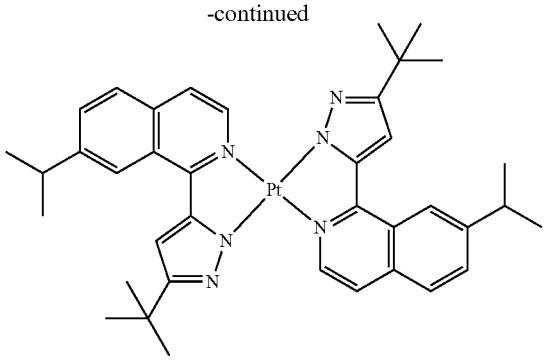

Compound 30

Synthesis of Intermediate 30(3)

Intermediate 30(3) was synthesized in the same manner as in the synthesis of Intermediate 5(3) of Synthesis Example 1, except that 7-isopropyl-isoquinoline-1-carboxylic acid, instead of 5-isobutyl-pyridine-2-carboxylic acid, was used (Yield: 95%). This compound was identified using LC-MS.

LC-MS m/z=230 (M+H)$^+$

Synthesis of Intermediate 30(2)

Intermediate 30(2) was synthesized in the same manner as in the synthesis of Intermediate 5(2) of Synthesis Example 1, except that Intermediate 30(3), instead of Intermediate 5(3), was used (Yield: 41%). This compound was identified using LC-MS.

LC-MS m/z=298 (M+H)$^+$

Synthesis of Intermediate 30(1)

Intermediate 30(1) was synthesized in the same manner as in the synthesis of Intermediate 5(1) of Synthesis Example 1, except that Intermediate 30(2), instead of Intermediate 5(2), was used (Yield: 63%). This compound was identified using LC-MS.

LC-MS m/z=294 (M+H)$^+$

Synthesis of Compound 30

Compound 30 was synthesized in the same manner as in the synthesis of Compound 5 of Synthesis Example 1, except that Intermediate 30(1), instead of Intermediate 5(1), was used (Yield: 46%). This compound was identified using LC-MS and $^1$H NMR.

LC-MS m/z=780 (M+H)$^+$ $^1$H NMR (500 MHz, CDCl$_3$) δ=8.62 (d, 1H), 7.72-7.43 (m, 4H), 6.74 (s, 1H), 3.16-3.14 (m, 1H), 1.33 (s, 9H), 1.27 (s, 6H).

Synthesis Example 31: Synthesis of Compound 31

Compound 31 was synthesized according to Reaction Scheme 31 below:

<Reaction Scheme 31>

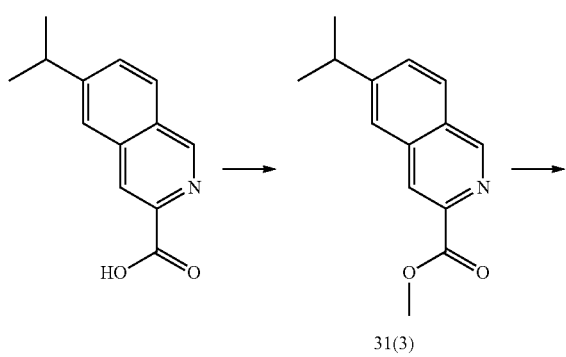

31(3)

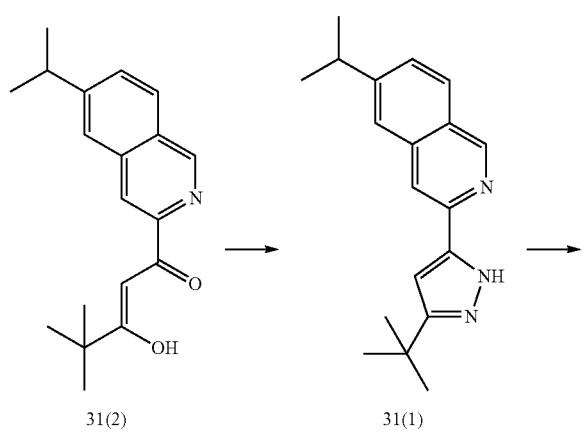

31(2)      31(1)

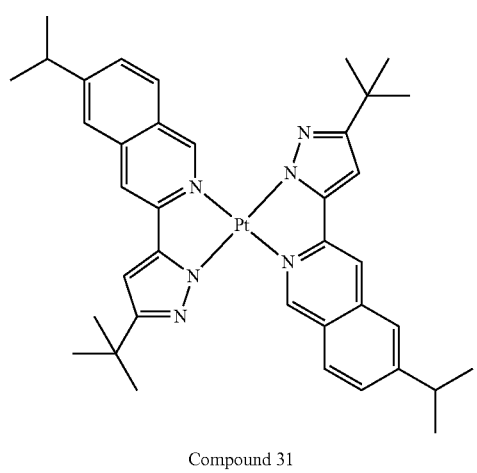

Compound 31

Synthesis of Intermediate 31(3)

Intermediate 31(3) was synthesized in the same manner as in the synthesis of Intermediate 5(3) of Synthesis Example 1, except that 6-isopropyl-isoquinoline-3-carboxylic acid, instead of 6-isobutyl-pyridine-2-carboxylic acid, was used (Yield: 96%). This compound was identified using LC-MS.

LC-MS m/z=230 (M+H)$^+$

Synthesis of Intermediate 31(2)

Intermediate 31(2) was synthesized in the same manner as in the synthesis of Intermediate 5(2) of Synthesis Example 1, except that Intermediate 31(3), instead of Intermediate 5(3), was used (Yield: 45%). This compound was identified using LC-MS.

LC-MS m/z=298 (M+H)$^+$

Synthesis of Intermediate 31(1)

Intermediate 31(1) was synthesized in the same manner as in the synthesis of Intermediate 5(1) of Synthesis Example 1, except that Intermediate 31(2), instead of Intermediate 5(2), was used (Yield: 55%). This compound was identified using LC-MS.

LC-MS m/z=294 (M+H)$^+$

Synthesis of Compound 31

Compound 31 was synthesized in the same manner as in the synthesis of Compound 5 of Synthesis Example 1, except that Intermediate 31(1), instead of Intermediate 5(1), was used (Yield: 54%). This compound was identified using LC-MS and $^1$H NMR.

LC-MS m/z=780 (M+H)$^+$ $^1$H NMR (500 MHz, CDCl$_3$) δ=9.15 (s, 1H), 7.86-7.46 (m, 4H), 6.77 (s, 1H), 3.12-3.10 (m, 1H), 1.34 (s, 9H), 1.29 (s, 6H).

Synthesis Example 32: Synthesis of Compound 32

Compound 32 was synthesized according to Reaction Scheme 32 below:

<Reaction Scheme 32>

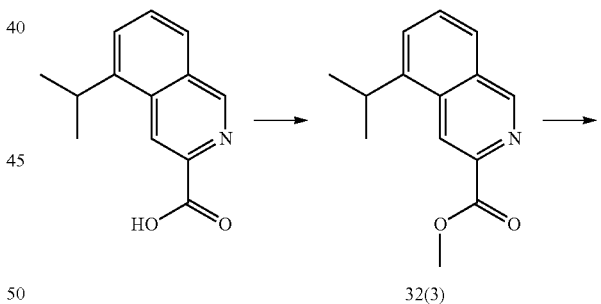

32(3)

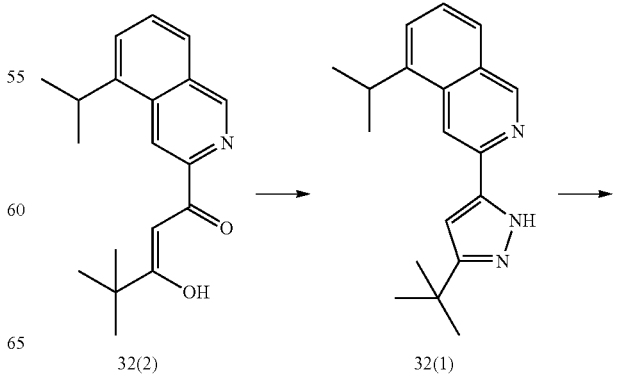

32(2)      32(1)

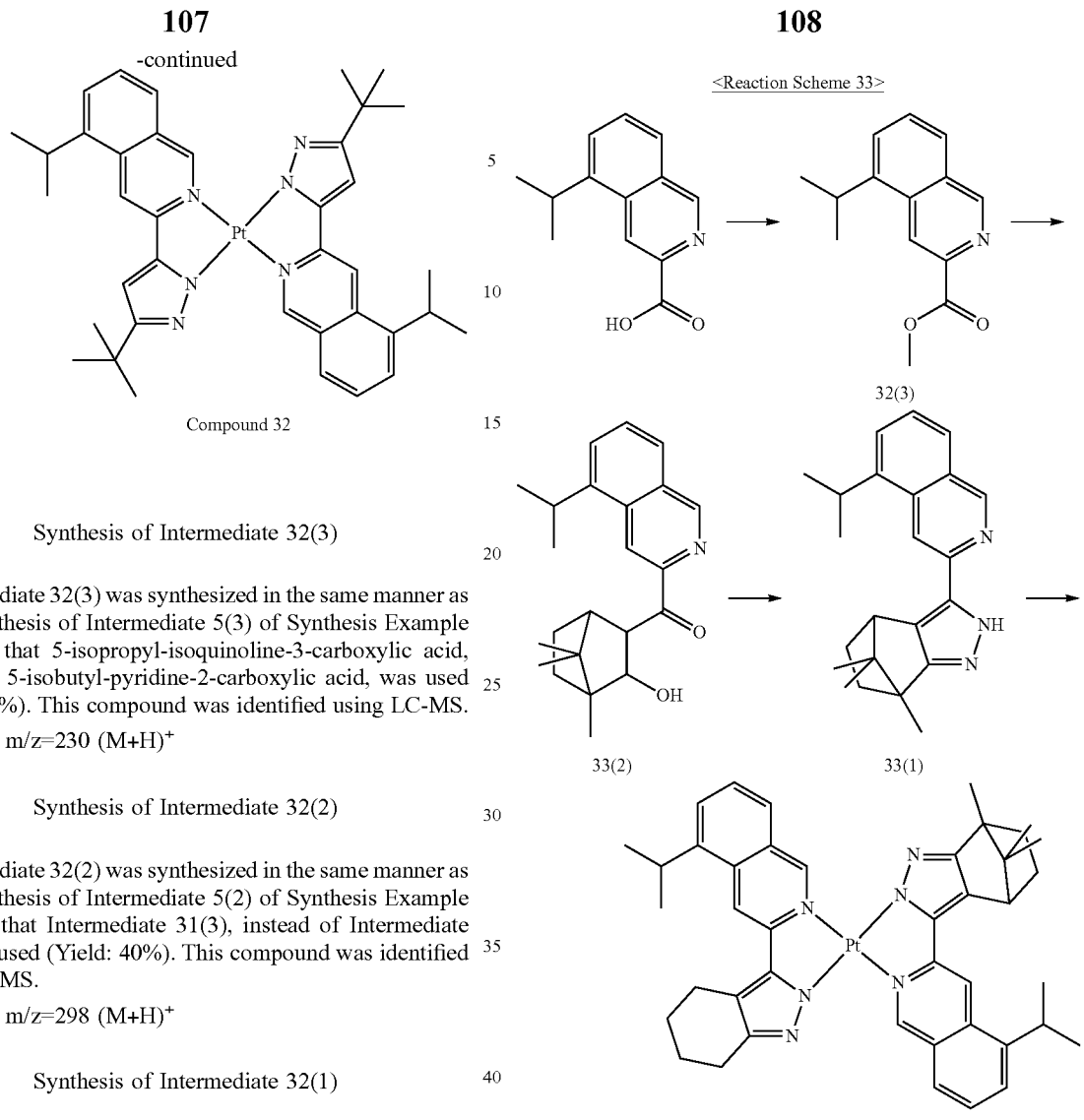

Compound 32

Synthesis of Intermediate 32(3)

Intermediate 32(3) was synthesized in the same manner as in the synthesis of Intermediate 5(3) of Synthesis Example 1, except that 5-isopropyl-isoquinoline-3-carboxylic acid, instead of 5-isobutyl-pyridine-2-carboxylic acid, was used (Yield: 95%). This compound was identified using LC-MS.

LC-MS m/z=230 (M+H)$^+$

Synthesis of Intermediate 32(2)

Intermediate 32(2) was synthesized in the same manner as in the synthesis of Intermediate 5(2) of Synthesis Example 1, except that Intermediate 31(3), instead of Intermediate 5(3), was used (Yield: 40%). This compound was identified using LC-MS.

LC-MS m/z=298 (M+H)$^+$

Synthesis of Intermediate 32(1)

Intermediate 32(1) was synthesized in the same manner as in the synthesis of Intermediate 5(1) of Synthesis Example 1, except that Intermediate 31(2), instead of Intermediate 5(2), was used (Yield: 60%). This compound was identified using LC-MS.

LC-MS m/z=294 (M+H)$^+$

Synthesis of Compound 32

Compound 32 was synthesized in the same manner as in the synthesis of Compound 5 of Synthesis Example 1, except that Intermediate 31(1), instead of Intermediate 5(1), was used (Yield: 67%). This compound was identified using LC-MS and $^1$H NMR.

LC-MS m/z=780 (M+H)$^+$ $^1$H NMR (500 MHz, CDCl$_3$) δ=9.21 (s, 1H), 7.74-7.41 (m, 4H), 6.80 (s, 1H), 3.14-3.12 (m, 1H), 1.33 (s, 9H), 1.26 (s, 6H).

Synthesis Example 33: Synthesis of Compound 33

Compound 33 was synthesized according to Reaction Scheme 33 below:

<Reaction Scheme 33>

Compound 33

Synthesis of Intermediate 33(2)

Intermediate 32(2) was synthesized in the same manner as in the synthesis of Intermediate 2(2) of Synthesis Example 9, except that Intermediate 32(3), instead of Intermediate 5(3), was used (Yield: 65%). This compound was identified using LC-MS.

LC-MS m/z=350 (M+H)$^+$

Synthesis of Intermediate 33(1)

Intermediate 33(1) was synthesized in the same manner as in the synthesis of Intermediate 5(1) of Synthesis Example 1, except that Intermediate 33(2), instead of Intermediate 5(2), was used (Yield: 62%). This compound was identified using LC-MS.

LC-MS m/z=346 (M+H)$^+$

Synthesis of Compound 33

Compound 33 was synthesized in the same manner as in the synthesis of Compound 5 of Synthesis Example 1, except that Intermediate 33(1), instead of Intermediate 5(1), was used (Yield: 60%). This compound was identified using LC-MS and $^1$H NMR.

LC-MS m/z=830 (M+H)$^+$ $^1$H NMR (500 MHz, CDCl$_3$) δ=9.20 (s, 1H), 7.75-7.40 (m, 4H), 3.14-3.07 (m, 1H), 2.26-2.24 (m, 1H), 1.65~1.62 (m, 4H), 1.63 (s, 3H), 1.26 (d, 6H), 1.23 (s, 6H).

Synthesis Example 34: Synthesis of Compound 34

Compound 34 was synthesized according to Reaction Scheme 34 below:

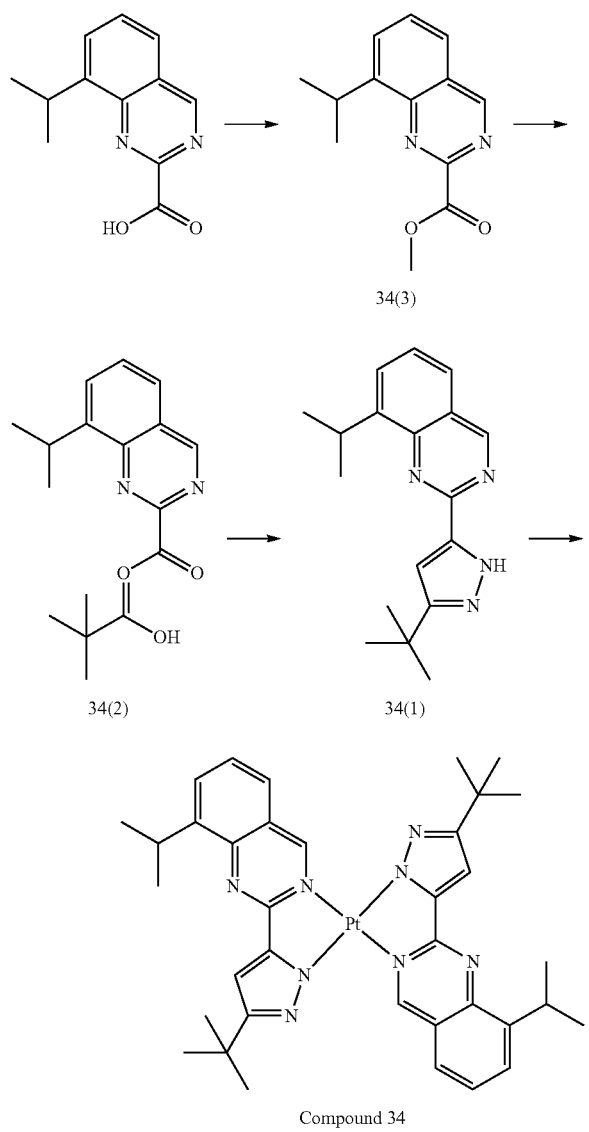

Synthesis of Intermediate 34(3)

Intermediate 34(3) was synthesized in the same manner as in the synthesis of Intermediate 5(3) of Synthesis Example 1, except that 8-isopropyl-quinazoline-2-carboxylic acid, instead of 5-isobutyl-pyridine-2-carboxylic acid, was used (Yield: 95%). This compound was identified using LC-MS.

LC-MS m/z=231 (M+H)$^+$

Synthesis of Intermediate 34(2)

Intermediate 34(3) was synthesized in the same manner as in the synthesis of Intermediate 5(2) of Synthesis Example 1, except that Intermediate 34(3), instead of Intermediate 5(3), was used (Yield: 45%). This compound was identified using LC-MS.

LC-MS m/z=299 (M+H)$^+$

Synthesis of Intermediate 34(1)

Intermediate 34(1) was synthesized in the same manner as in the synthesis of Intermediate 5(1) of Synthesis Example 1, except that Intermediate 34(2), instead of Intermediate 5(2), was used (Yield: 55%). This compound was identified using LC-MS.

LC-MS m/z=295 (M+H)$^+$

Synthesis of Compound 34

Compound 34 was synthesized in the same manner as in the synthesis of Compound 5 of Synthesis Example 1, except that Intermediate 34(1), instead of Intermediate 5(1), was used (Yield: 57%). This compound was identified using LC-MS and $^1$H NMR.

LC-MS m/z=782 (M+H)$^+$ $^1$H NMR (500 MHz, CDCl$_3$) δ=9.41 (s, 1H), 7.77-7.53 (m, 3H), 6.78 (s, 1H), 3.12-3.10 (m, 1H), 1.34 (s, 9H), 1.28 (s, 6H).

Synthesis Example 35: Synthesis of Compound 35

Compound 35 was synthesized according to Reaction Scheme 35 below:

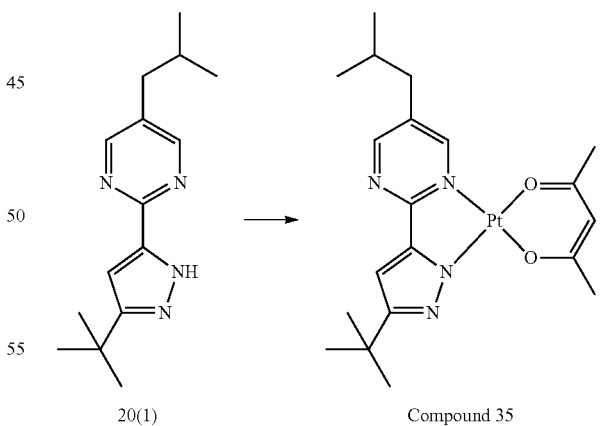

After 1.2 g (4.7 mmol) of Intermediate 20(1) and 2.0 g (4.7 mmol) of K$_2$PtCl$_4$ were dissolved in a mixed solvent of 30 mL of ethanol and 10 mL of distilled water, 5 mL of a 4N HCl solution was added to the solution, and the resulting solution was then heated under reflux. After 18 hours of reflux, the reaction product was cooled down to room temperature, and filtered and dried. After the resulting product solution was mixed with 10 mL of tetrahydrofuran, the mixture was dropwise added to a reaction vessel containing 30 mL of anhydrous tetrahydrofuran and 4.7 mmol of NaH at about 0° C. After 5 minutes, Na(acac) was added to the mixture, and the resulting reaction mixture was heated under reflux for about 18 hours. The resulting solid product was isolated by filtration, affording 0.46 g (0.84 mmol) of Compound 35 (Yield: 18%). This compound was identified using LC-MS and $^1$H NMR.

LC-MS m/z=552 (M+H)$^+$ $^1$H NMR (500 MHz, CDCl$_3$) δ=10.36 (s, 1H), 8.25 (s, 1H), 6.82 (s, 1H), 5.31 (br s, 1H), 2.41 (d, 2H), 2.24-2.22 (m, 1H), 2.10 (s, 3H), 1.27 (s, 9H), 1.18 (s, 3H), 1.00 (s, 6H)

Example 1

To manufacture an anode, a glass substrate with deposited ITO/Ag/ITO layers (70/1000/70 Å) was cut to a size of 50 mm×50 mm×0.5 mm and then ultrasonicated in isopropyl alcohol and pure water each for five minutes, and then cleaned by irradiation of ultraviolet rays for 30 minutes and exposure to ozone. The resulting glass substrate was loaded into a vacuum deposition diode.

2-TNATA was deposited to form an HIL having a thickness of 600 Å on the anode, and then 4.4'-bis[N-(1-naphthyl)-N-phenylamino]biphenyl (NPB) was deposited on the HIL to form a HTL having a thickness of about 1000 Å.

CBP (host) and Compound 5 (dopant) were co-deposited in a weight ratio of about 91:9 on the HTL to form an EML having a thickness of about 250 Å, and this was followed by depositing BCP on the EML to form a HBL having a thickness of about 50 Å. After deposition of Alq$_3$ on the hole blocking layer to form an electron transport layer having a thickness of about 350 Å, LiF was deposited on the electron transport layer to form an electron injecting layer having a thickness of about 10 Å, followed by depositing Mg and Al in a weight ratio of about 90:10 on the electron injection layer to form a cathode having a thickness of about 120 Å, thereby completing the manufacture of the organic light-emitting diode (emitting green light).

Example 2

An organic light-emitting diode was manufactured in the same manner as in Example 1, except that Compound 8, instead of Compound 5, was used to form the EML.

Example 3

An organic light-emitting diode was manufactured in the same manner as in Example 1, except that Compound 26, instead of Compound 5, was used to form the EML.

Example 4

An organic light-emitting diode was manufactured in the same manner as in Example 1, except that Compound 27, instead of Compound 5, was used to form the EML.

Example 5

An organic light-emitting diode was manufactured in the same manner as in Example 1, except that Compound 32, instead of Compound 5, was used to form the EML.

Example 6

An organic light-emitting diode (emitting red light) was manufactured in the same manner as in Example 1, except that the thickness of the HTL was varied to about 1350 Å, and CBP (host) and Compound 7 (dopant) were co-deposited in a weight ratio of about 94:6 on the HTL to form an EML having a thickness of about 400 Å.

Example 7

An organic light-emitting diode was manufactured in the same manner as in Example 6, except that Compound 22, instead of Compound 7, was used to form the EML.

Example 8

An organic light-emitting diode was manufactured in the same manner as in Example 6, except that Compound 30, instead of Compound 7, was used to form the EML.

Comparative Example 1

An organic light-emitting diode was manufactured in the same manner as in Example 1, except that Ir(ppy)$_3$, instead of Compound 5, was used to form the EML.

Comparative Example 2

An organic light-emitting diode was manufactured in the same manner as in Example 6, except that Compound A, instead of Compound 7, was used to form the EML.

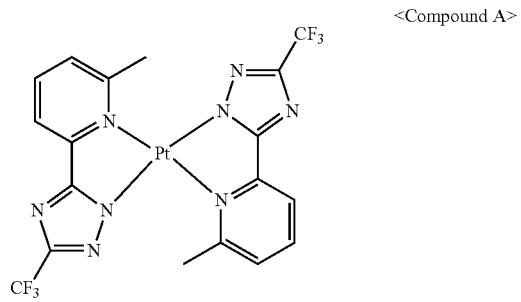

<Compound A>

Comparative Example 3

An organic light-emitting diode was manufactured in the same manner as in Example 1, except that Compound B, instead of Compound 5, was used to form the EML.

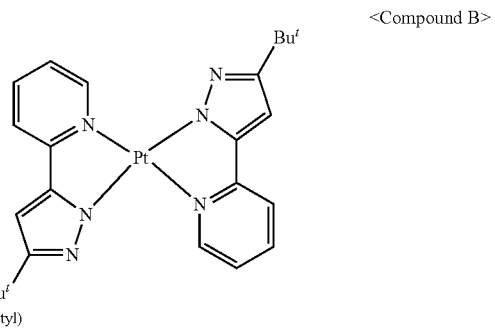

<Compound B>

(Bu$^t$ = tert-butyl)

Comparative Example 4

An organic light-emitting diode was manufactured in the same manner as in Example 6, except that PtOEP, instead of Compound 7, was used to form the EML.

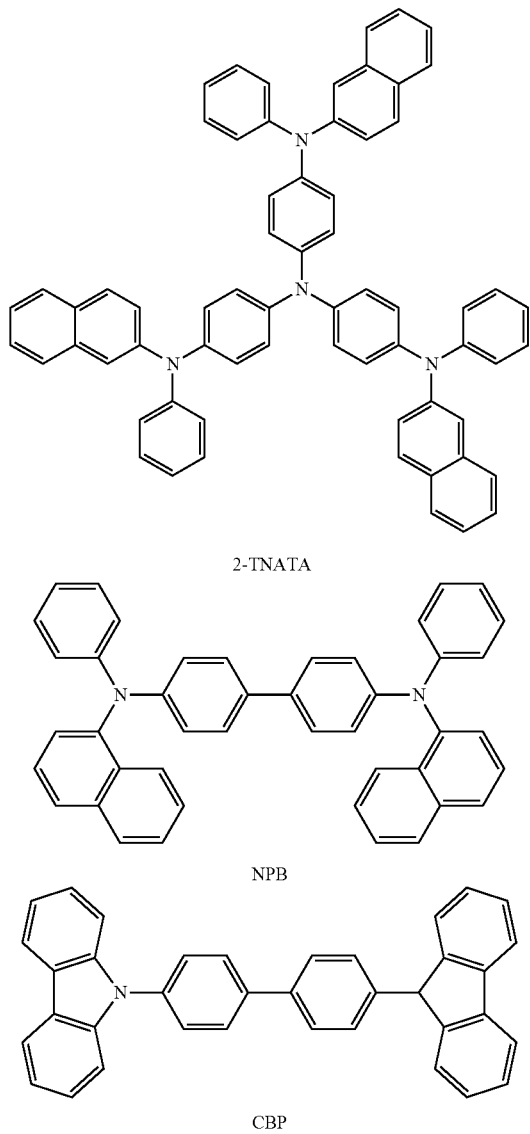

2-TNATA

NPB

CBP

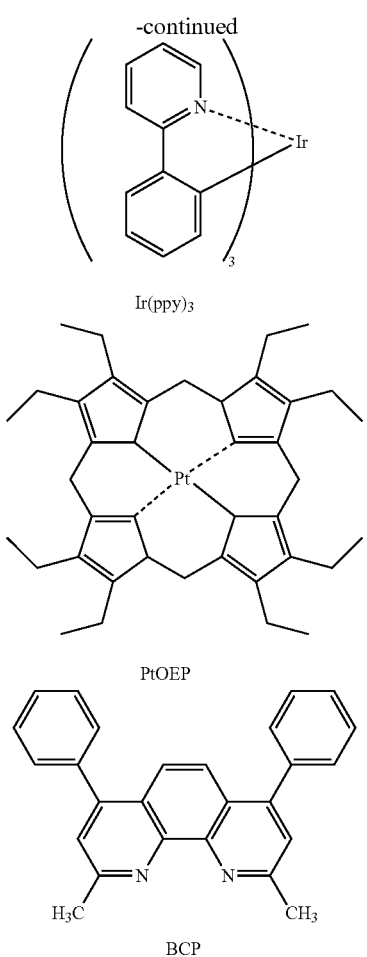

Ir(ppy)₃

PtOEP

BCP

Evaluation Example 1

Driving voltages, current densities, luminance, efficiencies, color purities, and lifetime characteristics of the organic light-emitting diodes of Examples 1 to 3 and Comparative Examples 1 to 4 were measured using a PR650 (Spectroscan) Source Measurement Unit. (available from Photo Research, Inc.). In Table 1, $LT_{97}$ lifetime indicates the time taken until an initial luminance (assumed as 100%) measured at a current density of about 10 mA/cm² is reduced to 97%. The results are shown in Table 1 below.

TABLE 1

| Example | Host | Dopant | Driving voltage (V) | Current density (mA/cm²) | Luminance (cd/m²) | Efficiency (cd/A) | Emission color | Color coordinates | $LT_{97}$ (HR) |
|---|---|---|---|---|---|---|---|---|---|
| Example 1 | CBP | Compound 5 | 5.4 | 10 | 6,436 | 64.4 | Green | 0.28, 0.65 | 90 |
| Example 2 | CBP | Compound 8 | 5.3 | 10 | 6,710 | 67.1 | Green | 0.26, 0.70 | 88 |
| Example 3 | CBP | Compound 26 | 5.3 | 10 | 6,972 | 69.7 | Green | 0.27, 0.72 | 98 |
| Example 4 | CBP | Compound 27 | 5.3 | 10 | 6,782 | 67.8 | Green | 0.26, 0.71 | 95 |
| Example 5 | CBP | Compound 32 | 5.4 | 10 | 6,620 | 66.2 | Green | 0.25, 0.69 | 91 |
| Example 6 | CBP | Compound 7 | 5.9 | 10 | 3,150 | 31.5 | Red | 0.64, 033 | 102 |
| Example 7 | CBP | Compound 22 | 5.8 | 10 | 3,376 | 33.8 | Red | 0.65, 0.35 | 100 |
| Example 8 | CBP | Compound 30 | 5.9 | 10 | 3,215 | 32.2 | Red | 0.65, 0.33 | 103 |
| Comparative Example 1 | CBP | Ir(ppy)₃ | 6.8 | 10 | 4,766 | 47.7 | Green | 0.25, 0.70 | 61 |
| Comparative Example 2 | CBP | Compound A | 6.1 | 10 | 1,651 | 16.5 | Red | 0.61, 0.36 | 23 |

TABLE 1-continued

| Example | Host | Dopant | Driving voltage (V) | Current density (mA/cm$^2$) | Luminance (cd/m$^2$) | Efficiency (cd/A) | Emission color | Color coordinates | LT$_{97}$ (HR) |
|---|---|---|---|---|---|---|---|---|---|
| Comparative Example 3 | CBP | Compound B | 5.9 | 10 | 3,281 | 32.8 | Green | 0.22, 0.61 | 41 |
| Comparative Example 4 | CBP | PtOEP | 7.3 | 10 | 2,212 | 22.1 | Red | 0.67, 0.32 | 75 |

Referring to Table 1, the organic light-emitting diodes of Examples 1 to 5 were found to have lower driving voltages, higher luminance, higher efficiencies and longer lifetimes than the organic light-emitting diodes of Comparative Examples 1 and 3. The organic light-emitting diodes of Examples 6 to 9 were found to have lower driving voltages, higher luminance, higher efficiencies, and longer lifetimes, than the organic light-emitting diodes of Comparative Examples 2 and 4.

As described above, an organic light-emitting diode including the organometallic compound of Formula 1 above may have a low driving voltage, a high efficiency, a high color purity, and a long lifetime.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. An organometallic compound represented by Formula 1(1) below:

<Formula 1(1)>

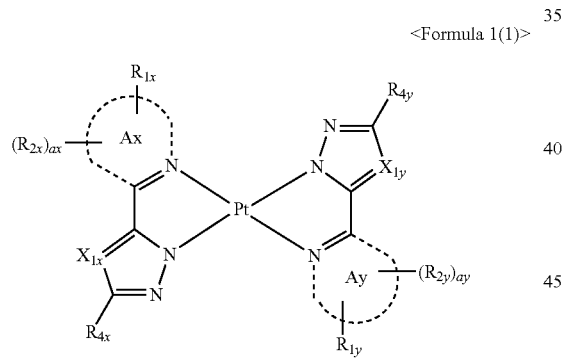

wherein, an Ax ring and an Ay ring in Formula 1(1) each being independently one of a 6-membered ring including at least one N, a 6-membered ring condensed with at least one 5-membered ring and including at least one N, and a 6-membered ring condensed with at least one 6-membered ring and including at least one N;

$R_{1x}$ and $R_{1y}$ in Formula 1(1) each being independently a substituted or unsubstituted linear or branched $C_2$-$C_{60}$ alkyl group;

$X_{1x}$ in Formula 1(1) being one of N and C($R_{3x}$), and $X_{1y}$ in Formula 1(1) being one of N and C($R_{3y}$);

$R_{2x}$ to $R_{4x}$ and $R_{2y}$ to $R_{4y}$ in Formula 1(1) each being independently selected from among a hydrogen atom, a deuterium atom, a halogen atom, a hydroxy group, a cyano group, a nitro group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —N($Q_1$)($Q_2$), —Si($Q_3$)($Q_4$)($Q_5$), and —C(=O)($Q_6$) (where $Q_1$ to $Q_6$ are each independently one of a hydrogen atom, a substituted or unsubstituted $C_1$-$C_{60}$ alkyl group, a substituted or unsubstituted $C_6$-$C_{60}$ aryl group, or a substituted or unsubstituted $C_2$-$C_{60}$ heteroaryl group), $R_{3x}$ and $R_{4x}$ being optionally linked to each other to form one of a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group and a substituted or unsubstituted $C_2$-$C_{20}$ heteroaromatic group and $R_{3y}$ and $R_{4y}$ being optionally linked to each other to form one of a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group and a substituted or unsubstituted $C_2$-$C_{20}$ heteroaromatic group; and $a_x$ and $a_y$ in Formula 1(1) each being independently an integer from 1 to 10.

2. The organometallic compound of claim 1, the Ax ring and the Ay ring being each independently selected from among pyridine, pyrazine, pyrimidine, pyridazine, purine, isoquinoline, quinoline, phthalazine, 1,8-naphthyridine, quinoxaline, quinazoline, cinnoline, phenanthridine, 1,7-phenanthroline and pyrrolopyrimidine.

3. The organometallic compound of claim 1, the Ax ring and the Ay ring being each independently selected from pyridine, pyrimidine, isoquinoline and quinazoline.

4. The organometallic compound of claim 1, $R_{1x}$ and $R_{1y}$ being each independently selected from among:

an ethyl group, a n-propyl group, an i-propyl group, a n-butyl group, an i-butyl group, a t-butyl group, a pentyl group, a hexyl group, a heptyl group, an octyl group, a nonyl group, and a decyl group; and an ethyl group, a n-propyl group, an i-propyl group, a n-butyl group, an i-butyl group, a t-butyl group, a pentyl group, a hexyl group, a heptyl group, an octyl group, a nonyl group, and a decyl group, each substituted with at least one of a deuterium atom, —F, a hydroxy group, a cyano group, a nitro group and an amino group.

5. The organometallic compound of claim 1, $X_{1x}$ being $C(R_{3x})$, and $X_{1y}$ being $C(R_{3y})$; and $R_{2x}$ to $R_{4x}$ and $R_{2y}$ to $R_{4y}$ being each independently one selected from among:

a hydrogen atom, a deuterium atom, a halogen atom, a hydroxy group, a cyano group, a nitro group, an amidino group, a hydrazine, a hydrazone, a carboxyl group or a salt thereof, a sulfonic acid group or a salt thereof, a phosphoric acid group or a salt thereof;

a methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group; and a methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, each substituted with at least one of a deuterium atom, —F, a hydroxy group, a cyano group, a nitro group, and an amino group, $R_{3x}$ and $R_{4x}$ optionally linked to each other to form one of a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group and a substituted or unsubstituted $C_2$-$C_{20}$ heteroaromatic group, and $R_{3y}$ and $R_{4y}$ being optionally linked to each other to form one of a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group and a substituted or unsubstituted $C_2$-$C_{20}$ heteroaromatic group.

6. The organometallic compound of claim 1, the organometallic compound being a compound represented by one of Formulae 1A to 1R below:

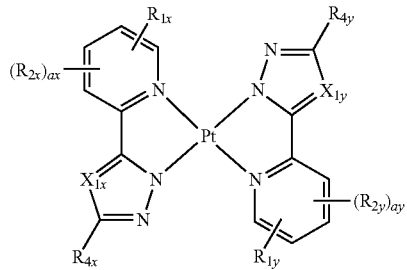

-continued
<Formula 1G>
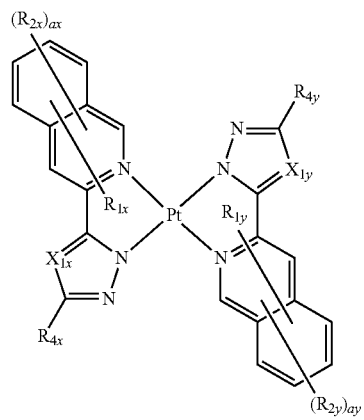
<Formula 1H>
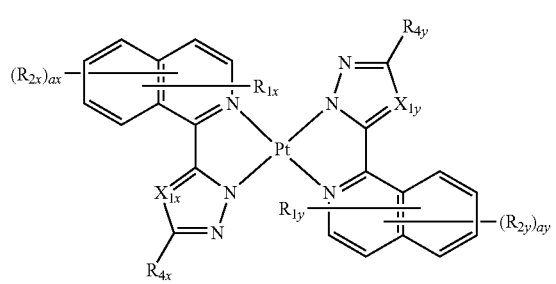
<Formula 1I>
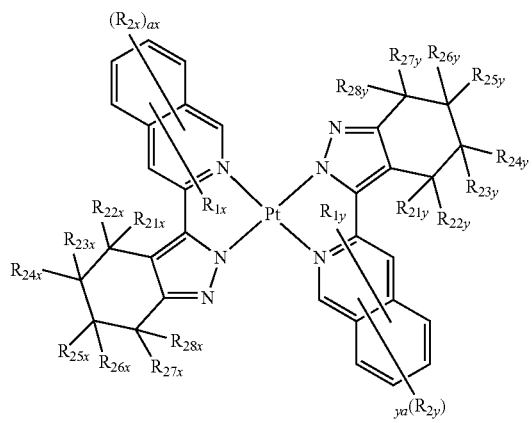
<Formula 1J>
<Formula 1K>
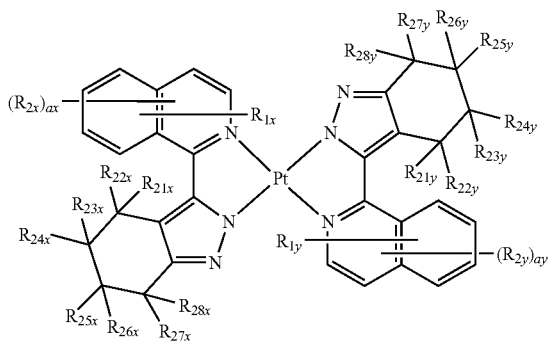
<Formula 1L>
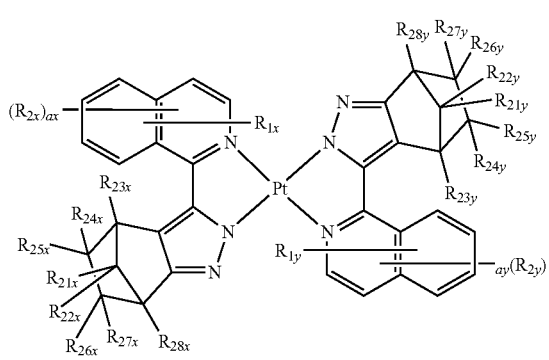
<Formula 1M>
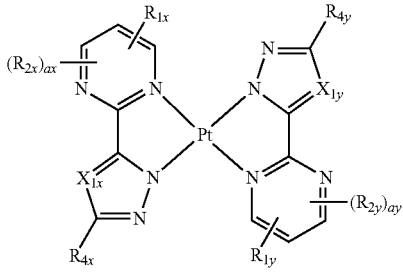
<Formula 1N>
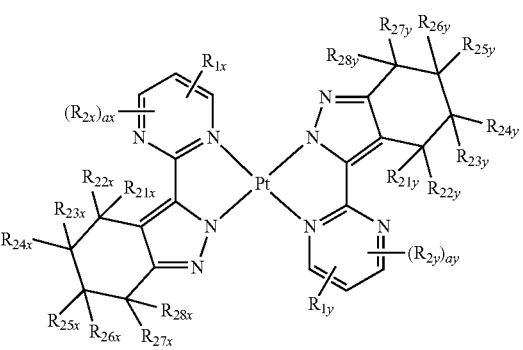

-continued

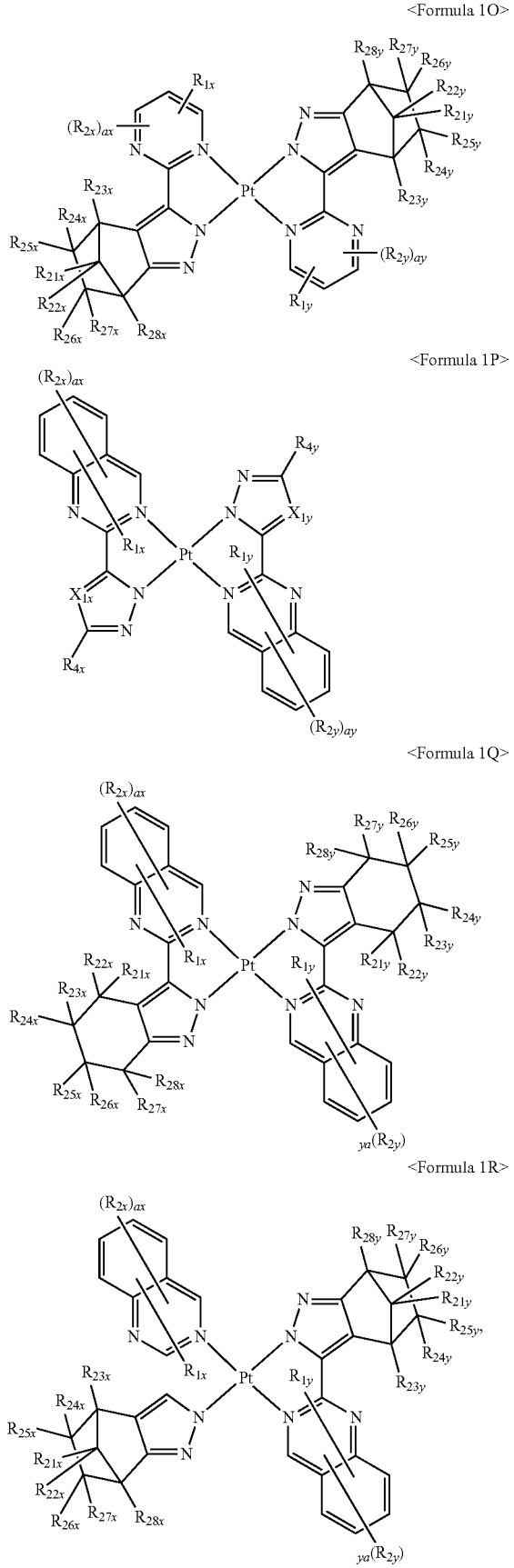

<Formula 1O>

<Formula 1P>

<Formula 1Q>

<Formula 1R>

$X_{1x}$ in Formulae 1A, 1B, 1G, 1H, 1M, and 1P being one of N and $C(R_{3x})$, and $X_{1y}$ in Formulae 1A, 1B, 1G, 1H, 1M, and 1P being one of N and $C(R_{3y})$;

$R_{1x}$ and $R_{1y}$ in Formulae 1A to 1R each being independently one selected from among:

an ethyl group, a n-propyl group, an i-propyl group, a n-butyl group, an i-butyl group, a t-butyl group, a pentyl group, a hexyl group, a heptyl group, an octyl group, a nonyl group, and a decyl group; and an ethyl group, a n-propyl group, an i-propyl group, a n-butyl group, an i-butyl group, a t-butyl group, a pentyl group, a hexyl group, a heptyl group, an octyl group, a nonyl group, and a decyl group, each substituted with at least one of a deuterium atom, —F, a hydroxy group, a cyano group, a nitro group, and an amino group;

$R_{2x}$ to $R_{4x}$, $R_{21x}$ to $R_{28x}$, $R_{2y}$ to $R_{4y}$, and $R_{21y}$ to $R_{28y}$ in Formulae 1A to 1R each being independently one selected from among:

a hydrogen atom, a deuterium atom, a halogen atom, a hydroxy group, a cyano group, a nitro group, an amidino group, a hydrazine, a hydrazone, a carboxyl group or a salt thereof, a sulfonic acid group or a salt thereof, a phosphoric acid group or a salt thereof;

a methyl group, an ethyl group, n-propyl group, i-propyl group, n-butyl group, i-butyl group, t-butyl group, a pentyl group, a hexyl group, a heptyl group, an octyl group, a nonyl group, a decyl group, a methoxy group, an ethoxy group, a propoxy group, a butoxy group, and a pentoxy group; and a methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, each substituted with at least one of a deuterium atom, —F, a hydroxy group, a cyano group, a nitro group, and an amino group; and $a_x$ and $a_y$ in Formulae 1A to 1R each being independently an integer from 1 to 3.

7. The organometallic compound of claim 1, the organometallic compound being a compound represented by one of Formulae 1A(1), 1A(2), 1A(3), 1B(1), 1C(1), 1D(1), 1D(2), 1E(1), 1F(1), 1G(1), 1H(1), 1J(1), 1M(1), 1M(2), 1N(1), 1N(2), 1O(1), and 1P(1) below:

<Formula 1A(1)>

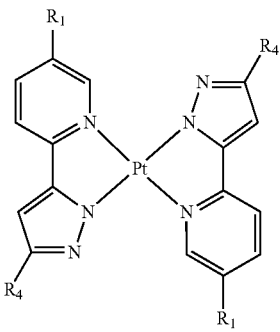

<Formula 1A(2)>
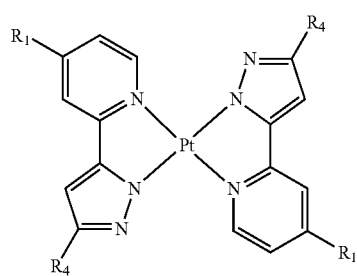
<Formula 1A(3)>
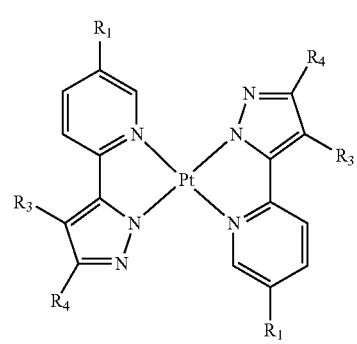
<Formula 1B(1)>
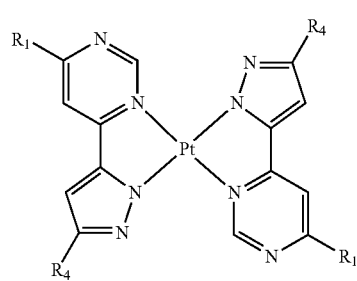
<Formula 1C(1)>
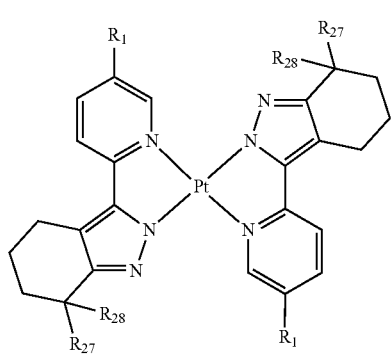
<Formula 1D(1)>
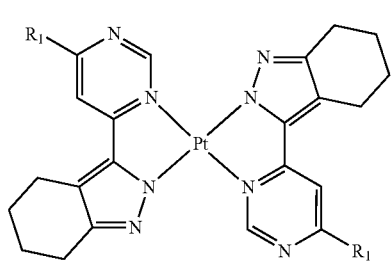
<Formula 1D(2)>
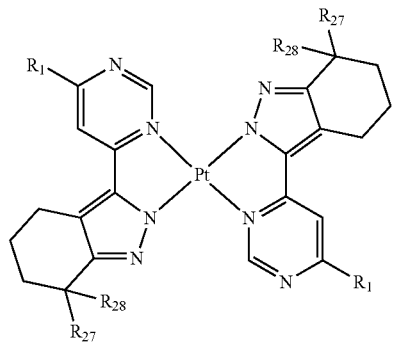
<Formula 1E(1)>
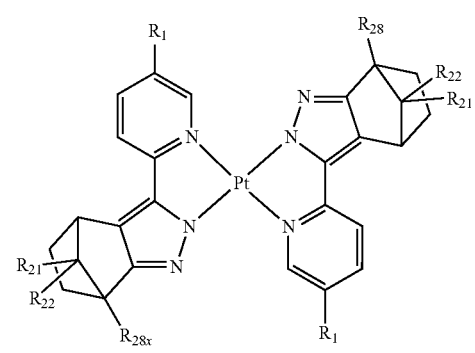
<Formula 1F(1)>
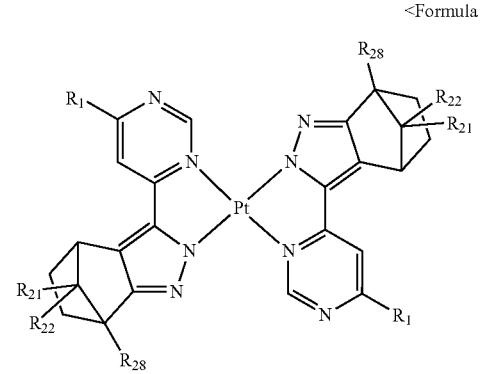
<Formula 1G(1)>
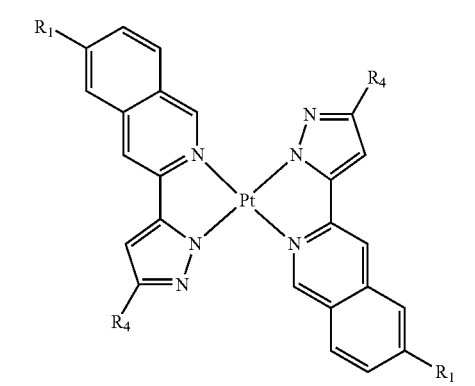

<Formula 1H(1)>
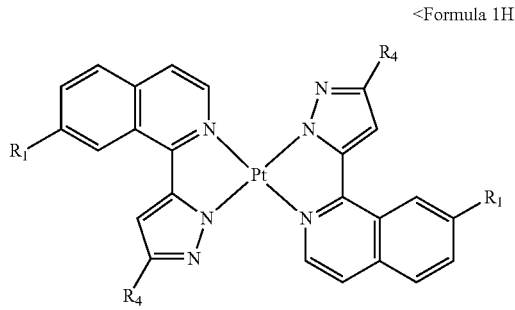
<Formula 1J(1)>
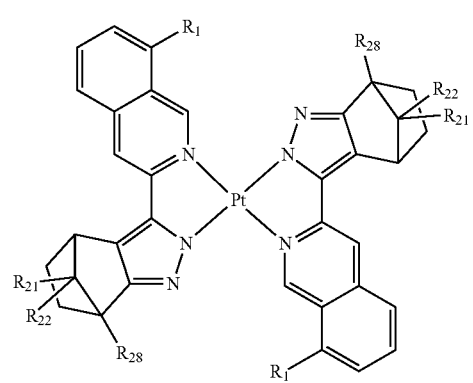
<Formula 1M(1)>
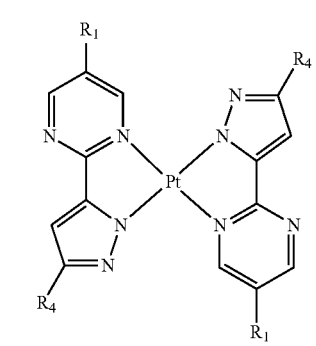
<Formula 1M(2)>
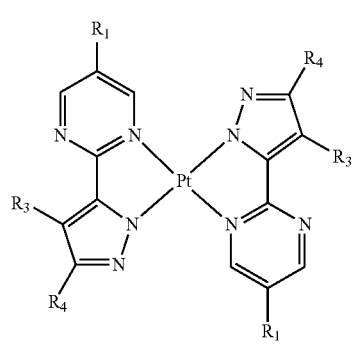
<Formula 1N(1)>
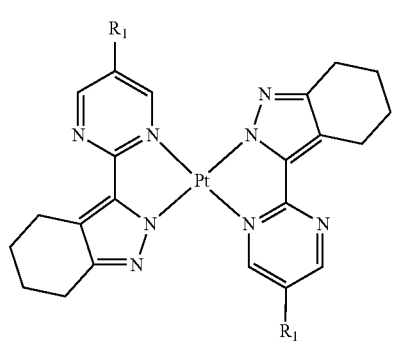
<Formula 1N(2)>
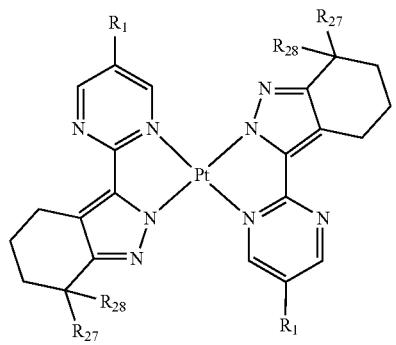
<Formula 1O(1)>
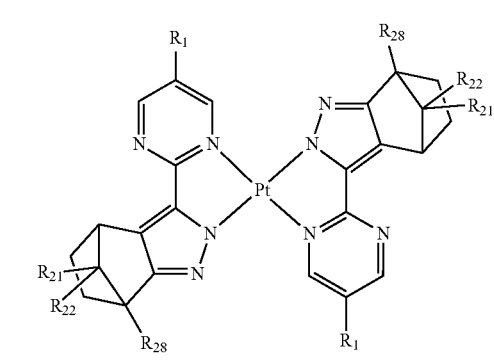
<Formula 1P(1)>
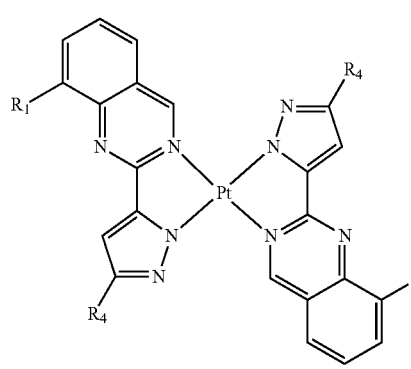
$R_1$ in Formulae 1A(1), 1A(2), 1A(3), 1B(1), 1C(1), 1D(1), 1D(2), 1E(1), 1F(1), 1G(1), 1H(1), 1J(1), 1M(1), 1M(2), 1N(1), 1N(2), 1O(1), and 1P(1) being one selected from among:
an ethyl group, a n-propyl group, an i-propyl group, a n-butyl group, an i-butyl group, a t-butyl group, a pentyl group, a hexyl group, a heptyl group, an octyl group, a nonyl group, and a decyl group; and an ethyl group, a n-propyl group, an i-propyl group, a n-butyl group, an i-butyl group, a t-butyl group, a pentyl group, a hexyl group, a heptyl group, an octyl group, a nonyl group, and a decyl group, each substituted with at least one of a deuterium atom, —F, a hydroxy group, a cyano group, a nitro group, and an amino group, and $R_3$, $R_4$, $R_{21}$, $R_{22}$, $R_{27}$, and $R_{28}$ in Formulae 1A(1), 1A(2), 1A(3), 1B(1), 1C(1), 1D(1), 1D(2), 1E(1), 1F(1), 1G(1), 1H(1), 1J(1), 1M(1), 1M(2), 1N(1), 1N(2), 1O(1), and 1P(1) each being independently one selected from among:

a hydrogen atom, a deuterium atom, a halogen atom, a hydroxy group, a cyano group, a nitro group, an amidino group, a hydrazine, a hydrazone, a carboxyl group or a salt thereof, a sulfonic acid group or a salt thereof, a phosphoric acid group or a salt thereof;

a methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group; and a methyl group, an ethyl group, a n-propyl group, an i-propyl group, a n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, each substituted with at least one of a deuterium atom, —F, a hydroxy group, a cyano group, and a nitro group.

8. The organometallic compound of claim 1, the organometallic compound being one of Compounds 1 to 34 below:

1

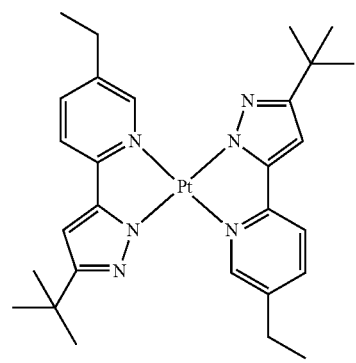

2

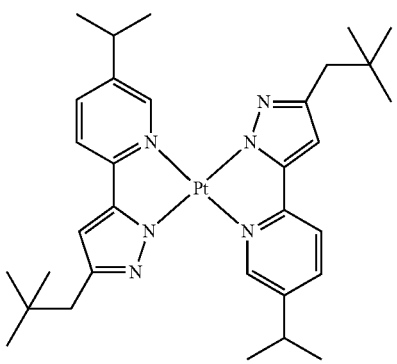

-continued

3

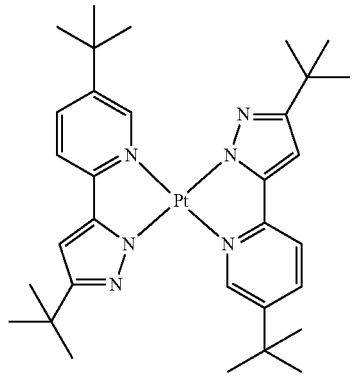

4

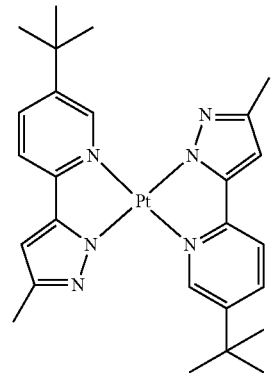

5

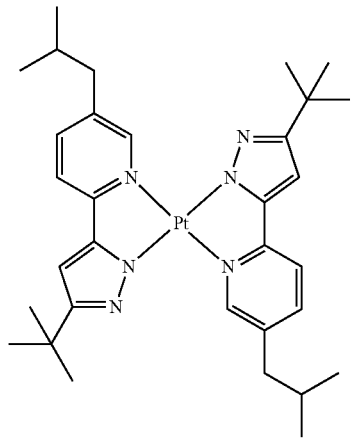

6

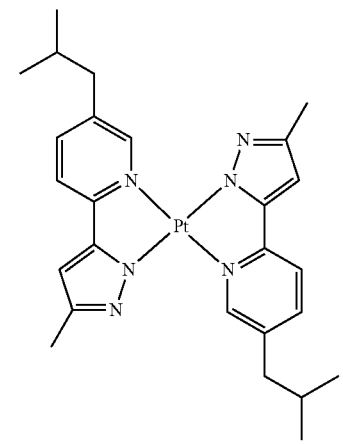

129
-continued
7
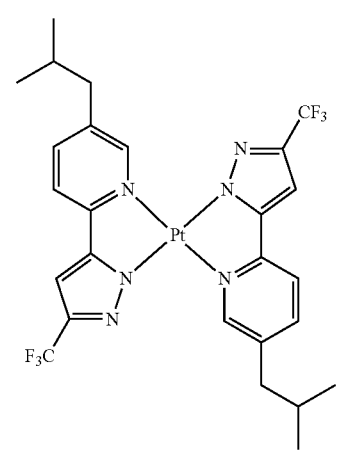
8
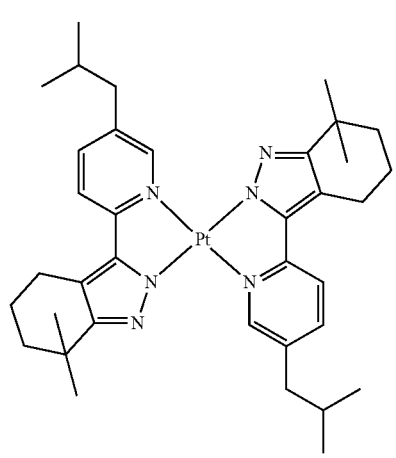
9
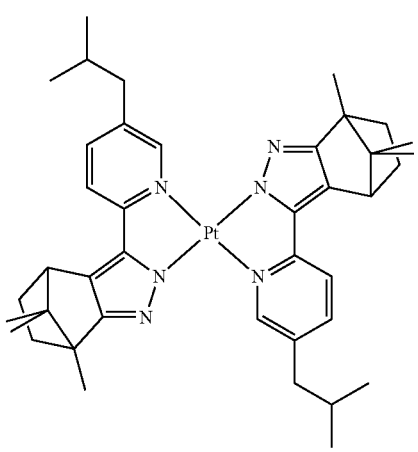
130
-continued
10
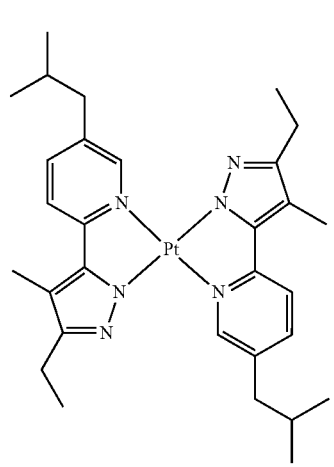
11
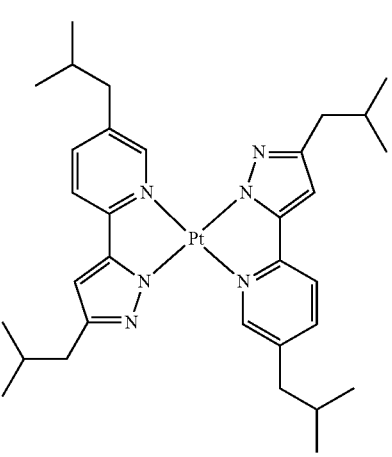
12
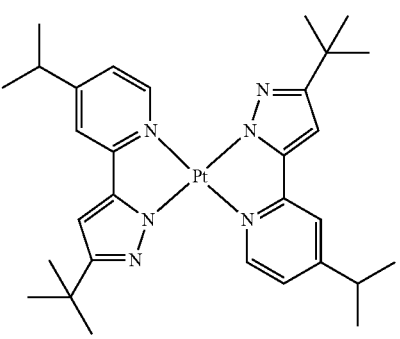
13
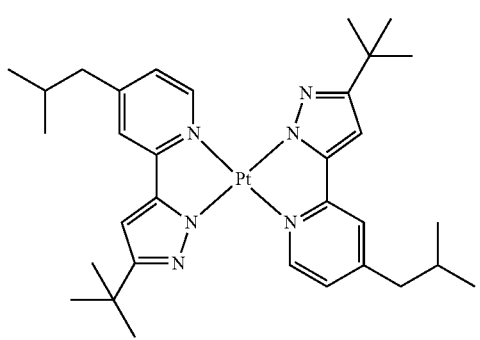

131
-continued
14
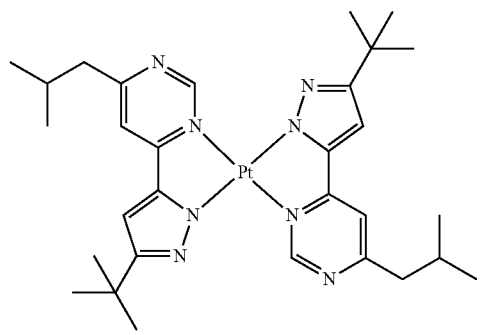
15
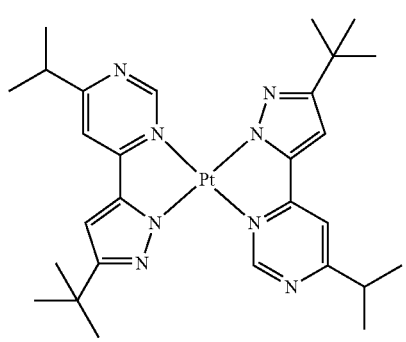
16
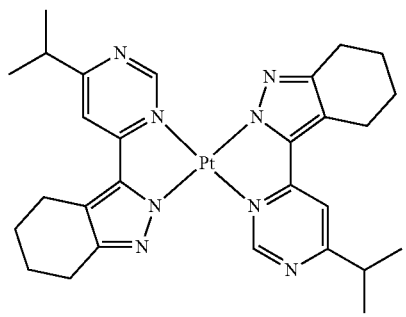
17
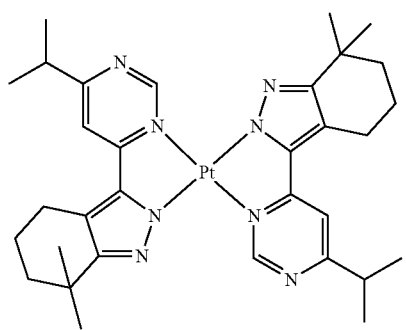
18
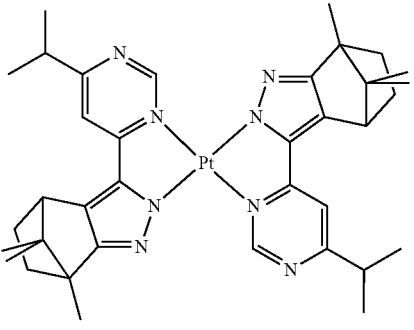
132
-continued
19
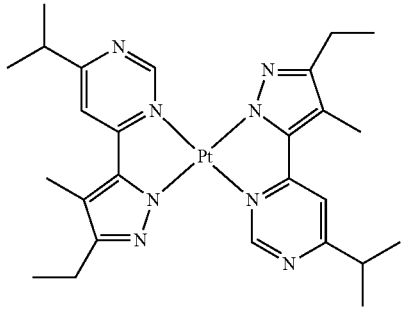
20
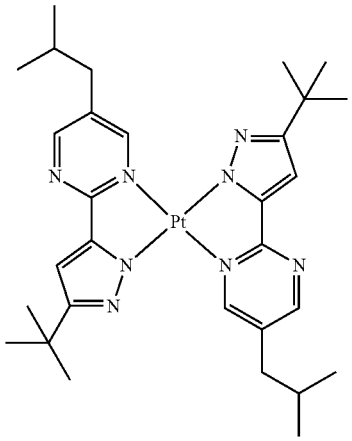
21
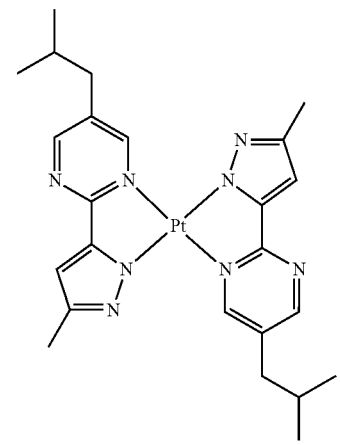
22
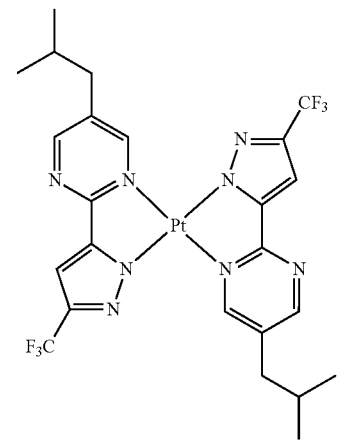

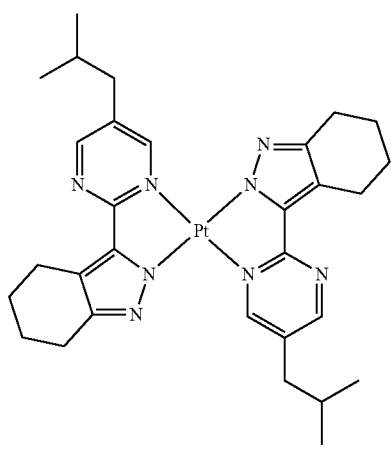
23
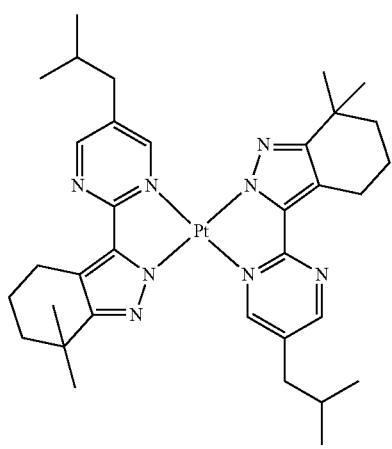
24
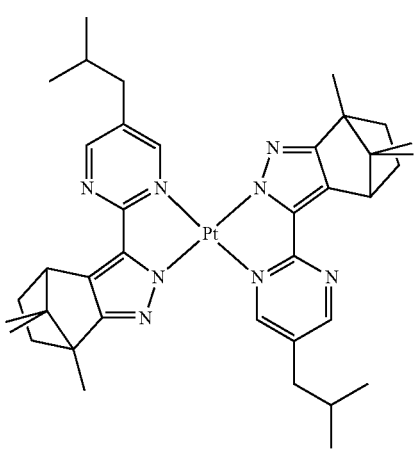
25
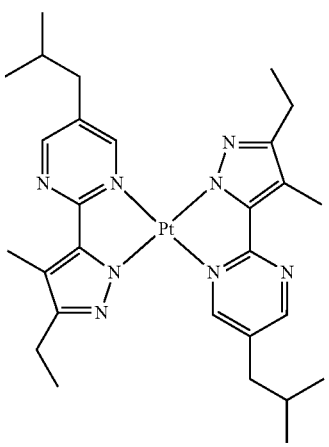
26
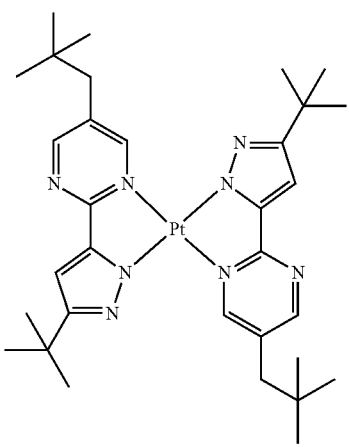
27
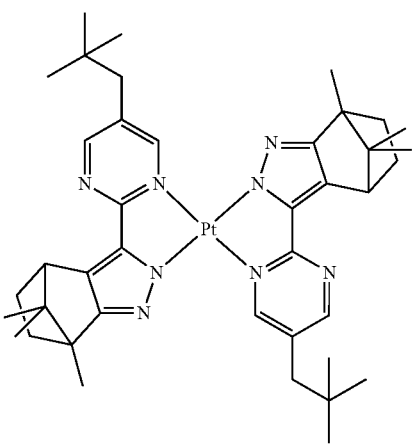
28

-continued

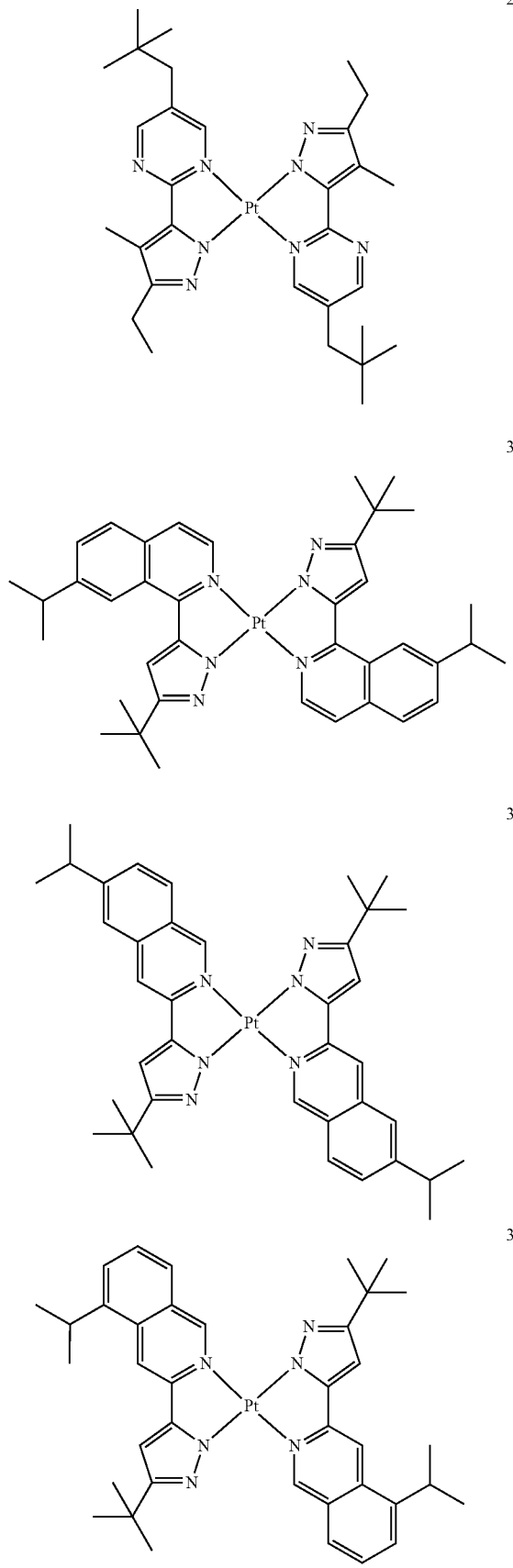

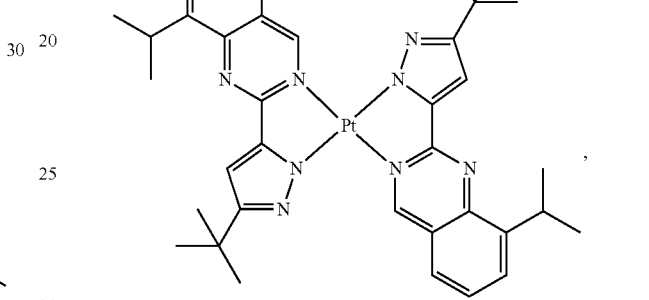

9. An organic light-emitting diode comprising: a substrate; a first electrode; a second electrode disposed opposite to the first electrode; and an emission layer disposed between the first electrode and the second electrode, the emission layer comprising at least one of the organometallic compounds of claim 1.

10. The organic light-emitting diode of claim 9, further comprising at least one of a hole injection layer, a hole transport layer, a functional layer having both hole injection and hole transport capabilities, a buffer layer, and an electron blocking layer between the first electrode and the emission layer, and at least one of a hole blocking layer, an electron transport layer, and a functional layer having both electron injection and electron transport capabilities between the emission layer and the second electrode.

11. The organic light-emitting diode of claim 9, the organometallic compound in the emission layer serving as a phosphorescent dopant emitting light based on the mechanism of phosphorescence, the emission layer further comprising a host.

12. The organic light-emitting diode of claim 11, the host comprising a carbazole-based compound.

13. The organic light-emitting diode of claim 12, the carbazole-based compound being represented by Formula 10 below:

<Formula 10>

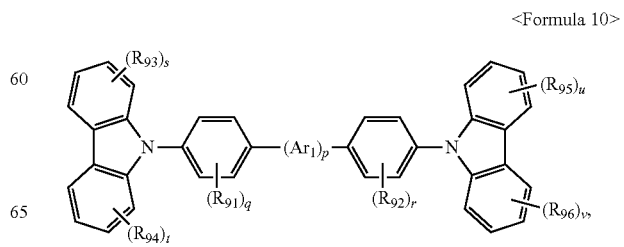

Ar₁ in Formula 10 being one selected from among a substituted or unsubstituted $C_1$-$C_{60}$ alkylene group, a substituted or unsubstituted $C_2$-$C_{60}$ alkenylene group, —C(=O)—, —N($R_{100}$)— (where $R_{100}$ is one of a substituted or unsubstituted $C_6$-$C_{60}$ aryl group and a substituted or unsubstituted $C_2$-$C_{60}$ heteroaryl group), a substituted or unsubstituted $C_6$-$C_{60}$ arylene group, and a substituted or unsubstituted $C_2$-$C_{60}$ heteroarylene group, p in Formula 10 being an integer from 0 to 10, $R_{91}$ to $R_{96}$ in Formula 10 each being independently selected from among a hydrogen atom, a deuterium atom, a halogen atom, a hydroxy group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, and a substituted or unsubstituted $C_2$-$C_{60}$ heteroaryl group, two adjacent substituents of $R_{91}$ to $R_{96}$ being optionally linked to each other to form one of a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, and a substituted or unsubstituted $C_2$-$C_{20}$ heteroaromatic group; and q, r, s, t, u, and v in Formula 10 each being independently an integer from 1 to 4.

14. The organic light-emitting diode of claim 12, the carbazole-based compound being one of Compounds H1 to H30 below:

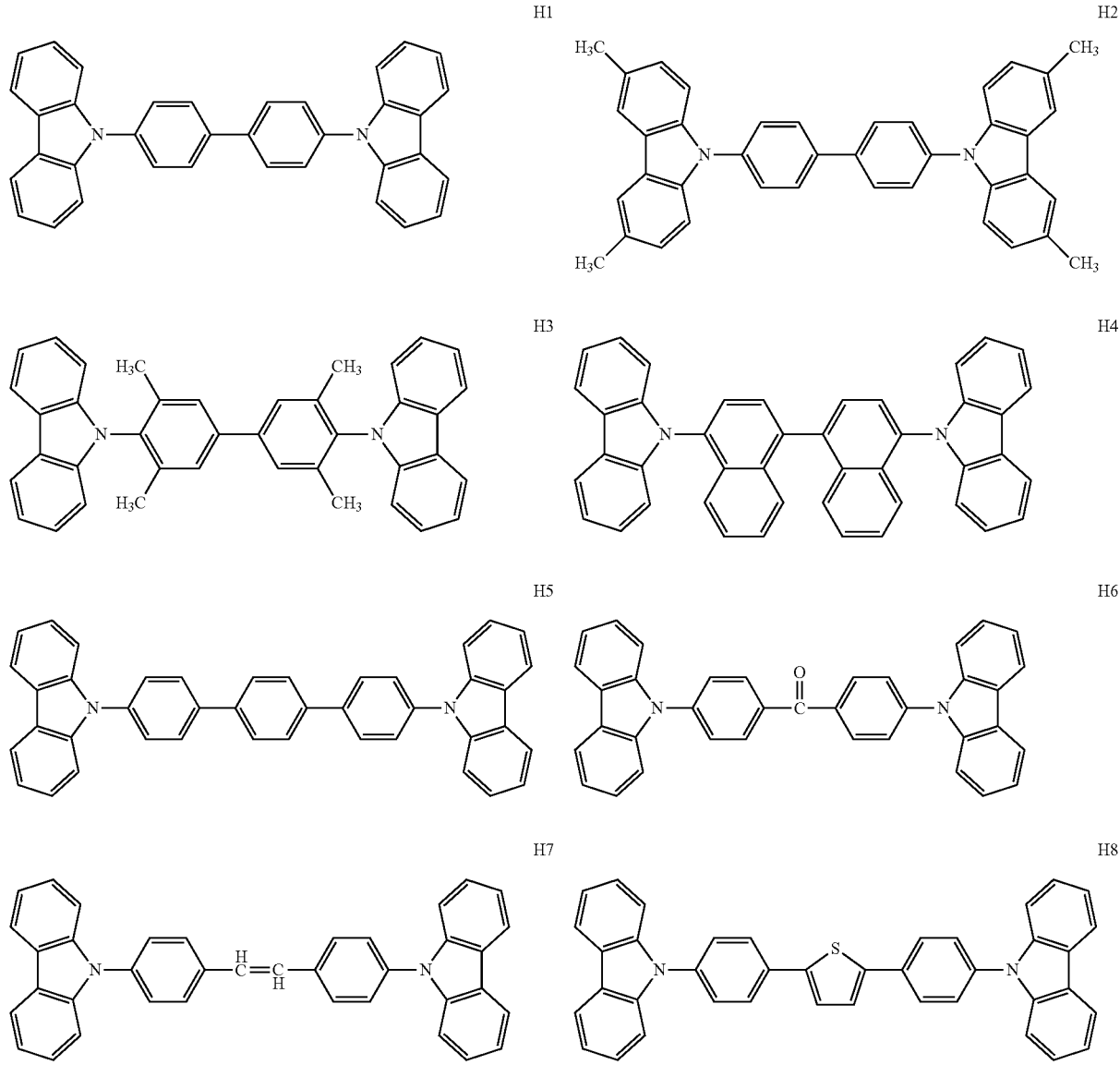

H9
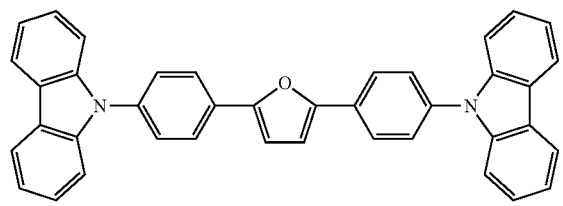
H10
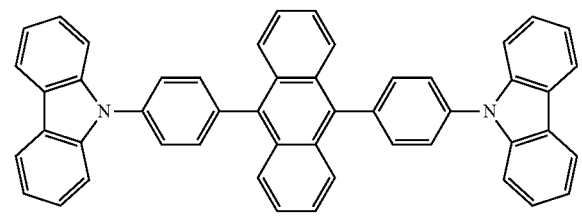
H11
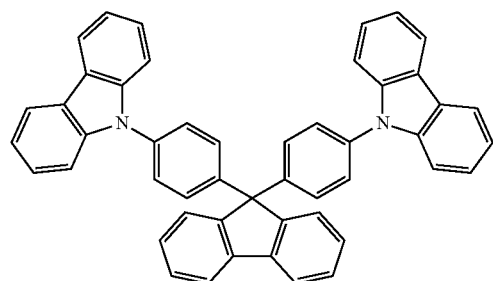
H12
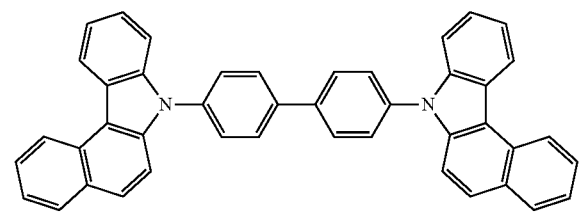
H13
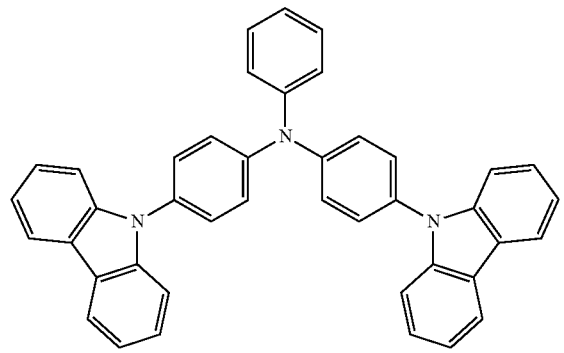
H14
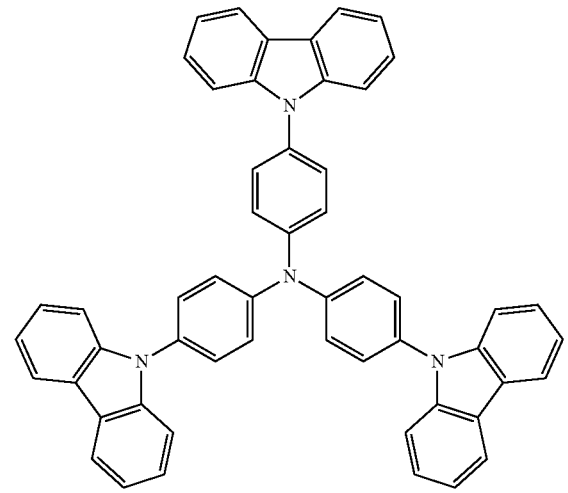
H15
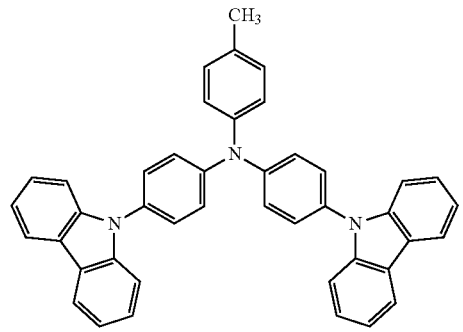
H16
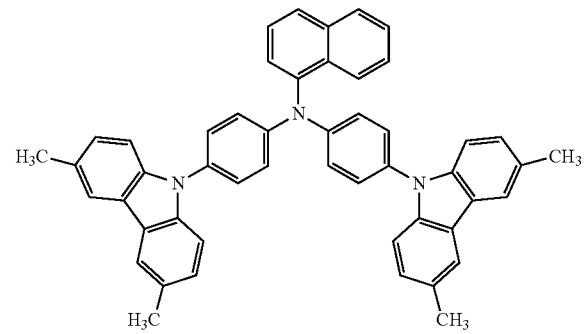

-continued
H17
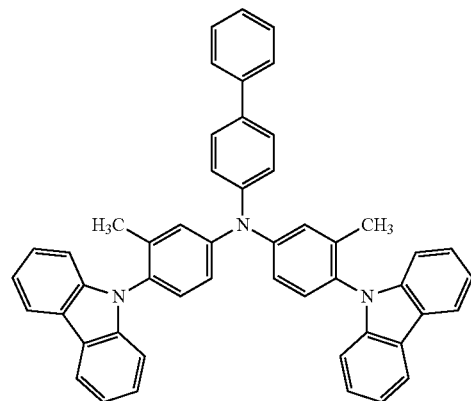
H18
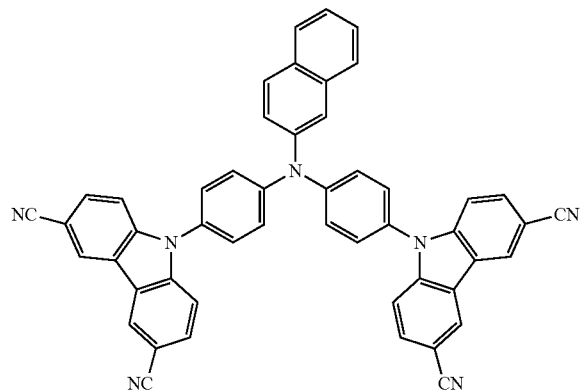
H19
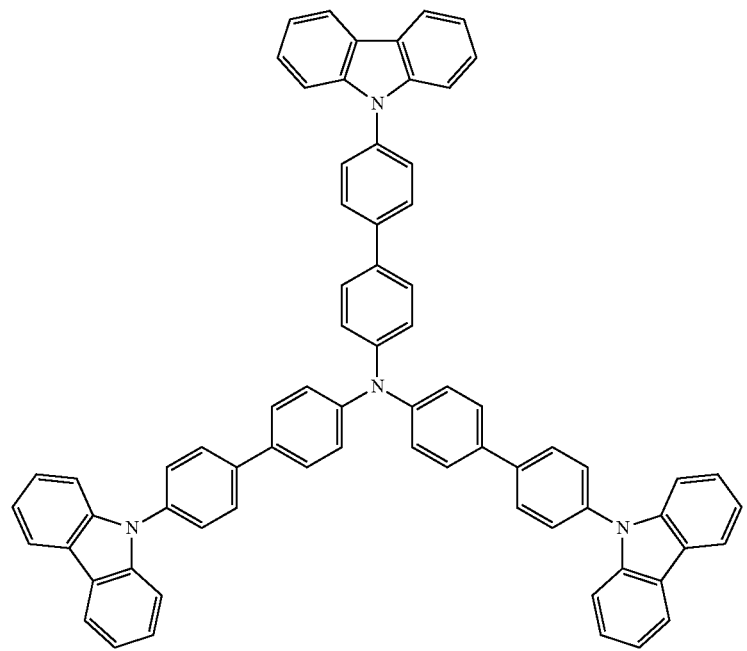
H20
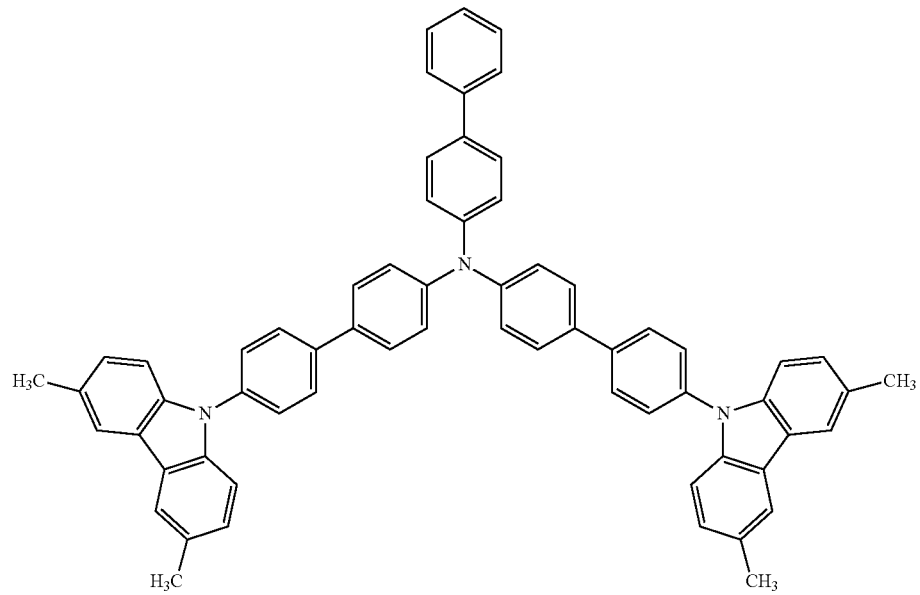

-continued
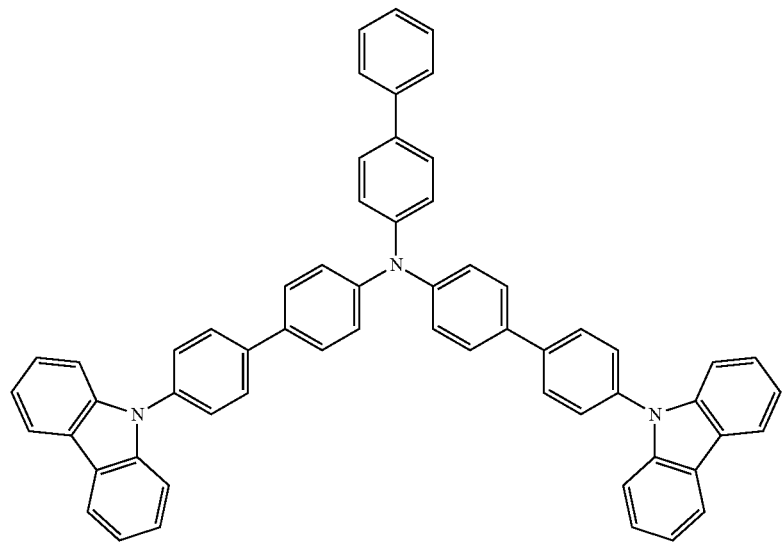
H21
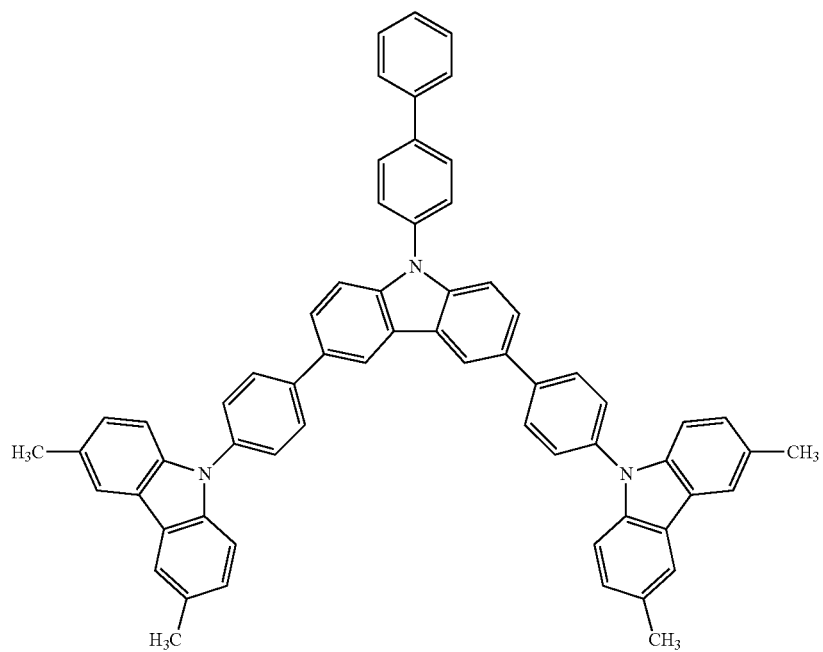
H22
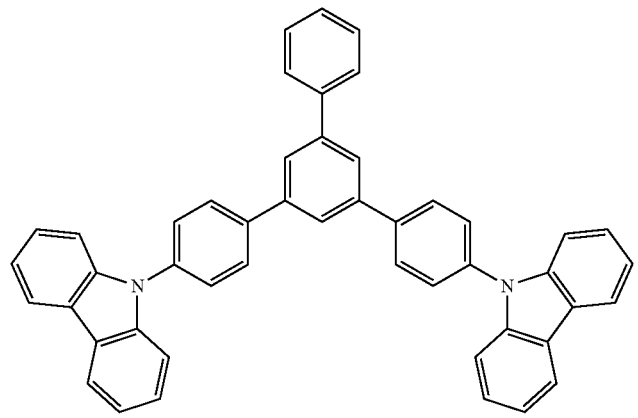
H23

H24
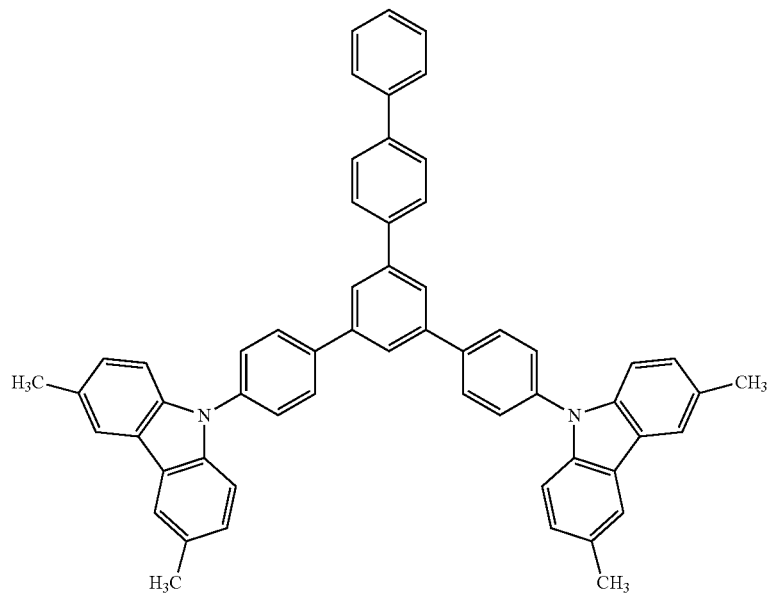
H25
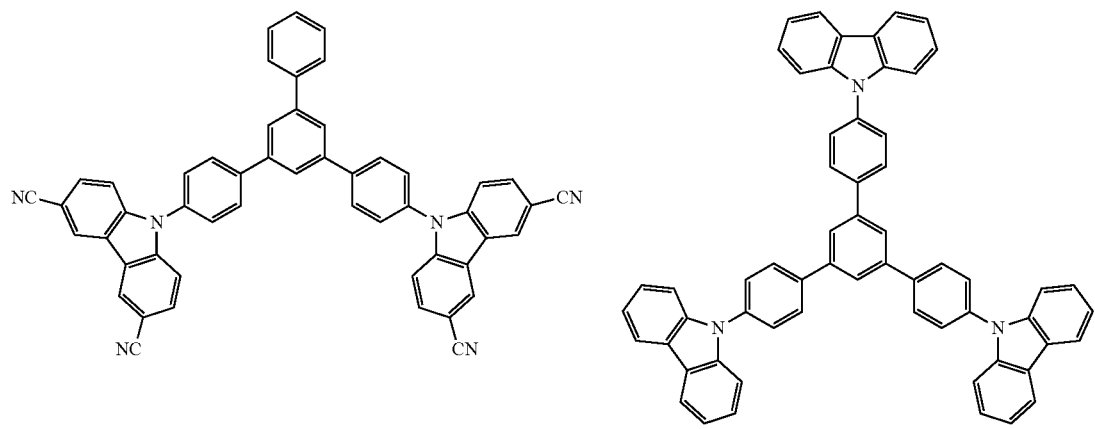
H26
H27
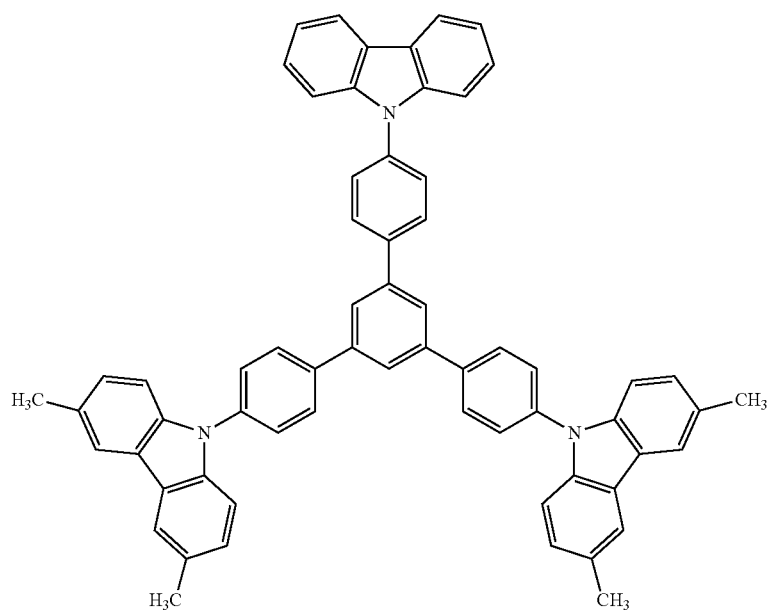

-continued
H28
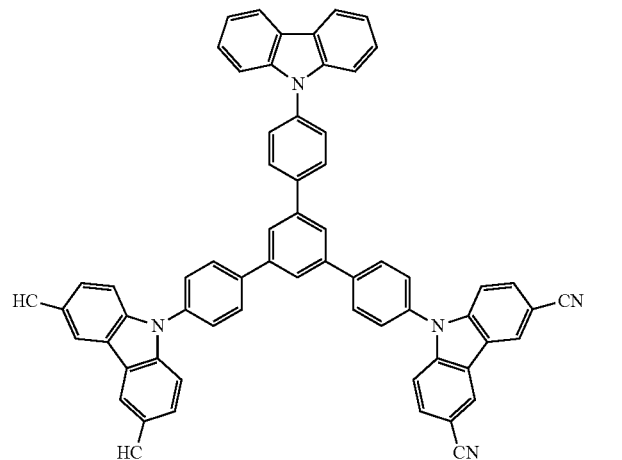
H29
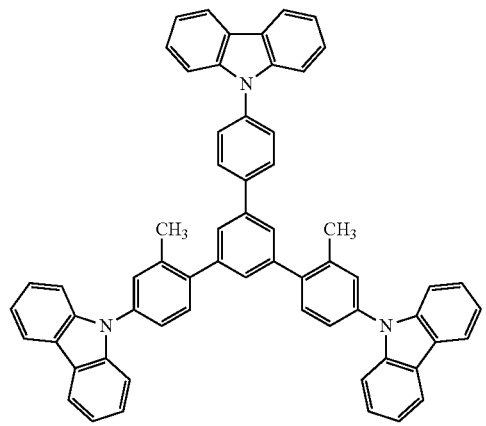
H30
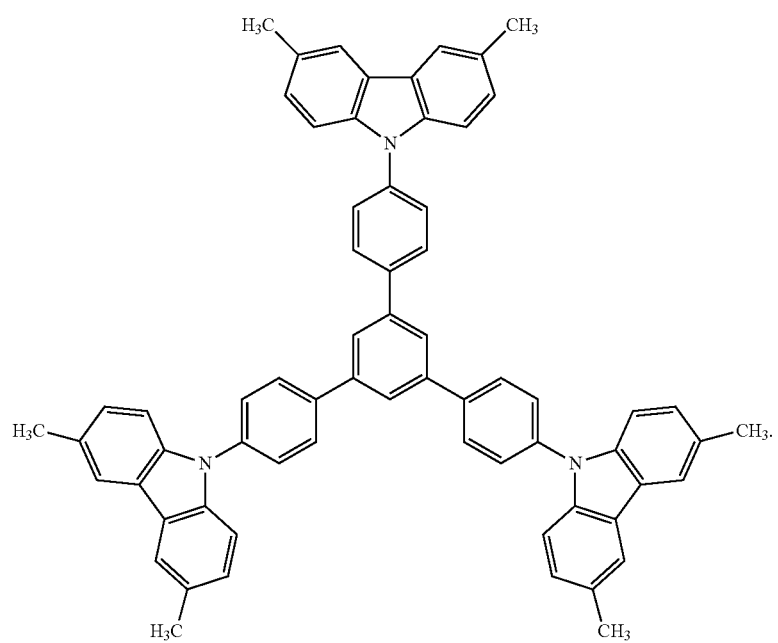
* * * * *